(12) United States Patent
Dahl et al.

(10) Patent No.: US 6,812,370 B2
(45) Date of Patent: Nov. 2, 2004

(54) COMPOSITIONS COMPRISING HEXAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 373 days.

(21) Appl. No.: 10/012,704

(22) Filed: Dec. 12, 2001

(65) Prior Publication Data

US 2002/0143218 A1 Oct. 3, 2002

Related U.S. Application Data

(60) Provisional application No. 60/262,842, filed on Jan. 19, 2001, provisional application No. 60/312,563, filed on Aug. 15, 2001, and provisional application No. 60/337,918, filed on Nov. 9, 2001.

(51) Int. Cl.$^7$ .............................. C07C 13/28; C07C 7/00
(52) U.S. Cl. ........................... 585/352; 585/16; 585/21; 585/800; 585/802; 585/803; 117/68; 117/69; 117/70
(58) Field of Search ........................... 585/803, 21, 16, 585/800, 352, 802; 117/68, 69, 70

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,952,748 A | 8/1990 | Alexander | |
| 4,952,749 A | 8/1990 | Alexander | |
| 4,952,757 A | 8/1990 | Alexander | |
| 4,982,049 A | 1/1991 | Alexander | |
| 5,017,734 A | 5/1991 | Baum | |
| 5,019,665 A | 5/1991 | Partridge | |
| 5,126,274 A * | 6/1992 | McIver et al. | 436/140 |
| 5,245,104 A | 9/1993 | Cullick | |
| 5,268,513 A | 12/1993 | Shen | |
| 5,298,666 A | 3/1994 | Shen | |
| 5,306,851 A | 4/1994 | Wu | |
| 5,334,228 A * | 8/1994 | Ashjian et al. | 44/347 |
| 5,347,063 A | 9/1994 | Shen | |
| 5,369,213 A | 11/1994 | Shen | |
| 5,380,947 A | 1/1995 | Chen | |
| 5,382,684 A | 1/1995 | Moini | |
| 5,397,488 A | 3/1995 | Chen | |
| 5,410,092 A | 4/1995 | Shen | |
| 5,414,189 A * | 5/1995 | Chen et al. | 585/801 |
| 5,430,193 A | 7/1995 | Shen | |
| 5,461,184 A | 10/1995 | Swanson | |
| 5,498,812 A | 3/1996 | Bradway | |
| 5,576,355 A | 11/1996 | Chen | |
| 6,235,851 B1 | 5/2001 | Ishii | |

FOREIGN PATENT DOCUMENTS

EP 0399851 11/1996

WO WO 95/11472 4/1995

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).
Balaban, et al., Systemic Classification and Nomenclature of Diamond Hydrocarbons–I, *Tetrahedron*, 34, pp. 3599–3606, (1978) no month.
Badziag, P., et al., "Nanometre–sized Diamonds are More Stable than Graphite", *Nature*, vol. 343, pp. 244–245, and 517 (Jan. 1990).
Bagrii, Ye, et al., "Catalytic Breakdown of Paraffinic Hydrocarbons in the Presence of Adamantanes", *Petrol. Chem USSR*, vol. 30, No. 2, pp. 131–134, (1990) no month.
Chung, et al., Recent Development in High–Energy Density Liquid Fuels, *Energy and Fuels*, 13, pp. 641–649, (1999) no month.
Dahl, J., et al., Diamondoid Hydrocarbons as Indicators of Natural Oil Cracking, *Nature*, 399, pp. 54–57, (1999) no month.
Drexler, Eric K., *Nanosystems: Molecular Machinery Manufacturing and Computation*, John Wiley & Sons, pp. 238–249, (1992) no month.
Fort, Jr., et al., Adamantane: Consequences of the Diamondoid Structure, *Chem. Rev.*, 64, pp. 277–300, (1964) no month.
Hala, V.S., et al., "Analyse Unds erwendung on Pyrolyseol", *Jahrgang*, pp. 85–87, (Feb. 1971) In German—English Abstract on p. 85 considered to extent of abstract.
Landa, S., "Adamantane and Its Homologues", *Current Science*, Gangalore, India, Vo. 32, pp. 485–489 (1963) no month.
Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512–1521, (1995) no month.
McKervey, Synthetic Approaches to Large Diamondoid Hydrocarbonds, *Tetrahedron*, 36, pp. 971–992, (1980) no month.
Machacek, V., et al., "Let Od Objeveni Adamantanu", *Chemicke Listy/svazek*, pp. 753–761, (1982) Russian—English Abstract on p. 761 considered to extent of abstract, no month.
Oya, A, et al., "Carbonization of Adamantanes to a Graphitizable Carbon", *Fuel*, vol. 60, pp. 667–669, (Aug. 1981).

*Primary Examiner*—Elizabeth D. Wood
(74) *Attorney, Agent, or Firm*—Burns, Doane, Swecker & Mathis, L.L.P.

(List continued on next page.)

(57) ABSTRACT

Disclosed are compositions comprising one or more hexamantanes. Specifically disclosed are compositions comprising 25 to 100 weight percent of one or more hexamantanes. Also disclosed are novel processes for the separation and isolation of hexamantane components into recoverable fractions from a feedstock containing at least a higher diamondoid component which contains one or more hexamantane components.

37 Claims, 107 Drawing Sheets

OTHER PUBLICATIONS

Petrov, A., "Hydrocarbons of Adamantane Series as Indicies of Petroleum Catagenesis Process", *Advances in Organic Geo Chemistry*, 6th International Meeting on Organic Geochemistry, pp. 517–522 (1973) no month.

Prusova, D., Liquid Chromatography of Adamantanes and Carbon Adsorbents, *J. Chrom*, 234, pp. 1–11, (1982) no month.

Rollman, L., et al., "Adamantanes From Petroleum, with Zeolites", American Chemical Study, 210th ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[11.7.1.1$^{2,18}$.0$^{3,16}$.0$^{4,13}$.0$^{5,10}$.0$^{6,14}$.0$^{7,11}$.0$^{15,20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*, vol. 114, No. 2, pp. 497–505, (1992) no month.

Supryadkina, NY, et al., "Catalytic Dealkylation of Alkyladamantanes", *Petrol. Chem., USSR*, vol. 28, No. 2, pp. 103–110, (1988) no month.

Tominaga, K., et al., "Next–generation Fine Chemicals Raw Material–Adamantane", *Chem Econ Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983) no month.

Wingert, W., "G.c.–m.s. Analysis of Diamondoid Hydrocarbons in Smackover Petroleums", *Fuel*, vol. 71, pp. 37–42, (Jan. 1992).

\* cited by examiner

Symmetrical
Hexamantanes

Enantiomeric
Hexamantanes

* Mirror plane indicating enantiomeric pair of pentamantanes

A)

B)

A)

B)

Hexamantane #2 Crystals

| Hypercarb HPLC Fraction # | 1 | 2 | 3 | 4 | 5 | 6 | 7 | 8 | 9 | 10 | 11 | 12 | 13 | 14 | 15 | 16 | 17 | Fully Condensed Hexamantane | |
|---|---|---|---|---|---|---|---|---|---|---|---|---|---|---|---|---|---|---|---|
| 1 | | | | | | | | | | | | | | | | | | | |
| 2 | | | | | | | | | | | | | | | | | | | |
| 3 | | | | | | | | | | | | | | | | | | | |
| 4 | | | | | | | | | | | | | | | | | | ▓ | |
| 5 | | | | | | | | | | | | | | | | | | | |
| 26 | | | | | | | | | | | | | | | | | | | |
| 27 | | | | | | | | | | | | | ▓ | | | | | | Hex 13 |
| 28 | | | | | | | | | | | | | ▓ | | | | | | |
| 29 | | | | | | | | | | | | | | ▓ | | | | | Hex 14 |
| 30 | x | | | | | | | | | | | | | ▓ | | | | | Hex 1 |
| 31 | | | | | | | | | | | | | | ▓ | | | | | Hex 10 |
| 32 | | | | | | | | | | ▓ | | | ▓ | | | | | | Hex 11 |
| 33 | | | | | | | | | | ▓ | | | | | | | | | |
| 34 | | | | | | | | | | ▓ | | | | | | | | | |
| 35 | | | | | | | | | | ▓ | | | | | | | | | |
| 43 | | | | | | | | | | | | | | | | | | | |
| 44 | | | | | | ▓ | | | | | | | | | | | | | Hex 6 |
| 45 | | | | | | | | | | | | | | | | | | | |
| 46 | | | | | | | | | | | | | | | | | | | |
| 47 | | | | | | | | | | | | | | | | | | | |
| 48 | | | | | | | | | | | | | | | | | | | |
| 49 | | | | | | | | | ▓ | | | | | | | ▓ | | | Hex 15 |
| 50 | | | | | | | | | ▓ | | | | | | | ▓ | | | Hex 9 |
| 51 | | | | | | | | | ▓ | | | | | | | | | | |
| 52 | | ▓ | | | | | | | ▓ | | | | | | | | | | |
| 53 | | ▓ | | | | | | | | | | | | | | | | | |
| 54 | | ▓ | | | | | | | | | | | | | | | | | Hex 2 |
| 55 | | ▓ | | | | | | | | | | | | | | | | | |
| 56 | | ▓ | | | | | | | | | | | | | | | | | |
| 57 | | ▓ | | | | | | | | | | | | | | | | | |
| 58 | | ▓ | | | | | | | | | | | | | | | | | |
| 59 | | ▓ | | | | | | | | | | | | | | | | | |
| 60 | | ▓ | | | | | | | | | | | | | | | | | |
| 61 | | ▓ | | | | | | | | | | | | | | | | | |
| 62 | | | | | | | | | | | | | | | | | | | |
| 72 | | | | | | | ▓ | | | | | | | | | | | | |
| 73 | | | | | | | ▓ | | | | | | | | | | | | |
| 74 | | | | | | | ▓ | | | | | | | | | | | | |
| 75 | | | | | | | ▓ | | | | | | | | | | | | Hex 7 |
| 76 | | | | | | | ▓ | | | | | | | | | | | | |
| 77 | | | | | | | ▓ | | | | | | | | | | | | |
| 78 | | | | | | | | | | | | | | | | | | | |
| 84 | | | | | | | | | | | | | | | | | | | |

A) Hypercarb HPLC Fraction #53

B)

A)

B)

A)

B)

A)

B)

A) ODS HPLC Fraction #36

B)

A)

B)

A)

B)

A)

B)

A)

Methylcyclohexamantane
HPLC 37 Fraction 19-21

B)

Methylcyclohexamantane
HPLC 37 Fraction 23

Name: [1(2)314]A Hexamantane
Formula: $C_{30}H_{36}$
Molecular Weight 396.618
Molecular Weight (Exact) 396.2817013
Symmetry $C_1$ Carbon Framework CPK Representation

[1(2)314]A Hexamantane
View into Specified Diamond Crystal Lattice Plane

| 111 | 110 | 100 |
|---|---|---|
|  |  |  |
|  |  |  |
|  |  |  |
|  |  |  |
|  |  | |
|  |  | |

Name: [1(2)314]B Hexamantane
Formula: $C_{30}H_{36}$
Molecular Weight 396.618
Molecular Weight (Exact) 396.2817013
Symmetry $C_1$ Carbon
Framework CPK
Representation

[1(2)314]B Hexamantane
View into Specified Diamond Crystal Lattice Plane

| 111 | 110 | 100 |
|---|---|---|

Name: [12(1)32]A Hexamantane
Formula: $C_{30}H_{36}$
Molecular Weight: 396.618
Molecular Weight (Exact): 396.2817013
Symmetry: $C_1$ Carbon Framework CPK Representation

[12(1)32]A Hexamantane
View into Specified Diamond Crystal Lattice Plane
111　　110　　100

Name: [12(1)32]B Hexamantane
Formula: $C_{30}H_{36}$
Molecular Weight: 396.618
Molecular Weight (Exact): 396.2817013
Symmetry: $C_i$ Carbon Framework CPK Representation

[12(1)32]B Hexamantane
View into Specified Diamond Crystal Lattice Plane

| 111 | 110 | 100 |
|---|---|---|
|  |  |  |
|  |  |  |
|  |  |  |
|  |  |  |
|  |  |  |
|  |  |  |

Name: [12(1)34]A Hexamantane
Formula: $C_{30}H_{36}$
Molecular Weight 396.618
Molecular Weight (Exact) 396.2817013
Symmetry $C_1$ Carbon Framework CPK Representation

[12(1)34]A Hexamantane
View into Specified Diamond Crystal Lattice Plane

| 111 | 110 | 100 |
|---|---|---|
|  |  |  |
|  |  |  |
|  |  |  |
|  |  |  |
|  |  |  |

Name: [12(1)34]B Hexamantane
Formula: $C_{30}H_{36}$
Molecular Weight 396.618
Molecular Weight (Exact) 396.2817013
Symmetry $C_1$ Carbon Framework CPK Representation

[12(1)34]B Hexamantane
View into Specified Diamond Crystal Lattice Plane 111 110 100

Name: [12(1,3)4] Hexamantane
Formula: $C_{30}H_{36}$
Molecular Weight 396.618
Molecular Weight (Exact) 396.2817013
Symmetry Carbon
Framework CPK
Representation

[12(1,3)4] Hexamantane
View into Specified Diamond Crystal Lattice Plane

| 111 | 110 | 100 |
|---|---|---|
|  |  |  |
|  |  |  |
|  |  |  |
|  |  |  |
|  |  | |
|  |  | |

Name: [12(3)14]A Hexamantane
Formula: $C_{30}H_{36}$
Molecular Weight 396.618
Molecular Weight (Exact) 396.2817013
Symmetry $C_1$ Carbon Framework CPK Representation

[12(3)14]A Hexamantane
View into Specified Diamond Crystal Lattice Plane

| 111 | 110 | 100 |
|---|---|---|
|  |  |  |
|  |  |  |
|  |  |  |
|  |  |  |
|  |  |  |
|  |  |  |

Name: [12(3)14]B Hexamantane
Formula: $C_{30}H_{36}$
Molecular Weight 396.618
Molecular Weight (Exact) 396.2817013
Symmetry $C_1$ Carbon Framework CPK Representation

[12(3)14]B Hexamantane
View into Specified Diamond Crystal Lattice Plane 111 110 100

Name: [121(2)3] A Hexamantane
Formula: $C_{30}H_{36}$
Molecular Weight 396.618
Molecular Weight (Exact) 396.2817013
Symmetry $C_1$ Carbon Framework CPK Representation

[121(2)3]A Hexamantane
View into Specified Diamond Crystal Lattice Plane
111 110 100

Name: [121(2)3]B hexamantane
Formula: $C_{30}H_{36}$
Molecular Weight 396.618
Molecular Weight (Exact) 396.2817013
Symmetry $C_1$ Carbon Framework CPK Representation

[121(2)3]B hexamantane
View into Specified Diamond Crystal Lattice Plane 111　　　　　　110　　　　　　100

Name: [12123] A Hexamantane
Formula: $C_{30}H_{36}$
Molecular Weight: 396.618
Molecular Weight (Exact): 396.2817013
Symmetry: $C_1$ Carbon Framework CPK Representation

[12123]A Hexamantane
View into Specified Diamond Crystal Lattice Plane

Name: [12123]B Hexamantane
Formula: $C_{30}H_{36}$
Molecular Weight 396.618
Molecular Weight (Exact) 396.2817013
Symmetry $C_1$ Carbon
Framework CPK
Representati

[12123]B Hexamantane
View into Specified Diamond Crystal Lattice Plane 111 110 100

Name: [12131] A Hexamantane
Formula: $C_{30}H_{36}$
Molecular Weight 396.618
Molecular Weight (Exact) 396.2817013
Symmetry Carbon Framework CPK Representation

[12131]A Hexamantane
View into Specified Diamond Crystal Lattice Plane

Name: [12131]B Hexamantane
Formula: $C_{30}H_{36}$
Molecular Weight 396.618
Molecular Weight (Exact) 396.2817013
Symmetry Carbon Framework CPK Representaion

[12131]B Hexamantane
View into Specified Diamond Crystal Lattice Plane 111        110        100

Name: [12134] A Hexamantane
Formula: $C_{30}H_{36}$
Molecular Weight 396.618
Molecular Weight (Exact) 396.2817013
Symmetry $C_1$ Carbon Framework CPK Representation

[12134]A Hexamantane
View into Specified Diamond Crystal Lattice Plane 111    110    100

Name: [12134]B Hexamantane
Formula: $C_{30}H_{36}$
Molecular Weight: 396.618
Molecular Weight (Exact): 396.2817013
Symmetry: $C_i$ Carbon Framework CPK Representaion

[12134]B Hexamantane
View into Specified Diamond Crystal Lattice Plane
111  110  100

Name: [12324]A Hexamantane
Formula: $C_{30}H_{36}$
Molecular Weight: 396.618
Molecular Weight (Exact): 396.281701
Symmetry: $C_2$ Carbon Framework CPK Representation

[12324]A Hexamantane
View into Specified Diamond Crystal Lattice Plane 111     110     100

Name: [12324]B Hexamantane
Formula: $C_{30}H_{36}$
Molecular Weight 396.618
Molecular Weight (Exact) 396.281701
Symmetry $C_2$ Carbon Framework CPK Representation

[12324]B Hexamantane
View into Specified Diamond Crystal Lattice Plane 111  110  100

Name: [12341]A Hexamantane
Formula: $C_{30}H_{36}$
Molecular Weight 396.618
Molecular Weight (Exact) 396.2817013
Symmetry $C_2$ CPK Representation

[12341]A Hexamantane
View into Specified Diamond Crystal Lattice Plane 111 110 100

Name: [12341]B Hexamantane
Formula: $C_{30}H_{36}$
Molecular Weight 396.618
Molecular Weight (Exact) 396.2817013
Symmetry $C_2$ Carbon Framework CPK Representation

[12341]B Hexamantane
View into Specified Diamond Crystal Lattice Plane 111          110          100

| | |
|---|---|
| Name: | [12132] A Hexamantane |
| Formula: | $C_{29}H_{34}$ |
| Molecular Weight | 382.591 |
| Molecular Weight (Exact) | 382.2660513 |
| Symmetry | $C_1$ |

Carbon Framework

CPK Representation

[12132]A Hexamantane
View into Specified Diamond Crystal Lattice Plane
111     110     100

Name: [12132] B Hexamantane
Formula: $C_{29}H_{34}$
Molecular Weight: 382.591
Molecular Weight (Exact): 382.2660513
Symmetry: $C_1$ Carbon Framework CPK Representation

[12132]B Hexamantane
View into Specified Diamond Crystal Lattice Plane 111 110 100

Name: [123(1)2] A Hexamantane
Formula: $C_{29}H_{34}$
Molecular Weight 382.591
Molecular Weight (Exact) 382.2660513
Symmetry $C_1$ Carbon
Framework CPK
Representation

[123(1)2]A Hexamantane
View into Specified Diamond Crystal Lattice Plane
111   110   100

Name: [123(1)2] B Hexamantane
Formula: $C_{29}H_{34}$
Molecular Weight 382.591
Molecular Weight (Exact) 382.2660513
Symmetry $C_1$ Carbon Framework CPK Representation

[123(1)2]B Hexamantane
View into Specified Diamond Crystal Lattice Plane 111 110 100

Name: [123(1)4] A Hexamantane
Formula: $C_{29}H_{34}$
Molecular Weight 382.591
Molecular Weight (Exact) 382.2660513
Symmetry $C_1$ Carbon Framework CPK Representation

[123(1)4]A Hexamantane
View into Specified Diamond Crystal Lattice Plane
111　　　　110　　　　100

Name: [123(1)4] B Hexamantane
Formula: $C_{29}H_{34}$
Molecular Weight: 382.591
Molecular Weight (Exact): 382.2660513
Symmetry: $C_1$ Carbon Framework CPK Representation

[123(1)4]B Hexamantane
View into Specified Diamond Crystal Lattice Plane
111    110    100

Name: [12314]A Hexamantane
Formula: $C_{29}H_{34}$
Molecular Weight 382.591
Molecular Weight (Exact) 382.2660513
Symmetry $C_1$ Carbon
Framework CPK
Representation

[12314]A Hexamantane
View into Specified Diamond Crystal Lattice Plane
111  110  100

Name: [12314] B Hexamantane
Formula: $C_{29}H_{34}$
Molecular Weight: 382.591
Molecular Weight (Exact): 382.266053
Symmetry: $C_1$ Carbon Framework CPK Representation

[12314]B Hexamantane
View into Specified Diamond Crystal Lattice Plane 111　　　110　　　100

Name: [1(2)3(1)2] Hexamantane
Formula: $C_{30}H_{36}$
Molecular Weight: 396.618
Molecular Weight (Exact): 396.2817013
Symmetry: $C_{2h}$ Carbon Framework

[1(2)3(1)2] Hexamantane
View into Specified Diamond Crystal Lattice Plane
111       110       100

Name: [12(3)12] Hexamantane
Formula: $C_{30}H_{36}$
Molecular Weight 396.618
Molecular Weight (Exact) 396.2817013
Symmetry $C_S$ Carbon Framework CPK Representation

[12(3)12] Hexamantane
View into Specified Diamond Crystal Lattice Plane

Name: [121(3)4] Hexamantane
Formula: $C_{30}H_{36}$
Molecular Weight: 396.618
Molecular Weight (Exact): 396.2817013
Symmetry: $C_s$ Carbon Framework CPK Representation

[121(3)4] Hexamantane
View into Specified Diamond Crystal Lattice Plane
111　　110　　100

Name: [12121] Hexamantane
Formula: $C_{30}H_{36}$
Molecular Weight 396.618
Molecular Weight (Exact) 396.2817013
Symmetry $C_{2h}$ Carbon Framework CPK Representation

[12121] Hexamantane
View into Specified Diamond Crystal Lattice Plane

Name: [12321] Hexamantane
Formula: $C_{30}H_{36}$
Molecular Weight 396.618
Molecular Weight (Exact) 396.2817013
Symmetry $C_1$ Carbon Framework CPK Representaion

[12321] nexamantane
View into Specified Diamond Crystal Lattice Plane 111    110    100

Name: [12(1)31] Hexamantane
Formula: $C_{29}H_{34}$
Molecular Weight: 382.591
Molecular Weight (Exact): 382.2660513
Symmetry: $C_s$ Carbon Framework CPK Representation

[12(1)31 Hexamantane
View into Specified Diamond Crystal Lattice Plane 111 110 100

Name: [12(3)41] Hexamantane
Formula: $C_{29}H_{34}$
Molecular Weight: 382.591
Molecular Weight (Exact): 382.2660513
Symmetry: $C_s$ Carbon Framework

[12(3)41 Hexamantane
View into Specified Diamond Crystal Lattice Plane

Name: [12312] Hexamantane
Formula: $C_{26}H_{30}$
Molecular Weight 342.526
Molecular Weight (Exact) 342.2347511
Symmetry $D_{3d}$ Carbon Framework CPK Representation

[12312] Hexamantane
View into Specified Diamond Crystal Lattice Plane
111  110  100

Name: [1(2)3(1)4]A Hexamantane
Formula: $C_{30}H_{36}$
Molecular Weight 396.618
Molecular Weight (Exact) 396.2817013
Symmetry $C_2$ Carbon Framework

[1(2)3(1)4]A Hexamantane
View into Specified Diamond Crystal Lattice Plane 111  110  100

Name: [1(2)3(1)4]B Hexamantane
Formula: $C_{30}H_{36}$
Molecular Weight 396.618
Molecular Weight (Exact) 396.2817013
Symmetry $C_2$ Carbon
Framework CPK
Representation

[1(2)3(1)4]B Hexamantane
View into Specified Diamond Crystal Lattice Plane 111 110 100

COMPOSITIONS COMPRISING HEXAMANTANES AND PROCESSES FOR THEIR SEPARATION

REFERENCE TO RELATED APPLICATIONS

This application claims priority under 35 USC §119(e) to United States Provisional Application No. 60/262,842 filed Jan. 19, 2001, United States Provisional Application Serial No. 60/312,563 filed Aug. 15, 2001, and to United States Provisional Application Serial No. 60/337,918 filed Nov. 9, 2001 all of which are incorporated by reference.

BACKGROUND OF THE INVENTION

1. Field of the Invention

This invention is directed to novel compositions comprising one or more hexamantanes. This invention is also directed to novel processes for the separation and isolation of hexamantane components into recoverable fractions from a feedstock containing at least a higher diamondoid component which contains one or more hexamantane components.

References

The following publications and patents are cited in this application as superscript numbers:

All of the above publications and patents are herein incorporated by reference in their entirety to the same extent as if each individual publication or patent was specifically and individually indicated to be incorporated by reference in its entirety.

2. State of the Art

Hexamantanes are bridged-ring cycloalkanes. They are the face-fused hexamers of adamantane (tricyclo[3.3.1.1$^{3,7}$] decane) or $C_{10}H_{16}$. The compounds have a "diamondoid" topology, which means their carbon atom arrangement is superimposable on a fragment of the diamond lattice (FIG. 1). Hexamantanes possess six of the "diamond crystal units" and therefore, it is postulated that there are thirty-nine possible hexamantane structure (FIG. 2). Among them, twenty-eight of the thirty-nine have the molecular formula $C_{30}H_{36}$ (molecular weight 396) and of these, six are symmetrical, having no enantiomers. Ten of the thirty-nine hexamantanes have the molecular formula $C_{29}H_{34}$ (molecular weight 382), and the remaining hexamantane is fully condensed having the molecular formula $C_{26}H_{30}$ (molecular weight 342), at times referred to as "cyclohexamantane."

[3] McKervey, *Synthetic Approaches to Large Diamondoid Hydrocarbons*, Tetrahedron, 36:971–992 (1980).
[7] Balaban et al., Systematic *Classification and Nomenclature of Diamondoid Hydrocarbons*—I, Tetrahedron. 34, 3599–3606 (1978).

Very little published work is available for hexamantanes and higher molecular weight diamondoids. Hexamantanes have not been artificially synthesized and these compounds have been recently thought only to have a theoretical existence.[1,7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding the practical application of hexamantanes. This fact is probably due to extreme difficulties encountered in their isolation and due to failed synthesis attempts. Lin and Wilk, for example, discuss the possible presence of pentamantanes in a gas condensate and further postulate that hexamantane may also be present.[1] The researchers postulate the existence of the compounds based on a mass spectrometric fragmentation pattern. They did not, however, report the isolation of a single pentamantane or hexamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement route employing Lewis acid catalysts, useful in synthesizing triamantane and lower diamondoids have been unsuccessful to synthesize tetramantanes or pentamantane. Hexamantanes have also failed like synthesis attempts.

[1] Lin, et al., *Natural Occurrence of Tetramantane* ($C_{22}H_{28}$), *Pentamantane* ($C_{26}H_{32}$) *and Hexamantane* ($C_{30}H_{36}$) in a *Deep Petroleum Reservoir*, Fuel, 74(10):1512–1521 (1995)
[2] Alexander, et al., Purfication of Hydrocarbonaceous Fractions, U.S. Pat. No. 4,952,748, issued Aug. 28, 1990
[3] McKervey, *Synthetic Approaches to Large Diamondoid Hydrocarbons*, Tetrahedron, 36:971–992 (1980).
[7] Balaban et al., Systematic *Classification and Nomenclature of Diamondoid Hydrocarbons*—I, Tetrahedron. 34, 3599–3606 (1978).

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$) and excellent thermal conductivity.

In addition, based on theoretical considerations, the hexamantanes have sizes in the nanometer range and, in view of the properties noted above, the inventors contemplate that such compounds would have utility in micro- and molecular-electronics and nanotechnology applications. In particular, the rigidity, strength, stability, variety of structural forms and multiple attachment sites shown by these molecules makes possible accurate construction of robust, durable, precision devices with nanometer dimensions. The various hexamantanes are nanometer sized three-dimensional structures showing different spacial arrangements. This translates into a variety of rigid shapes and sizes for the thirty-nine hexamantanes. For example, [12121] hexamantane is rod shaped, [121(3)4] hexamantane is "T" shaped, while [12134] is "L" shaped and [1(2)3(1)2] is flat with four lobes. The two enantiomers of [12131] are left and right-handed screw like structures. A variety of other shapes exist among the hexamantanes which may serve in applications which depend upon specific geometries. It has been estimated that MicroElectroMechanical Systems (MEMs) constructed out of diamond should last 10,000 times longer then current polysilicon MEMs, and diamond is chemically benign and would not promote allergic reactions in biomedical applications.[6] Again, the inventors contemplate that hexamantanes would have similar attractive properties. Furthermore, some of the isomers of hexamantane (molecular weight 396 and 382) possess chirality, offering opportunities for making nanotechnology objects of great structural specificity and ones which have useful optical properties. Applications of these hexamantanes include molecular electronics, photonic devices, nanomechanical devices, nanostructured polymers and other materials.

[6] Sandia National Laboratories (2000), *World's First Diamond Micromachines Created at Sandia*, Press Release, (Feb. 22, 2000) www.Sandia.gov.

Notwithstanding these advantages of hexamantanes, the art, as noted above, fails to provide for compositions comprising hexamantanes or for processes that would lead to these compositions. In view of the above, there is an ongoing need in the art to provide for compositions comprising one or more hexamantanes.

SUMMARY OF THE INVENTION

This invention is directed to novel compositions comprising one or more hexamantane components.

Accordingly, in one of its composition aspects, this invention is directed to a composition comprising one or more hexamantane components wherein said composition comprises at least about 25 weight percent hexamantane components based on the total weight of the diamondoids in the composition with the proviso that when only a single hexamantane is present than that hexamantane is not the fully condensed unsubstituted hexamantane component, unsubstituted cyclohexamantane, which has the molecular formula $C_{26}H_{30}$.

In another of its composition aspects, the compositions preferably comprise one or more hexamantane components wherein the hexamantane components make up from about 50 to 100 weight percent, preferably about 70 to 100 weight percent, more preferably about 90 to 100 weight percent and even more preferably about 95 to 100 weight percent hexamantane components based on the total weight of the diamondoids in the composition with the proviso that if only one hexamantane compound is present it is not the fully condensed unsubstituted hexamantane, unsubstituted cyclohexamantane.

In another of its composition aspects, the compositions comprise at least about 10 weight percent and preferably at least about 20 weight percent of hexamantanes based upon the total weight of the composition with the above proviso that said single hexamantane compound is not the fully condensed unsubstituted hexamantane. Other compositions of this invention, with this proviso, contain from 50 to 100 weight percent, 70 to 100 weight percent, 95 to 100 weight percent and 99 to 100 weight percent of hexamantane based upon the total weight percent of the composition.

In another of its composition aspects, the compositions comprise from about 70 to 100 weight percent, more preferably from about 90 to 100 weight percent, even more preferably from about 95 to 100 weight percent and most preferably from about 99 to 100 weight percent of a single hexamantane component, including isolated optical isomers thereof, based upon the total weight of the composition, all with the proviso that said single hexamantane compound is not the fully condensed unsubstituted hexamantane, cyclohexamantane.

When such compositions are sufficiently enriched in hexamantane components the hexamantanes can form crystal structures. Accordingly, another aspect of this invention is directed to a composition comprising a hexamantane crystal with the proviso that when there is only a single hexamantane component, then it is not the fully condensed unsubstituted cyclohexamantane. Since such hexamantane can co-crystallize, another aspect of this invention is directed to the co-crystals comprising crystals of at least two hexamantane components.

This invention is also directed to novel processes for the separation and isolation of hexamantane components into recoverable fractions from a feedstock containing hexamantane components and nonhexamantane materials These processes for recovering a composition enriched in hexamantane components entail removing at least a portion of the components which have a boiling point below the lowest boiling hexamantane component and utilizing a subsequent separation technique to recover hexamantane components from the resulting residue. Accordingly, this aspect is directed to processes which comprise:

a) selecting a feedstock comprising recoverable amounts of hexamantane components and nonhexamantane materials;

b) removing from the feedstock a sufficient amount of nonhexamantane materials having a boiling points below the lowest boiling point of hexamantane component in the feedstock under conditions to form a treated feedstock enriched in hexamantane components which can be recovered;

C) recovering hexamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the treated feedstock can be thermally treated to pyrolyze at least a sufficient amount of nondiamondoid components therefrom under conditions to provide a thermally treated feedstock retaining recoverable amounts of hexamantane. Such a pyrolization step prior to step c) is useful for thermally degrading at least a portion of any materials remaining in the treated feedstock having a thermal stability lower than the hexamantane components. This pyrolysis step can be carried out before step b), if desired.

BRIEF DESCRIPTION OF THE DRAWINGS

FIG. 1 illustrates the correlation of the structures of diamondoids to subunits of the diamond crystal lattice.

FIG. 7A, shows the first column cuts containing two of the hexamantanes from Feedstock B. FIG. 7B, shows the second column peaks isolated and sent to the traps. From this procedure pure hexamantanes were isolated (FIGS. 8 and 9), hexamantane #2, the second hexamantane to elute in our GC/MS assay, while hexamantane #8 is the eighth to elute.

FIG. 14A illustrates the GC of Feedstock B atmospheric distillation fraction #6, exemplified in Example 1, which was used as feedstock in pyrolytic processing.

FIG. 14B illustrates the GC of the product of the pyrolytic process.

FIG. 15 illustrates results of a preparative HPLC separation of Feedstock B distillate cut pyrolysis product saturated hydrocarbon fraction showing HPLC fractions taken using octadecyl silane "ODS" columns and acetone mobile phase. Most hexamantanes are separated from one another on ODS. Hexamantanes are numbered in order of their elution order on our GC/MS assay.

FIG. 19 illustrates results of a preparative HPLC separation of Feedstock B distillate cut pyrolysis product saturated hydrocarbon fraction showing HPLC fractions taken using Hypercarb columns and acetone mobile phase. Hexamantanes are numbered in order of their elution order on our GC/MS assay.

FIGS. 29A, B) illustrated photomicrographs of methylcyclohexamantanes (mol. wt. 356) crystals. FIG. 29A illustrates a crystal precipitated from Hypercarb HPLC fractions #19–21 and FIG. 29B illustrates a crystal precipitated from Hypercarb HPLC fractions #23

DETAILED DESCRIPTION OF THE INVENTION

This invention is directed to compositions comprising one or more hexamantane components. However, prior to describing this invention in further detail, the following terms will first be defined.

Definitions

As used herein, the following terms have the following meanings.

Figure 1:
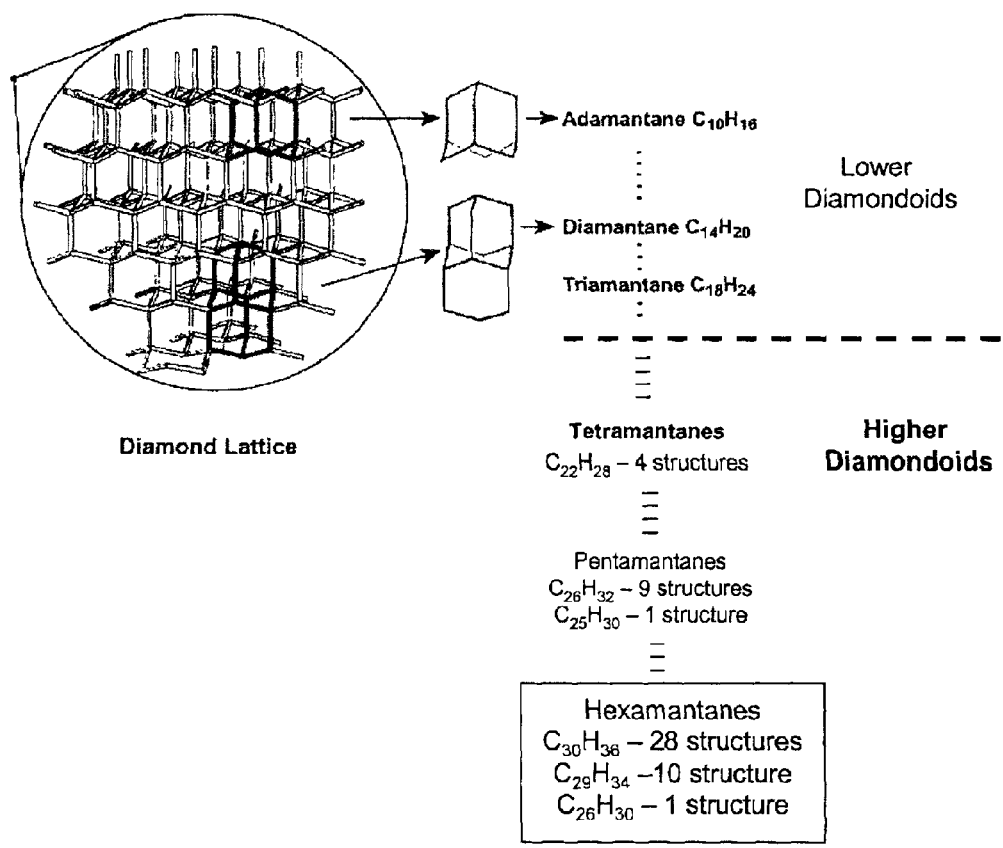
FIG. 1 illustrates the cage-shaped structure of diamondoids and their correlation to diamonds. Specifically.

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, dodecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "hexamantanes," "higher diamondoids" and "nonhexamantane higher diamondoids" as these terms are defined herein.

Figure 2:
FIG. 2 illustrates the carbon framework of the 39 hexamantane structures, 15 of which are pairs of enantiomers (30 hexamantanes).
Figure 2:
Figure 2:
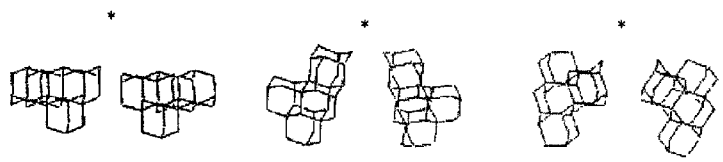
Figure 2:
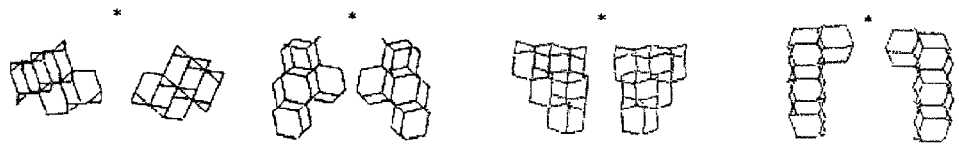
Figure 2:
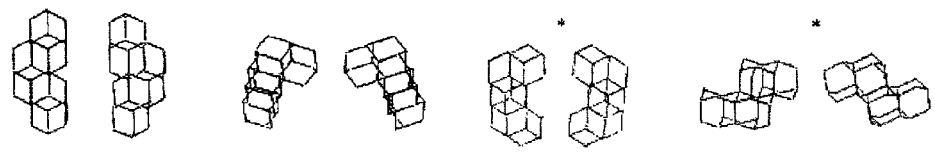
Figure 2:
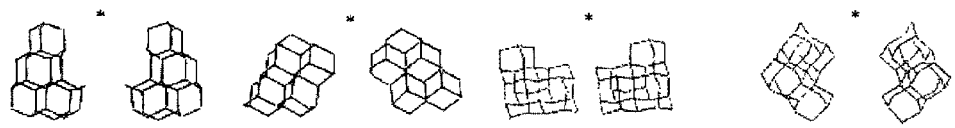

The term "hexamantanes" refers to diamondoids that are the face-fused hexamers of adamantane. There are thirty-nine possible unsubstituted hexamantanes (FIG. 2). Among them, twenty-eight of the thirty-nine have the molecular formula $C_{30}H_{36}$ (molecular weight 396) and of these, six are symmetrical, having no enantiomers. Ten of the thirty-nine hexamantanes have the molecular formula $C_{29}H_{34}$ (molecular weight 382), and the remaining hexamantane is the fully condensed hexamantane having the molecular formula $C_{26}H_{30}$ (molecular weight 342). Each of the hexamantanes possesses a different three-dimensional structure. "Hexamantanes" include alkyl substituted as described for diamondoids, generally.

The term "hexamantane component" refers to any single substituted or unsubstituted hexamantane, including optical isomers (enantiomers).

The term "lower diamondoids "or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not hexamantane components are referred to as " nonhexamantane higher diamondoids."

The term "feedstock" or "hydrocarbonaceous feedstock" refers to hydrocarbonaceous materials comprising recoverable amounts of one or more hexamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. The latter is typically characterized as comprising components having a boiling point both below and above hexamantane components, which have molecular weights starting from 342 through 396 and have boiling points starting at about 350° C. (atmospheric equivalent pressure). Typical feedstocks may also contain impurities such as sediment, metals including nickel and vanadium and other inorganics. They may also contain heteromolecules containing sulfur, nitrogen and the like. All of these materials which are not hexamantanes are referred to as "nonhexamantane materials" or "nonhexamantane components".

The term "enriched" when used to describe the state of purity of one or more bexamantane components refers to such materials at least partially separated from nonhexamantane materials, and in the case of "enriched" individual hexamantane components, from other hexamantane components so as to be at a concentration at least 25 and preferably at least 100 times as great as the concentration exhibited in a feedstock. Preferably "enriched" hexamantane or "enriched" hexamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%, 95%, or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

[8] Chen, et al., Isolation of High Purity Diamondoid Fractions and Components, U.S. Pat. No. 5,414,189 issued May 9, 1995.

The terms "distillation" and "distilling" refer to atmospheric, reduced pressure distillation, and elevated pressure distillation conducted to concentrate hexamantane components by removal of nonhexamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched hexamantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to enrich and isolate higher diamond compositions are set forth in U.S. Provisional Patent Application No. 60/262,842 filed Jan. 19, 2001; U.S. Provisional Patent Application No. 60/300,148 filed Jun. 21, 2001; and U.S. Provisional Patent Application No. 60/307,063 filed Jul. 20, 2001. These applications are herein incorporated by reference in their entirety.

To obtain the hexamantane compositions described herein, a feedstock is selected such that said feedstock comprises recoverable amounts of hexamantane components. Preferably, such feedstock comprises at least about 1 ppb (part per billion) of hexamantane components. It is understood, of course, that feedstocks having higher concentrations of hexamantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates recovered from the Norphlet Formation in the Gulf of Mexico and from the LeDuc Formation in Canada.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada.

The feedstocks used to obtain the compositions of this invention typically comprise nondiamondoid components having boiling points both below and above the hexamantane components as well as lower diamondoids and non-hexamantane higher diamondoids. A sufficient amount of these contaminants is removed from the feedstocks to provide treated feedstocks from which the hexamantane components can be enriched and recovered.

The removal of nondiamondoids, lower diamondoids and nonhexamantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nonhexamantane diamondoids having boiling points less than that of the lowest boiling point hexamantane component. Temperature profiles for distillation runs and the resulting distillation cuts can be determined on the basis of the hexamantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified hexamantane. The cuts, which are enriched in hexamantane or a particular hexamantane component of interest, are retained and may require further purification. For recovery of hexamantanes, the preferred distillation cuts are taken at temperatures of from 330° to about 550° C., preferably from 365 to about 500° C. and especially 390 to 470° C. (atmospheric boiling points). It being understood that substituted hexamantanes may accordingly shift these preferred temperatures to higher temperatures due to the addition of substituent groups. Additional temperature refinements will allow for higher purity cuts for the hexamantane of interest. Other methods for the removal of contaminants and further purification of an enriched hexamantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours). The specific conditions employed are selected such that recoverable amounts of hexamantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a preferred embodiment, is not always necessary to facilitate the recovery, isolation or purification of the hexamantane components. Other separation methods may allow for the concentration of these hexamantane components to be sufficiently high in certain feedstocks that direct purification methods such as chromatography including preparative gas chromatography and high performance liquid chromatography and crystallization may be used to isolate hexamantane components.

Even after distillation or thermal degradation/distillation, further purification of the hexamantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated hexamantanes. These provisions can be combined. For example, preparative capillary gas chromatography can be coupled with high performance liquid chromatography as a first or subsequent separation method.

Further processing using these methods allow for more refined separations which can lead to a pure hexamantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the hexamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction", R. M. Smith, Elsevier Science, December 1997, incorporated herein by reference.

Compositions

This invention is directed to compositions comprising one or more hexamantane components wherein said compositions comprises at least about 25 weight percent hexamantane components based on the total weight of the diamondoids in the compositions with the proviso that when only a single hexamantane is present, that hexamantane is not the fully condensed unsubstituted hexamantane compound which has the molecular formula $C_{26}H_{30}$.

The compositions preferably comprise one or more hexamantanes from about 50 to 100 weight percent, preferably about 70 to 100 weight percent, more preferably about 90 to 100 weight percent and even more preferably about 95 to 100 weight percent hexamantane components based on the total weight of the diamondoids in the composition with the proviso that if only one hexamantane compound is present, it is not the fully-condensed unsubstituted hexamantane, unsubstituted cyclohexamantane.

Such hexamantane-enriched compositions are obtained through the series of unit operations described above which can be used to concentrate hexamantanes to at least 25 times and more preferably at least 100 times the levels at which they occur in readily-available feedstocks, again with the proviso that if only one hexamantane compound is present, it is not the fully condensed unsubstituted hexamantane; wherein the total weight percent of hexamantane components in the compositions is preferably at least 10% by weight based upon the total weight of the composition. In a more preferred aspect, the composition is directed to a total weight percent of hexamantane components from 50 to 100 weight percent, more preferably 70 to 100 weight percent and even more preferably 95 or 99 to 100 weight percent based upon the total weight percent of the composition.

In another of its composition aspects, the compositions comprise an enriched individual hexamantane component such that they contain from 70 to 100 weight percent, more preferably from 90 to 100 weight percent, even more preferably from 95 to 100 weight percent and most preferably from 99 to 100 weight percent of a single hexamantane component, including isolated optical isomers thereof with the proviso that said single hexamantane component is not the fully condensed unsubstituted hexamantane.

Figure 30:
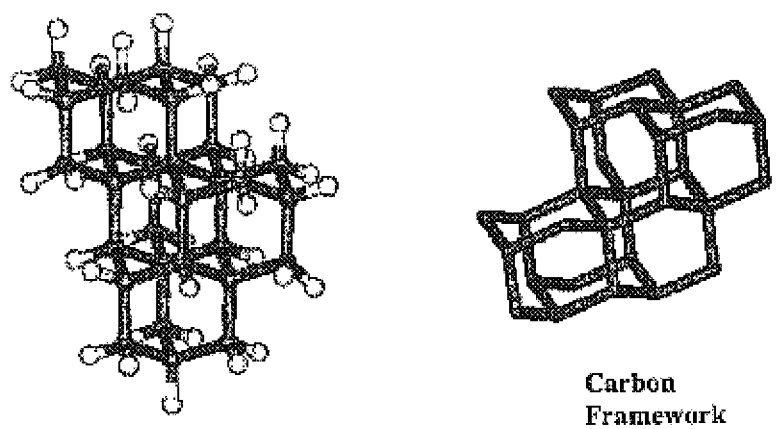
FIGS. 30 through 107 illustrate the size and structure with views into various diamond crystal lattice planes for each of the 39 hexamantane structures.
Figure 30:
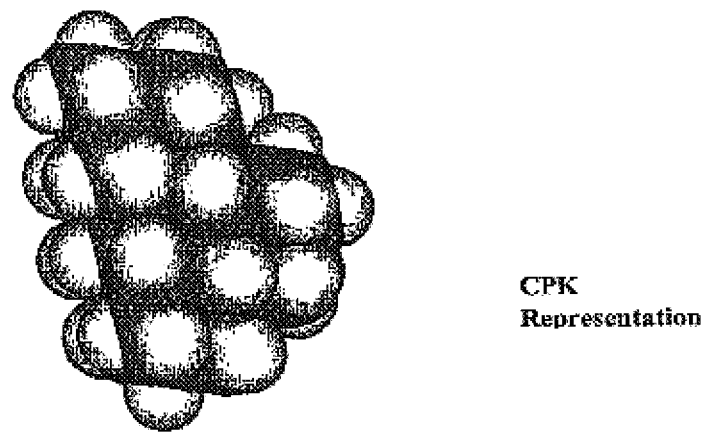
Figure 31:
Figure 31:
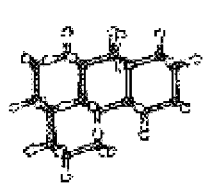
Figure 31:
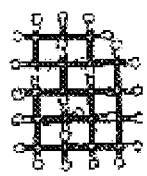
Figure 31:
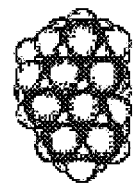
Figure 31:
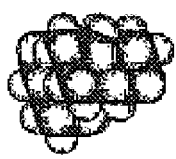
Figure 31:
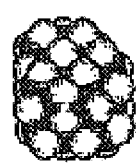
Figure 31:
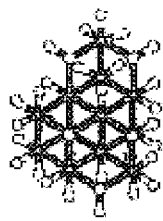
Figure 31:
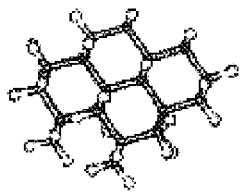
Figure 31:
Figure 31:
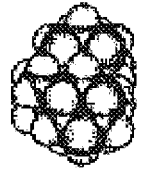
Figure 31:
Figure 31:
Figure 31:
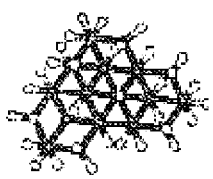
Figure 31:
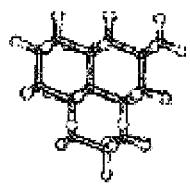
Figure 31:
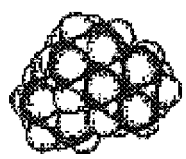
Figure 31:
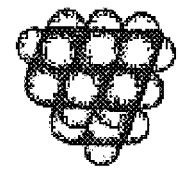
Figure 32:
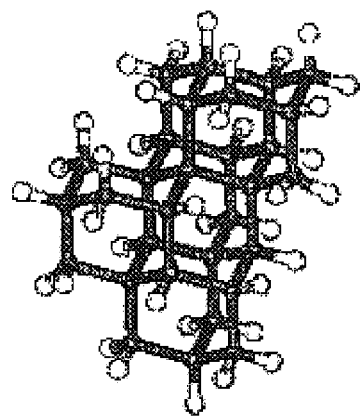
Figure 32:
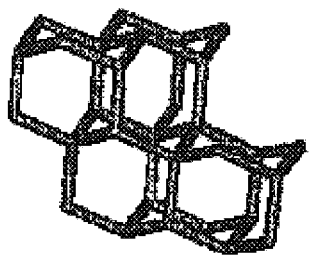
Figure 32:
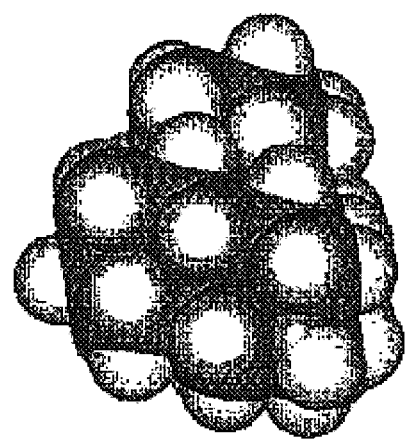
Figure 33:
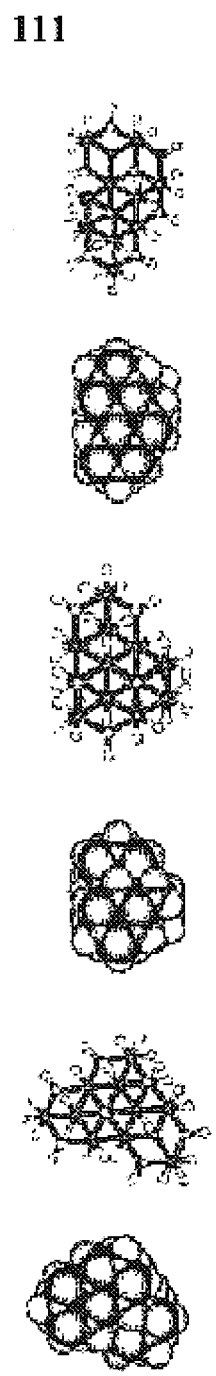
Figure 33:
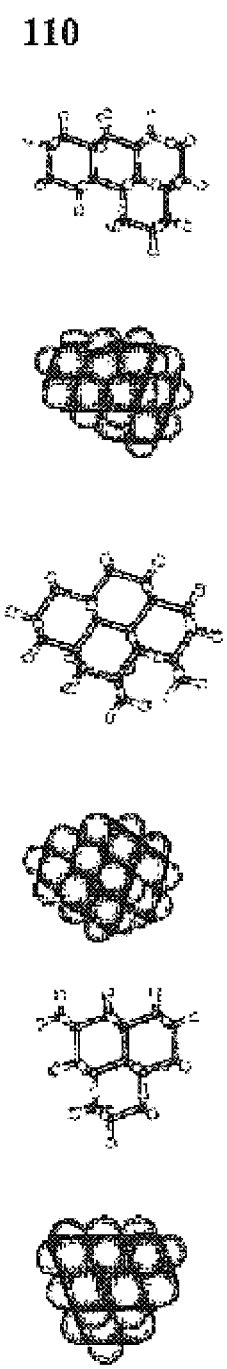
Figure 33:
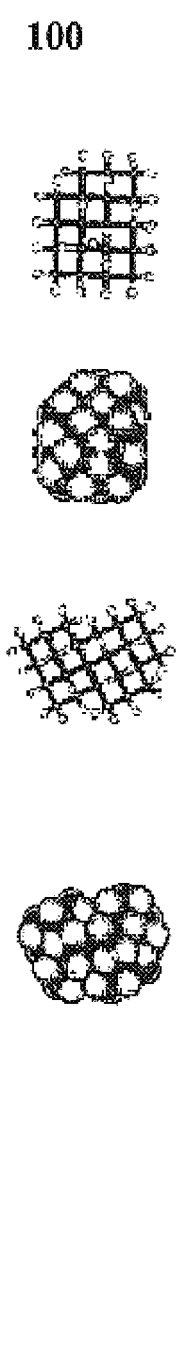
Figure 34:
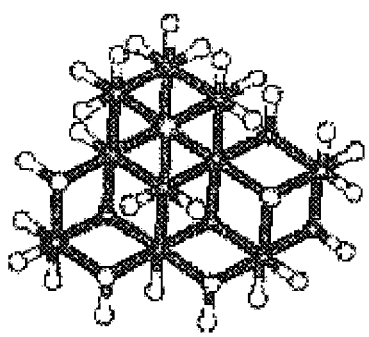
Figure 34:
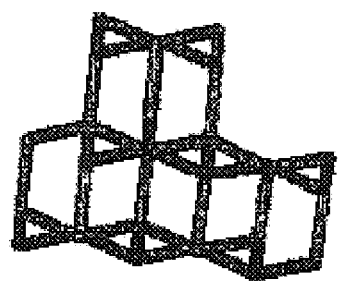
Figure 34:
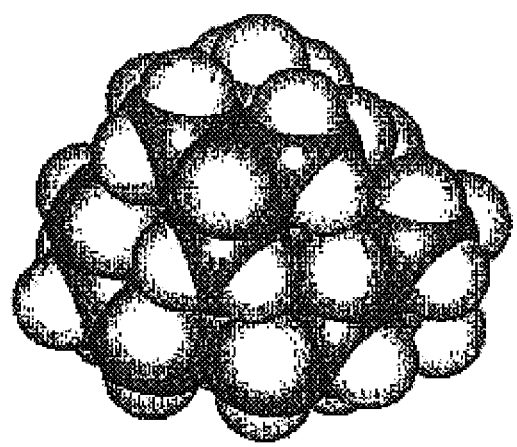
Figure 35:
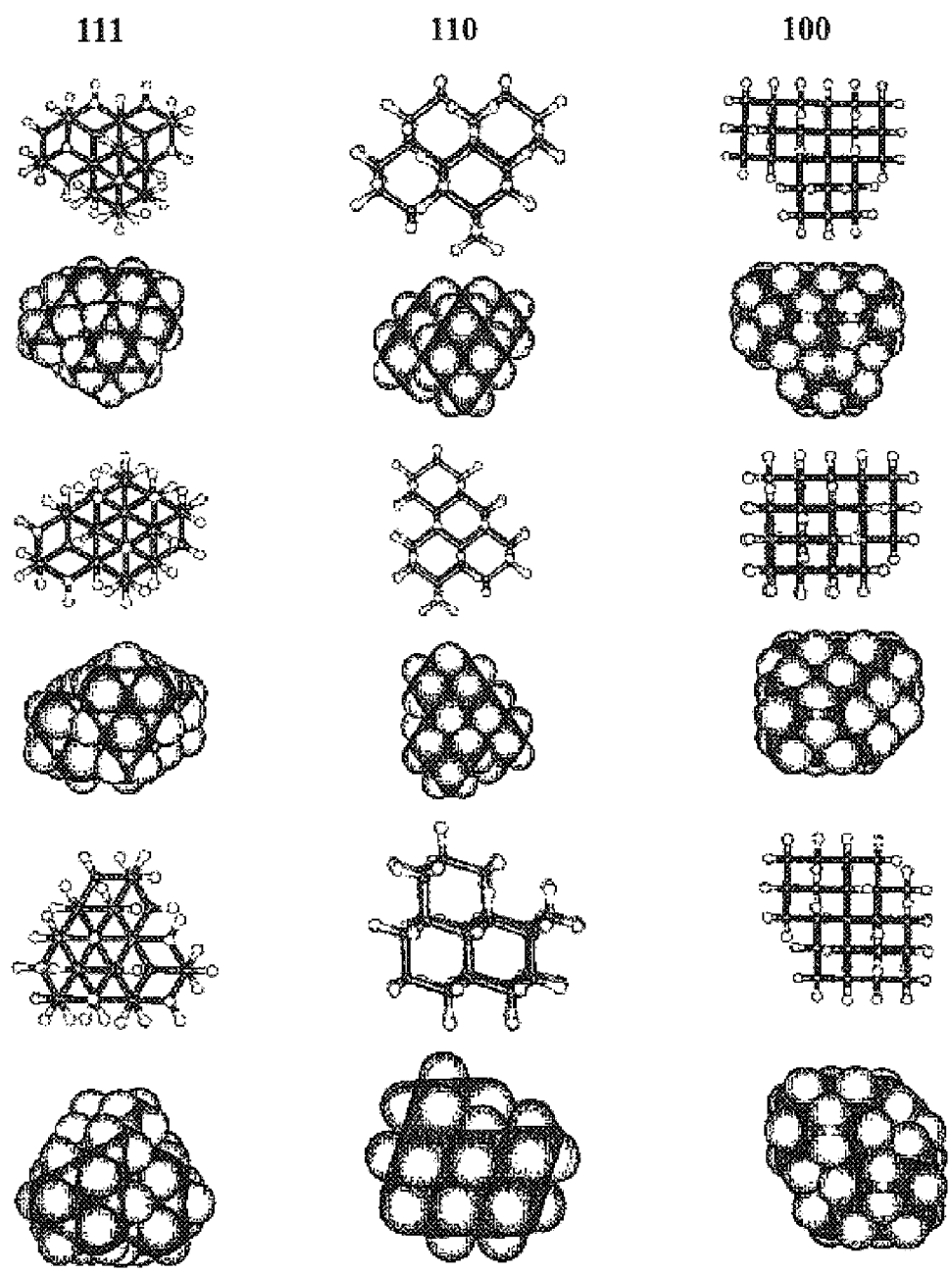
Figure 36:
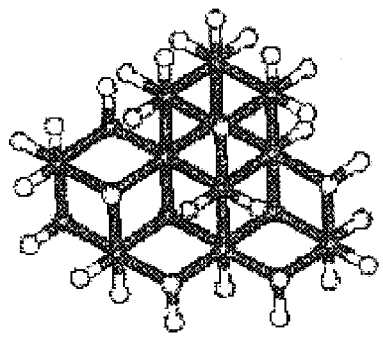
Figure 36:
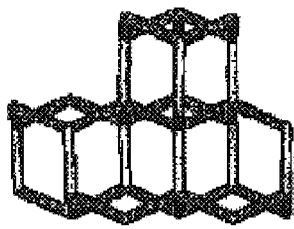
Figure 36:
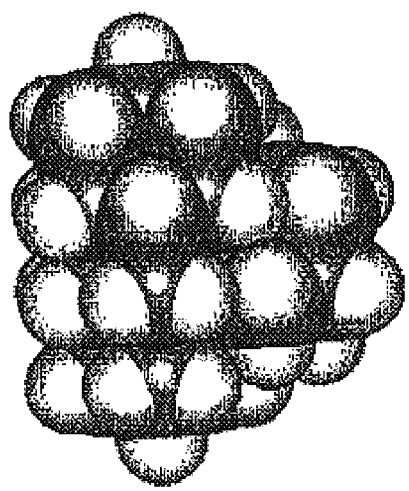
Figure 37:
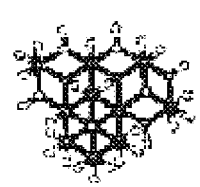
Figure 37:
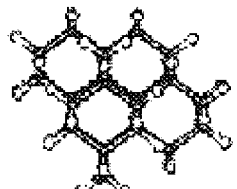
Figure 37:
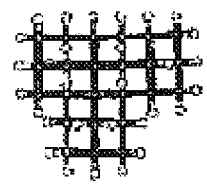
Figure 37:
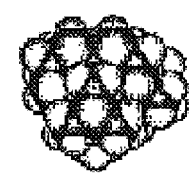
Figure 37:
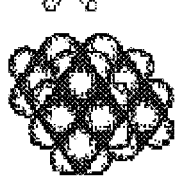
Figure 37:
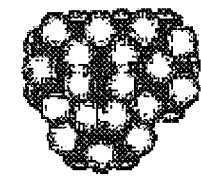
Figure 37:
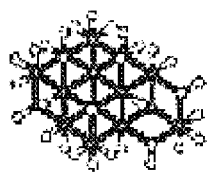
Figure 37:
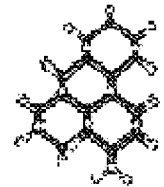
Figure 37:
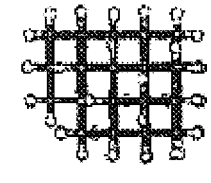
Figure 37:
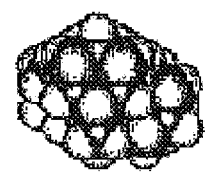
Figure 37:
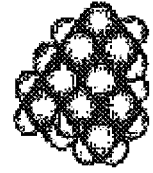
Figure 37:
Figure 37:
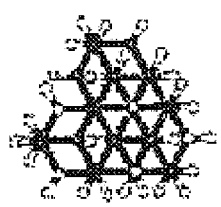
Figure 37:
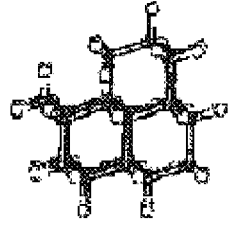
Figure 37:
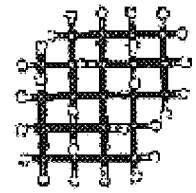
Figure 37:
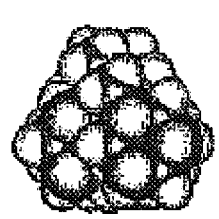
Figure 37:
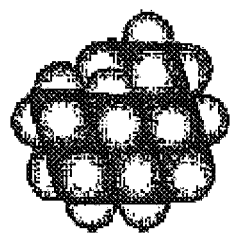
Figure 37:
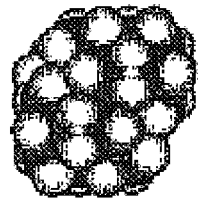
Figure 38:
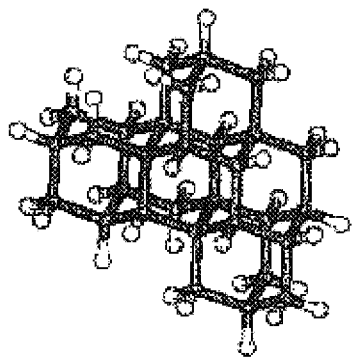
Figure 38:
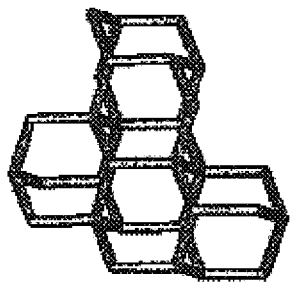
Figure 38:
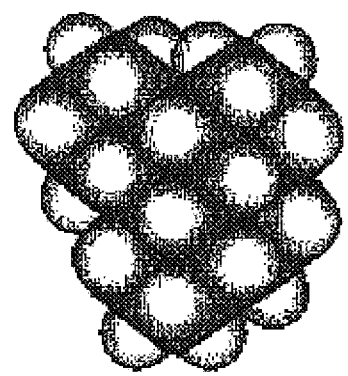
Figure 39:
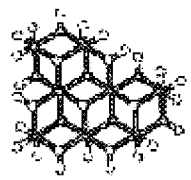
Figure 39:
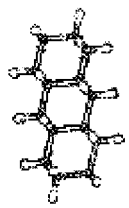
Figure 39:
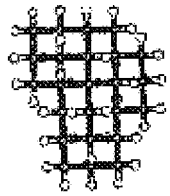
Figure 39:
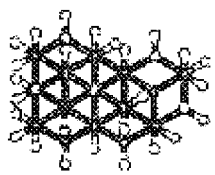
Figure 39:
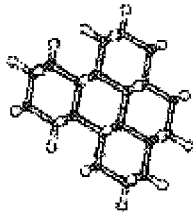
Figure 39:
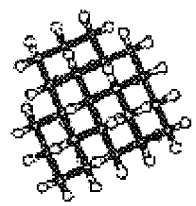
Figure 39:
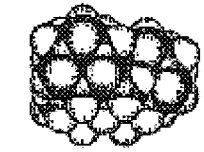
Figure 39:
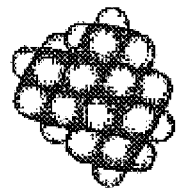
Figure 39:
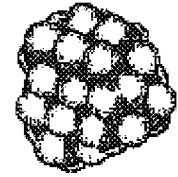
Figure 39:
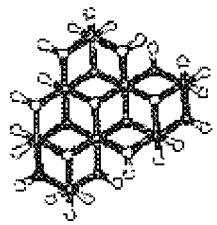
Figure 39:
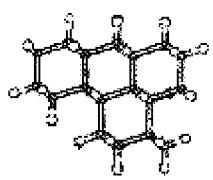
Figure 39:
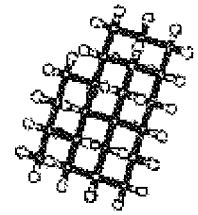
Figure 39:
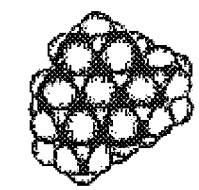
Figure 39:
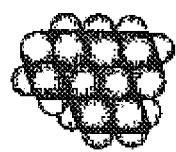
Figure 39:
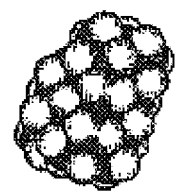
Figure 40:
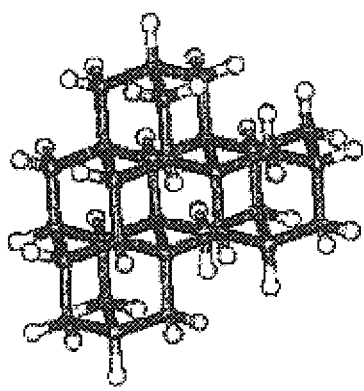
Figure 40:
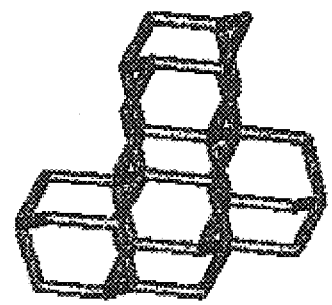
Figure 40:
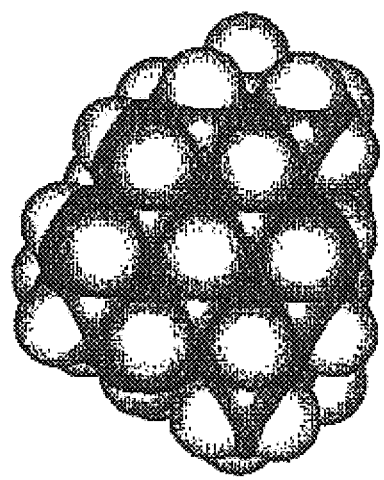
Figure 41:
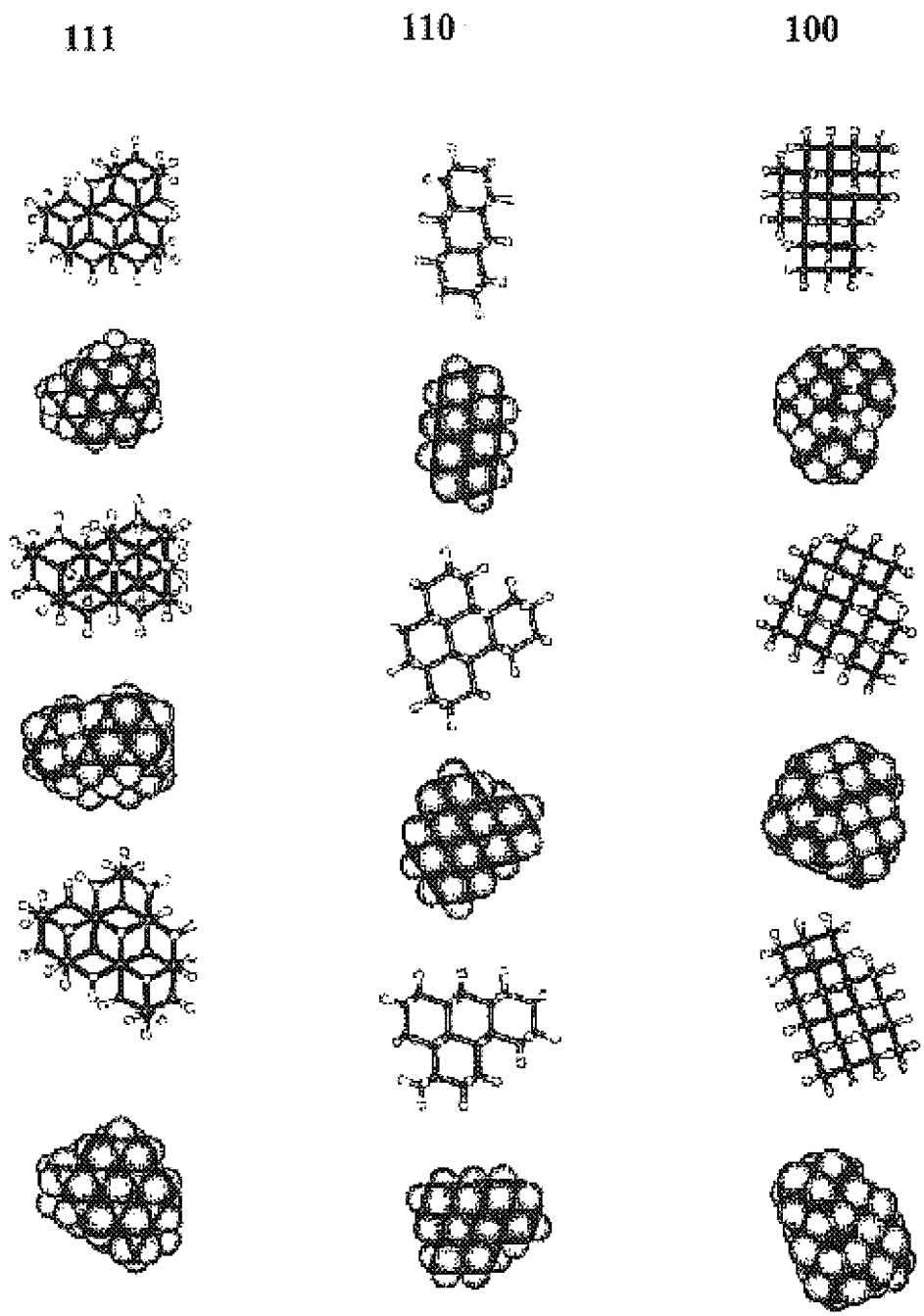
Figure 42:
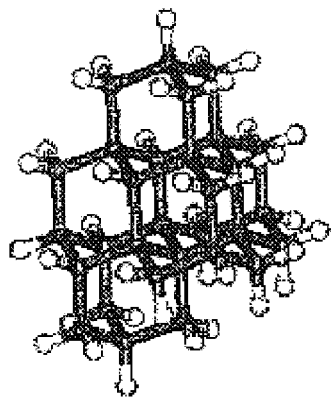
Figure 42:
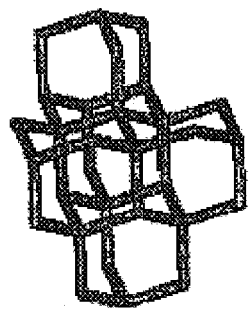
Figure 42:
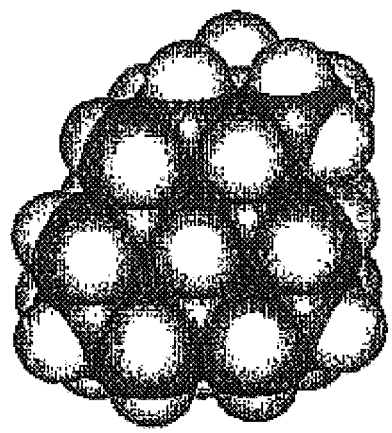
Figure 43:
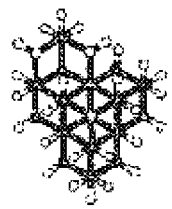
Figure 43:
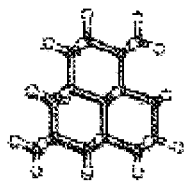
Figure 43:
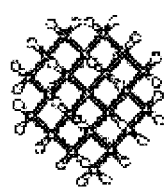
Figure 43:
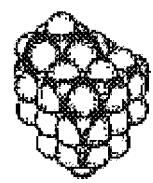
Figure 43:
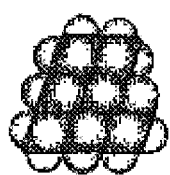
Figure 43:
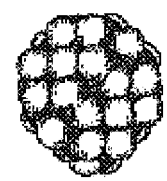
Figure 43:
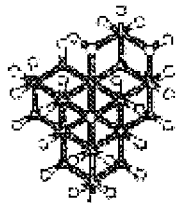
Figure 43:
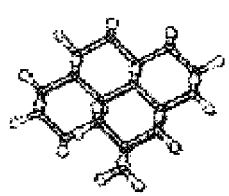
Figure 43:
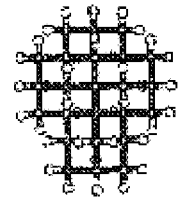
Figure 43:
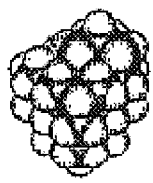
Figure 43:
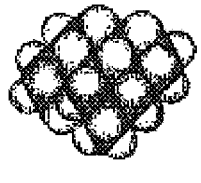
Figure 43:
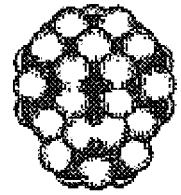
Figure 43:
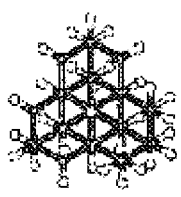
Figure 43:
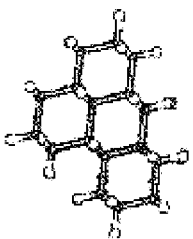
Figure 43:
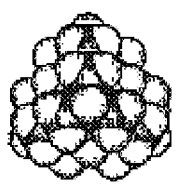
Figure 43:
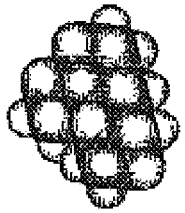
Figure 44:
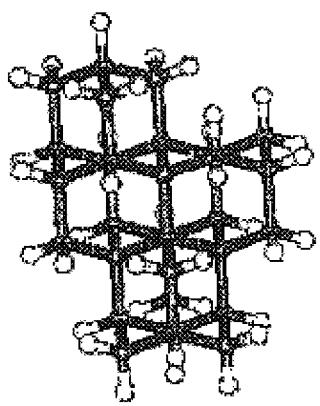
Figure 44:
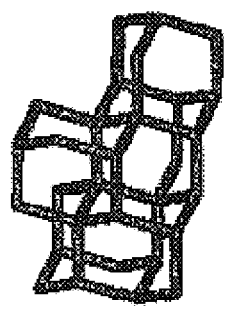
Figure 44:
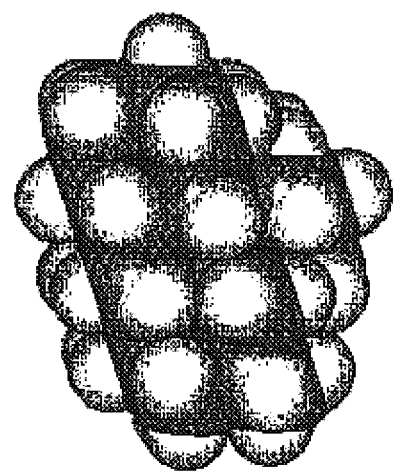
Figure 45:
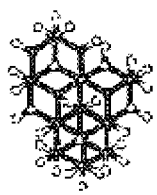
Figure 45:
Figure 45:
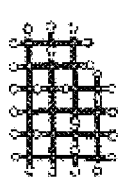
Figure 45:
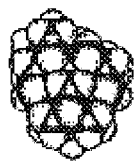
Figure 45:
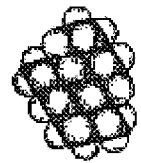
Figure 45:
Figure 45:
Figure 45:
Figure 45:
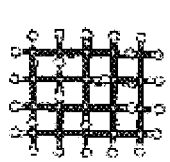
Figure 45:
Figure 45:
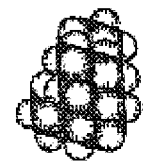
Figure 45:
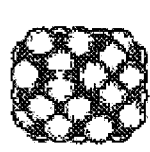
Figure 45:
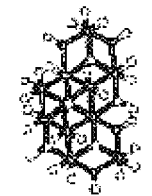
Figure 45:
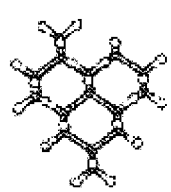
Figure 45:
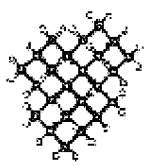
Figure 45:
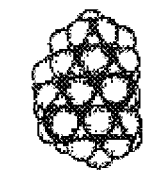
Figure 45:
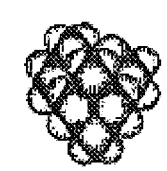
Figure 45:
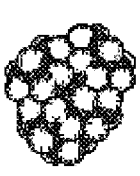
Figure 46:
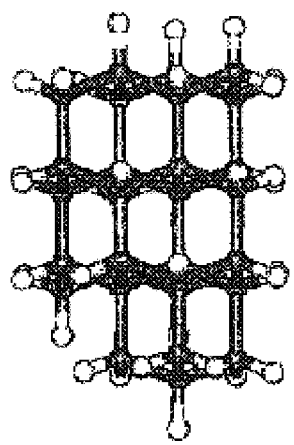
Figure 46:
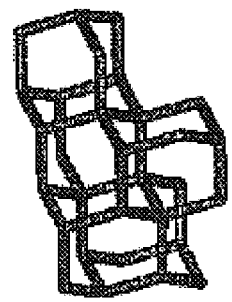
Figure 46:
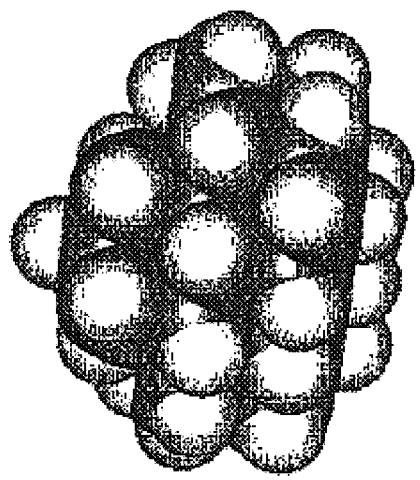
Figure 47:
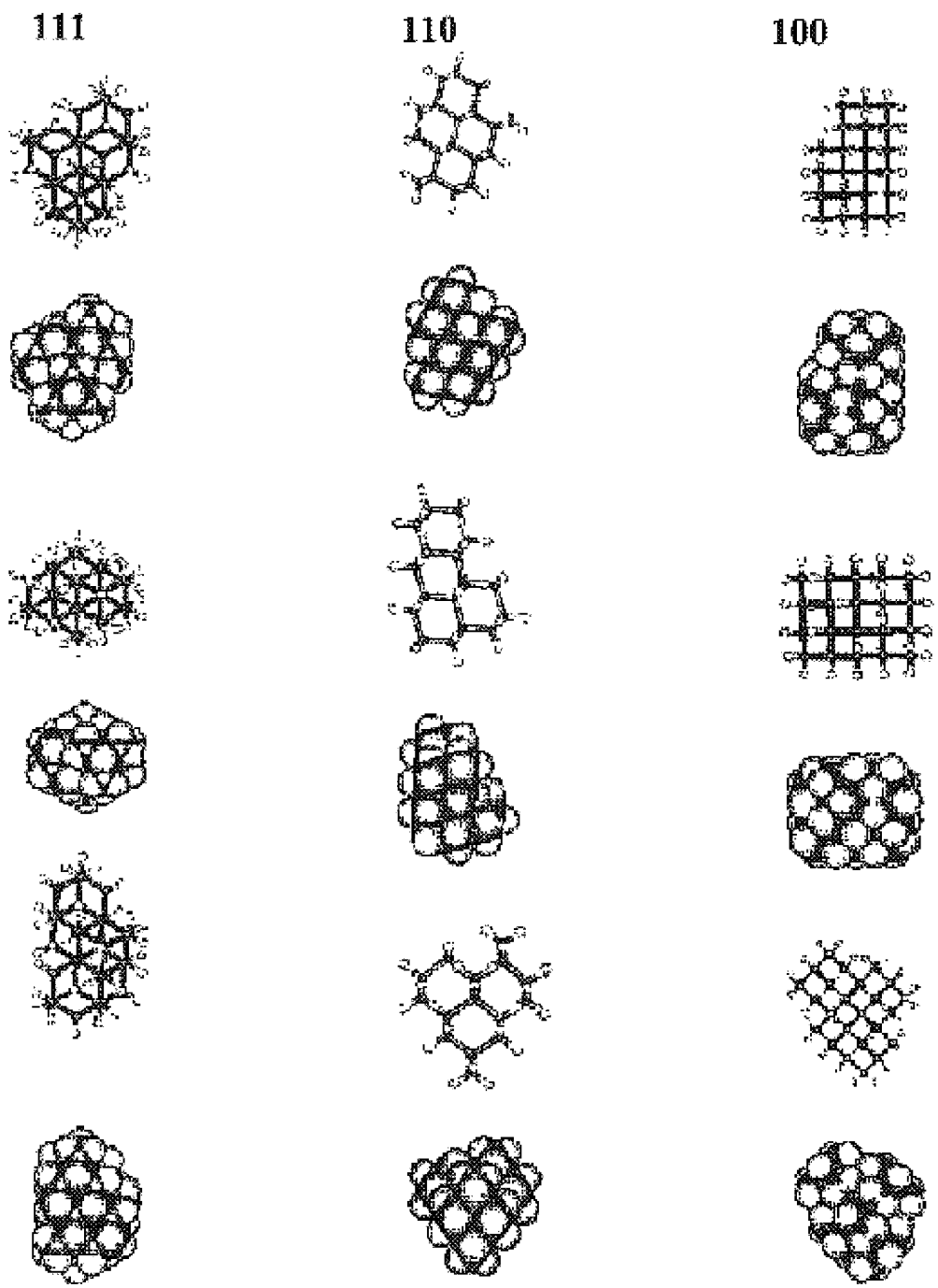
Figure 48:
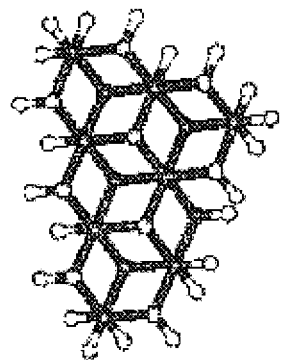
Figure 48:
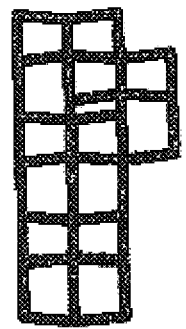
Figure 48:
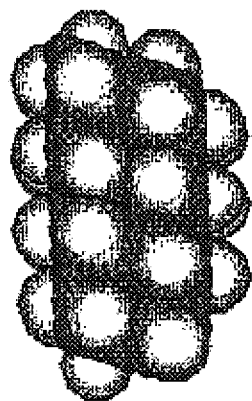
Figure 49:
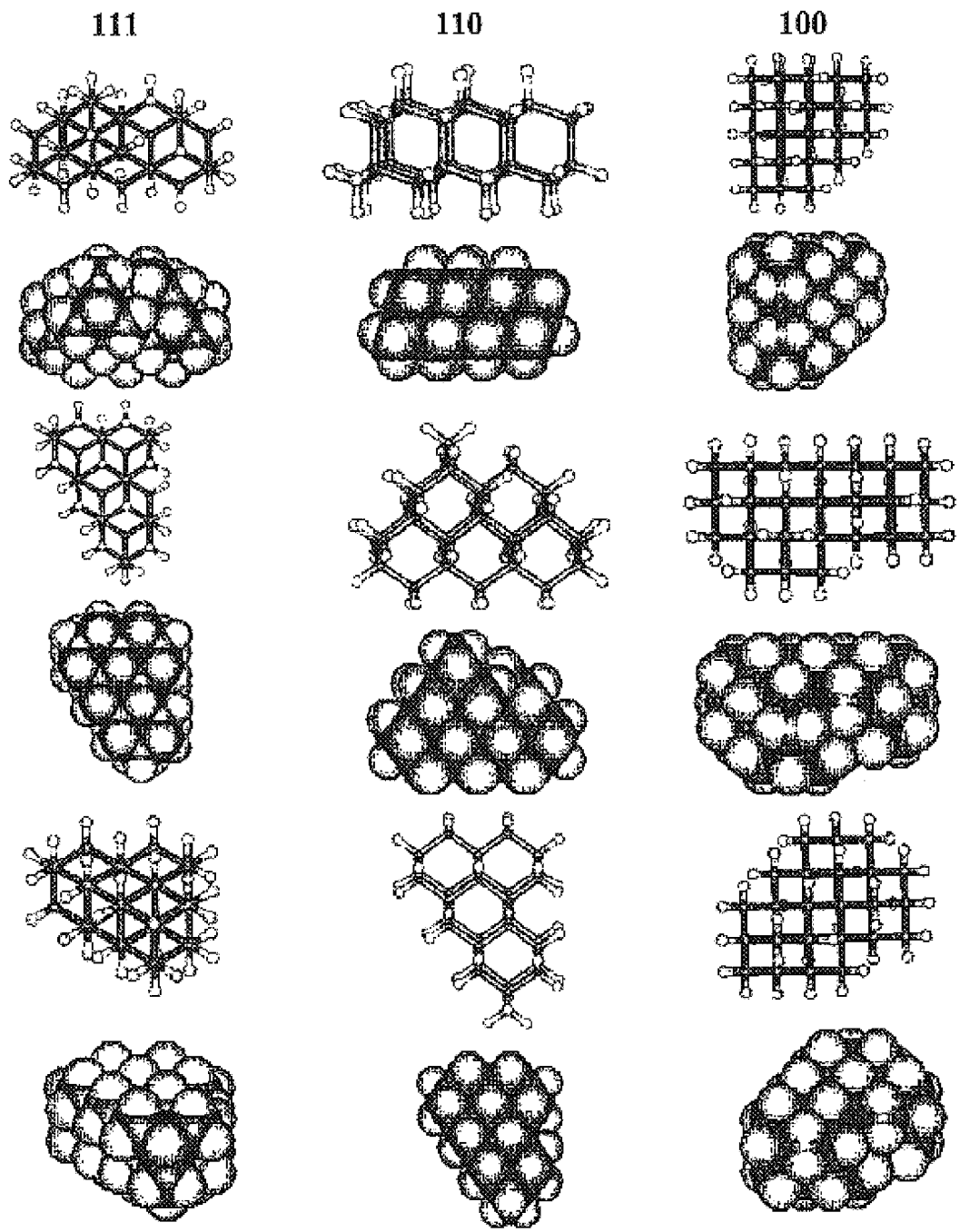
Figure 50:
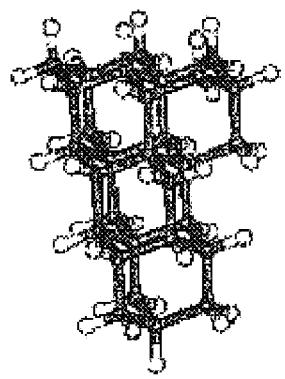
Figure 50:
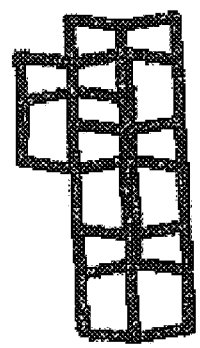
Figure 50:
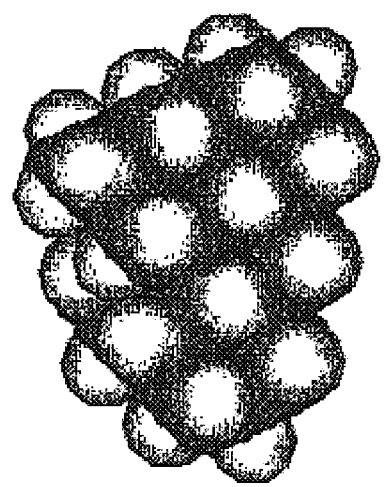
Figure 51:
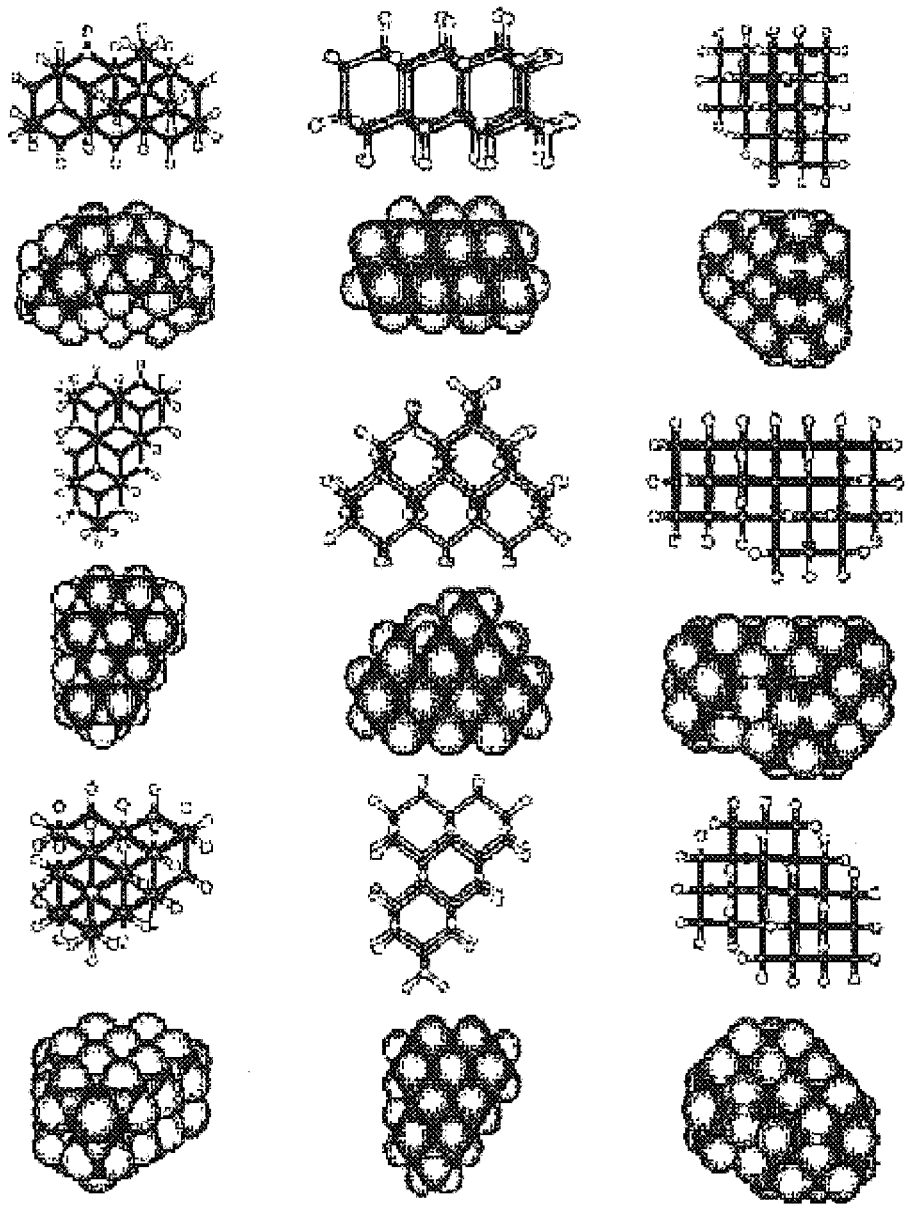
Figure 52:
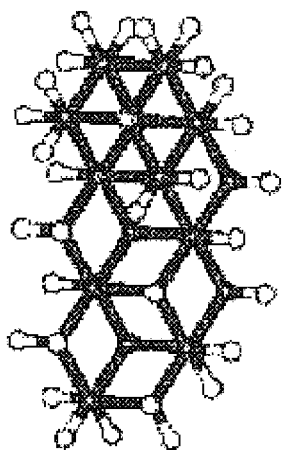
Figure 52:
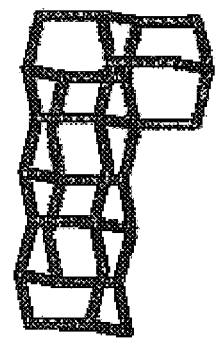
Figure 52:
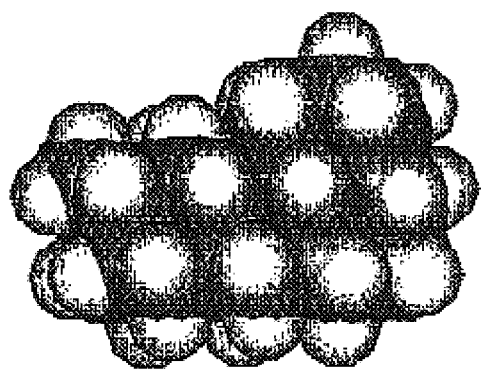
Figure 53:
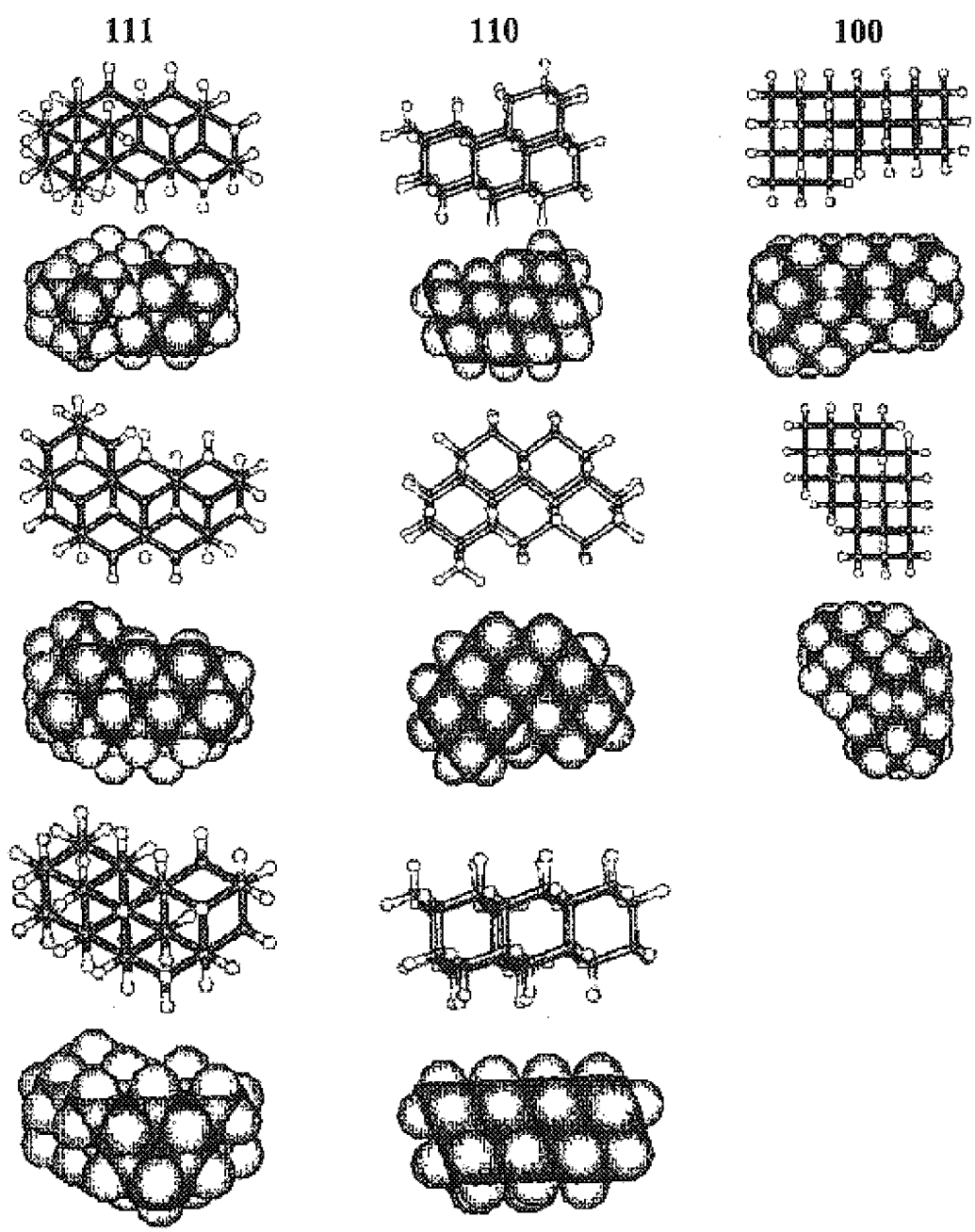
Figure 54:
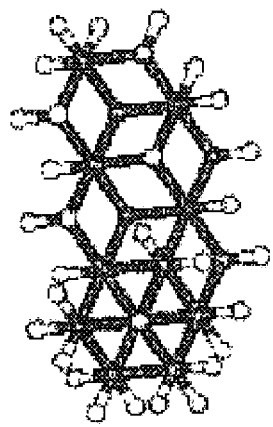
Figure 54:
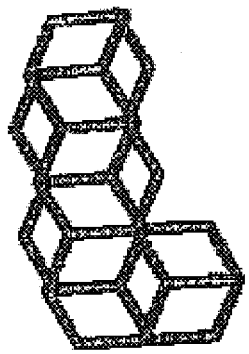
Figure 54:
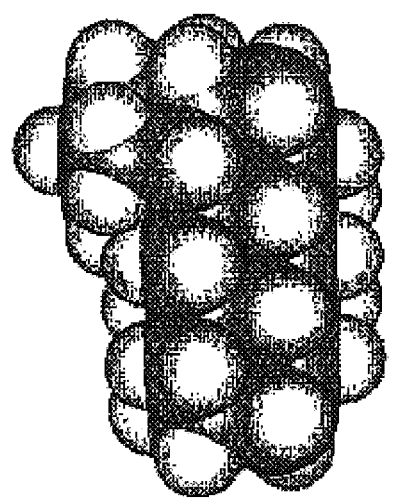
Figure 55:
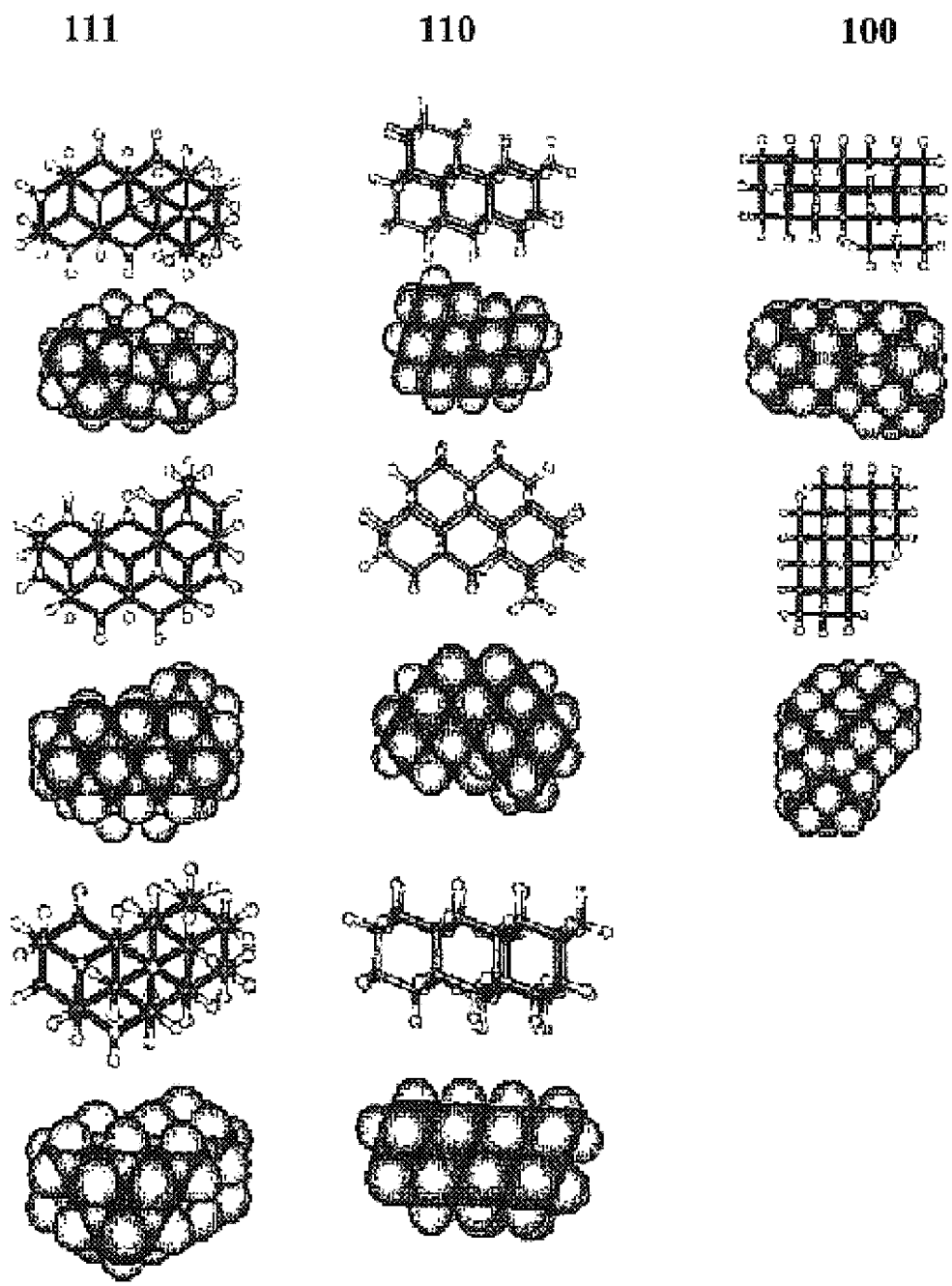
Figure 56:
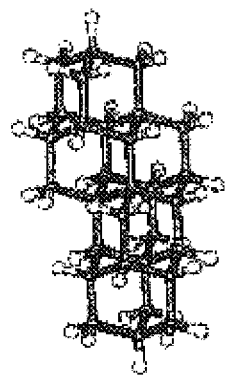
Figure 56:
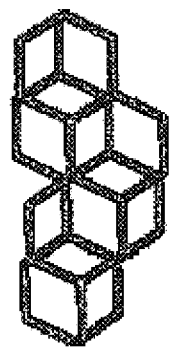
Figure 56:
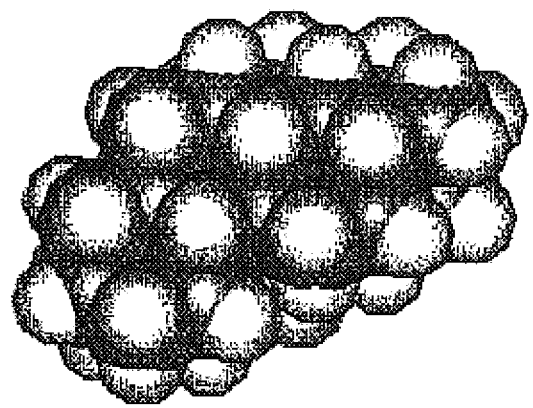
Figure 57:
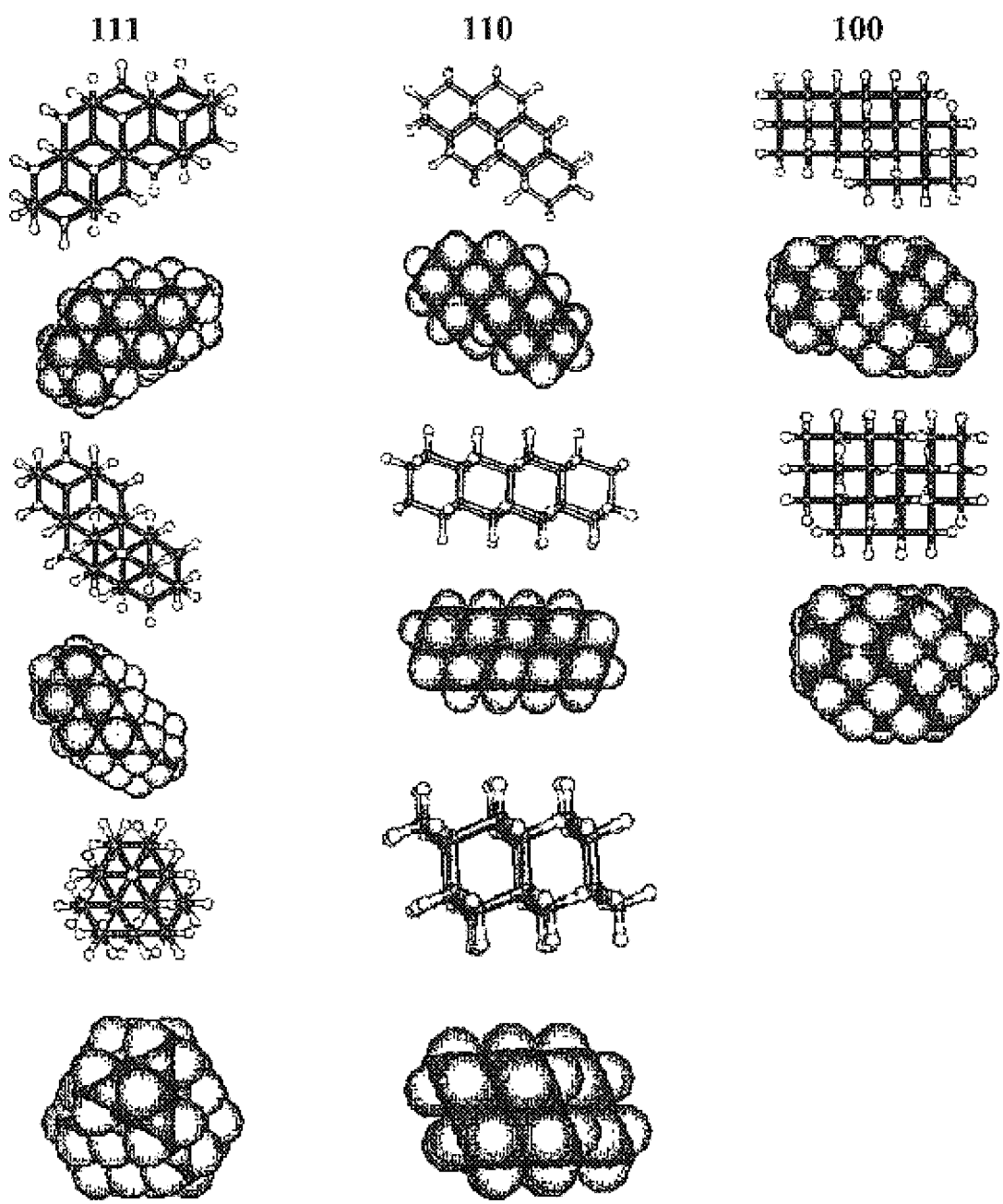
Figure 58:
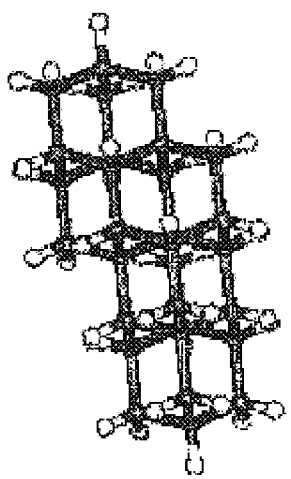
Figure 58:
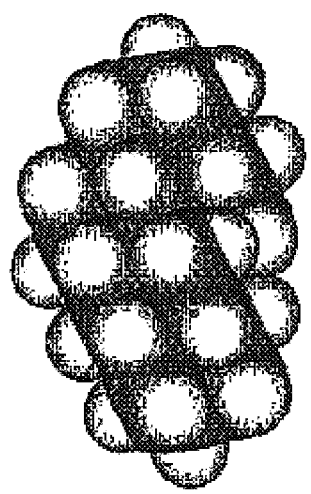
Figure 59:
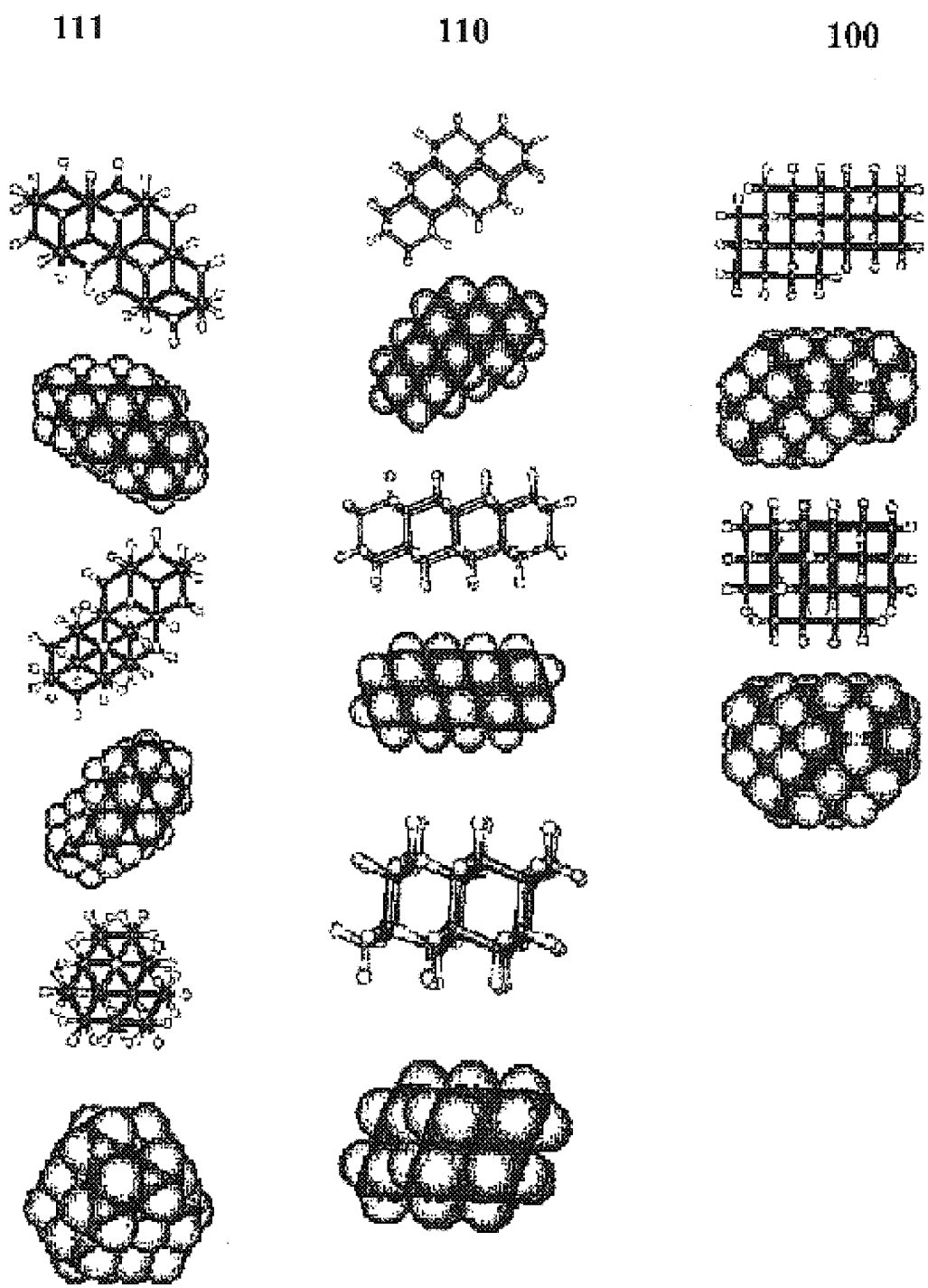
Figure 60:
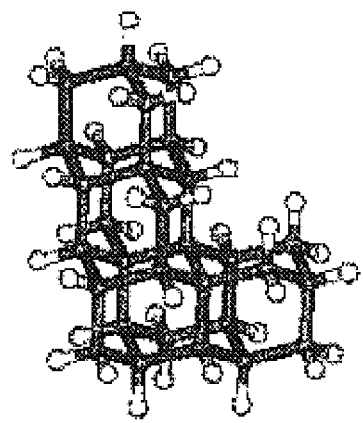
Figure 60:
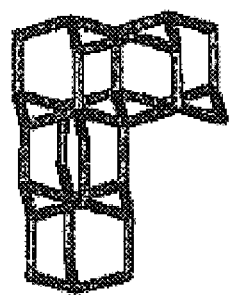
Figure 60:
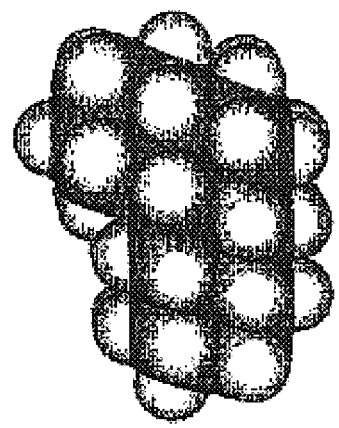
Figure 61:
Figure 61:
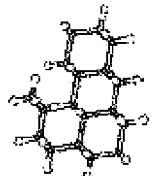
Figure 61:
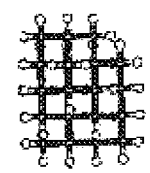
Figure 61:
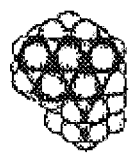
Figure 61:
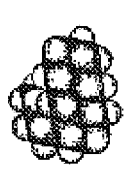
Figure 61:
Figure 61:
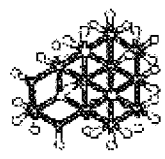
Figure 61:
Figure 61:
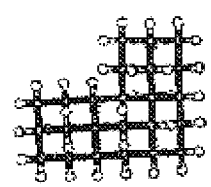
Figure 61:
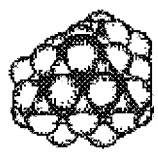
Figure 61:
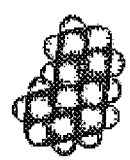
Figure 61:
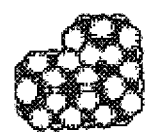
Figure 61:
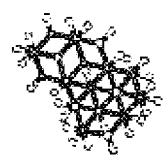
Figure 61:
Figure 61:
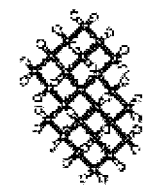
Figure 61:
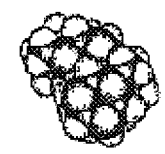
Figure 61:
Figure 61:
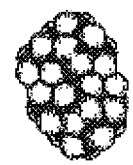
Figure 62:
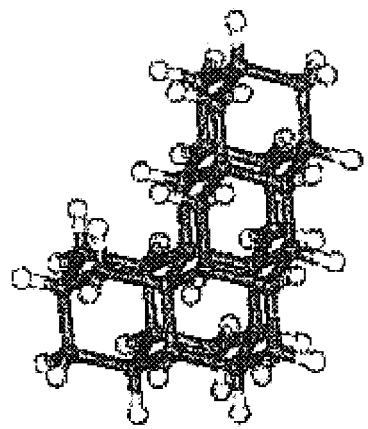
Figure 62:
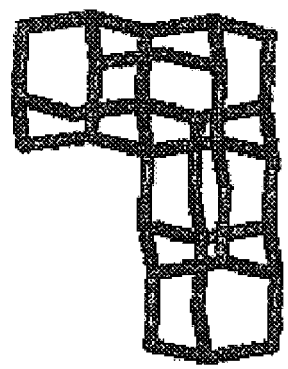
Figure 62:
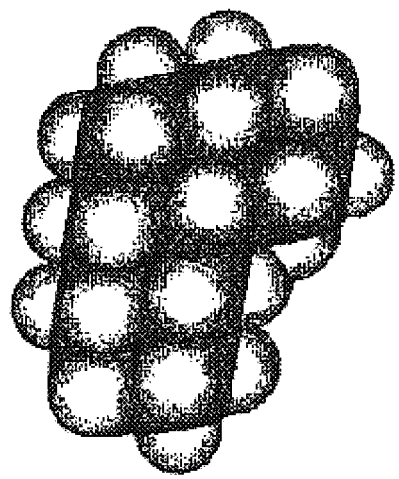
Figure 63:
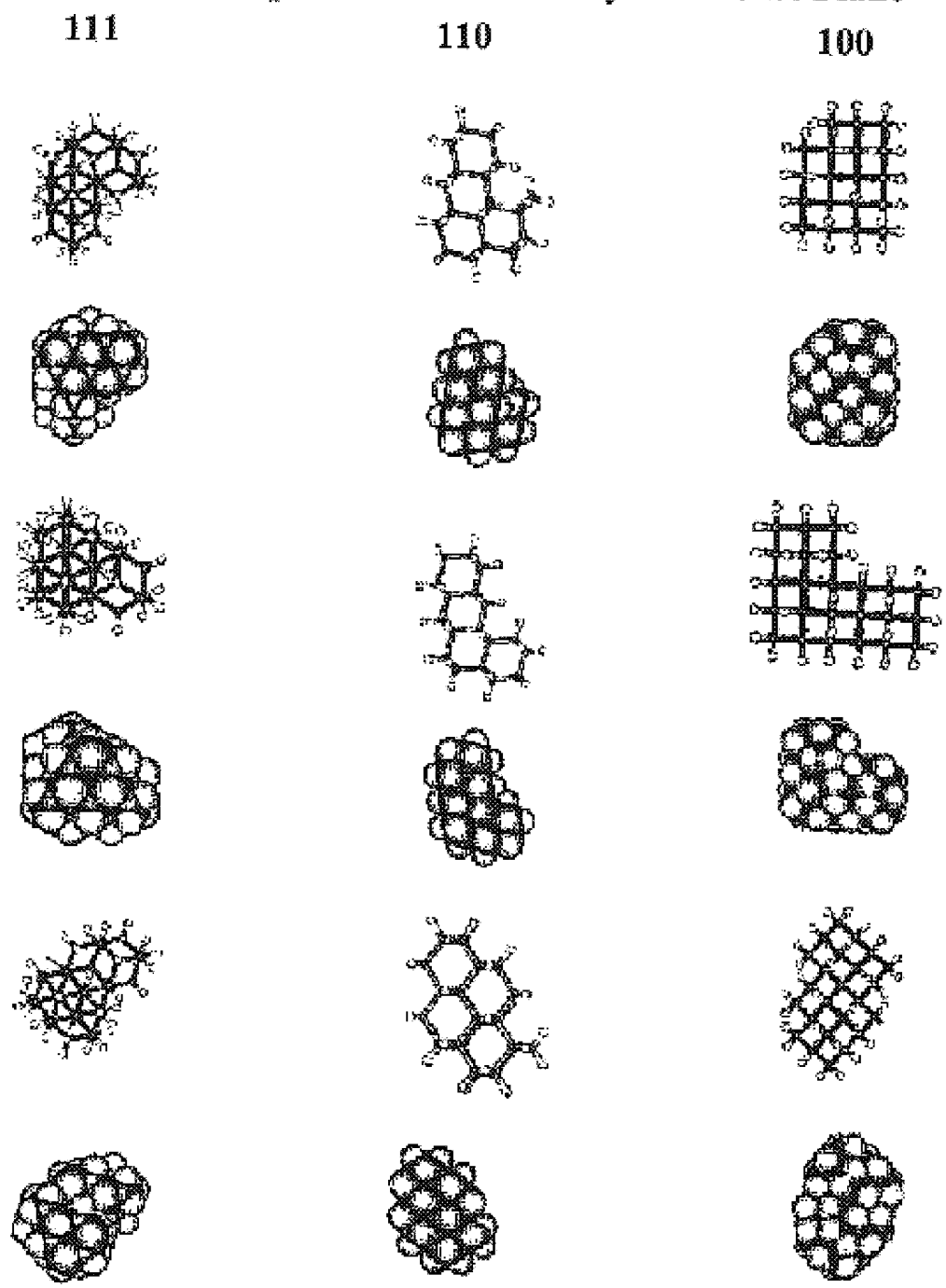
Figure 64:
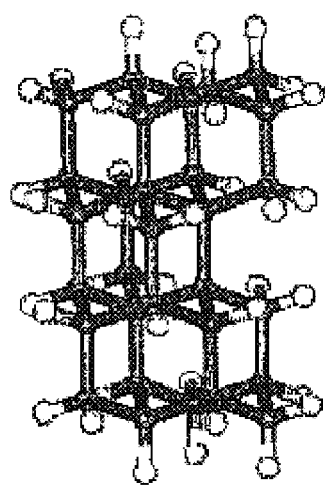
Figure 64:
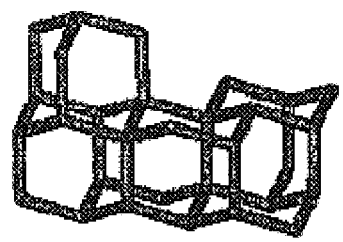
Figure 64:
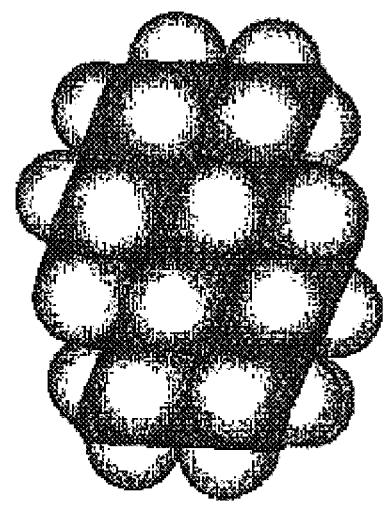
Figure 65:
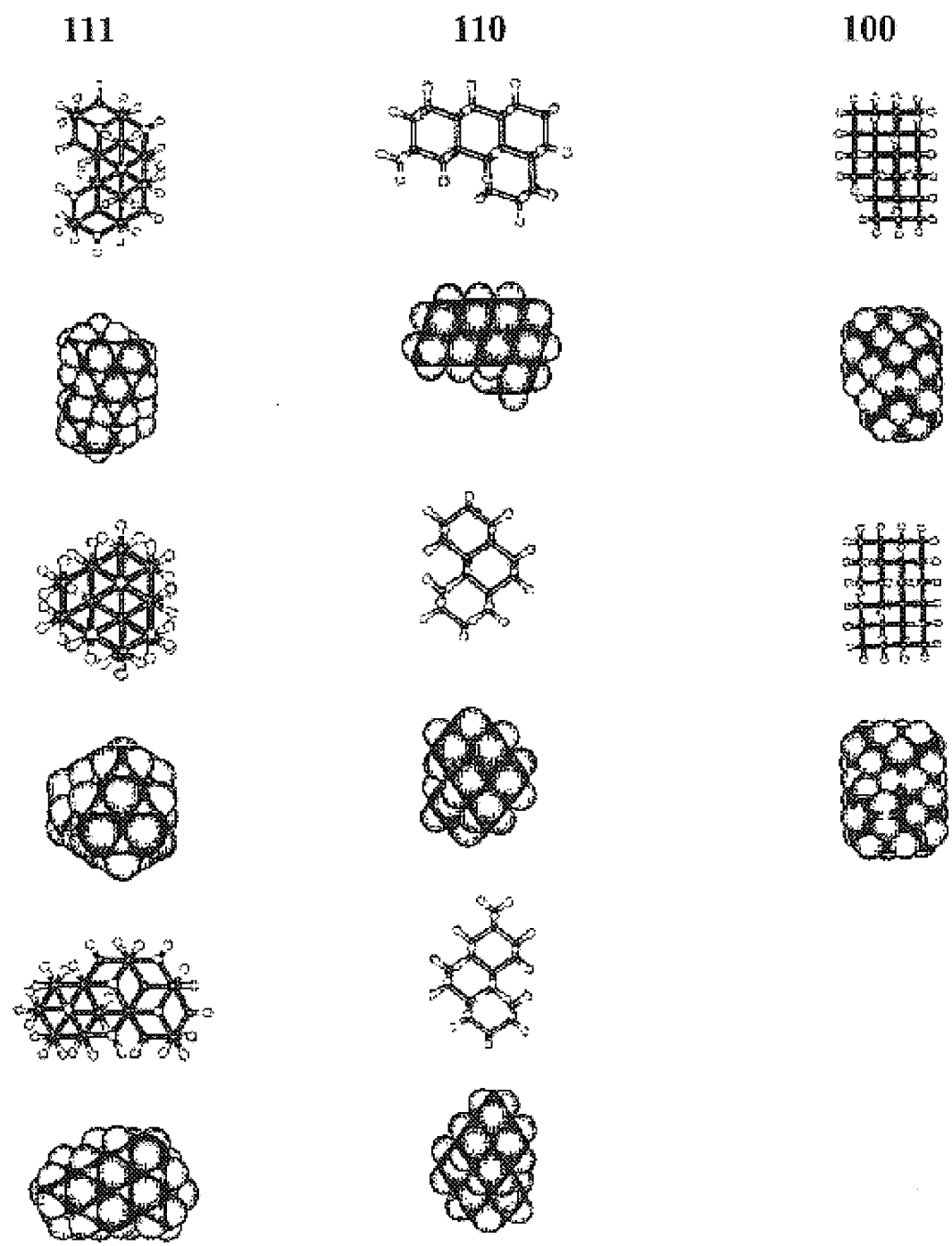
Figure 66:
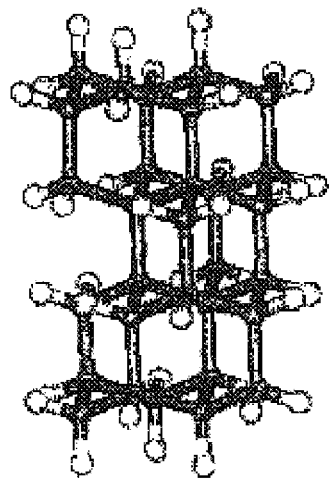
Figure 66:
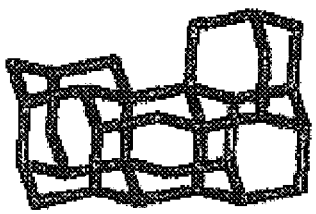
Figure 66:
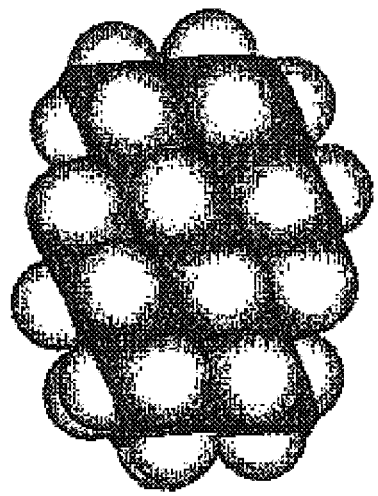
Figure 67:
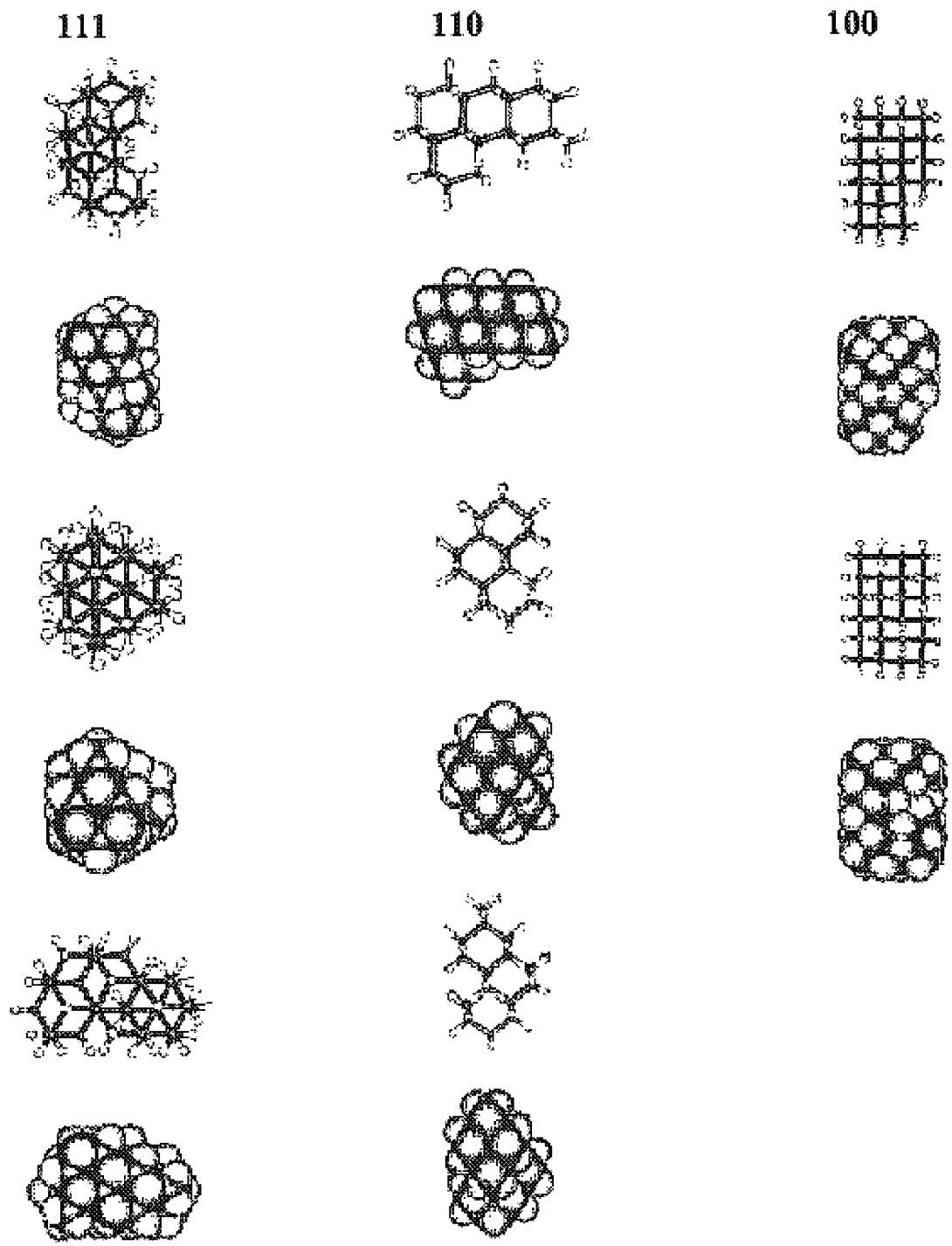
Figure 68:
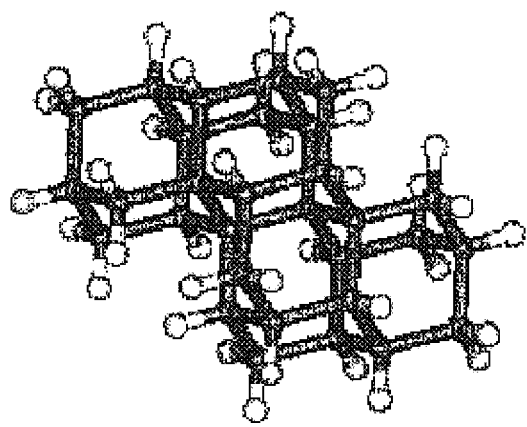
Figure 68:
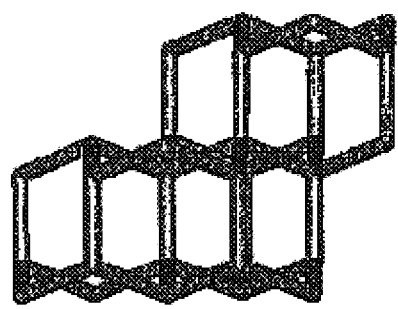
Figure 68:
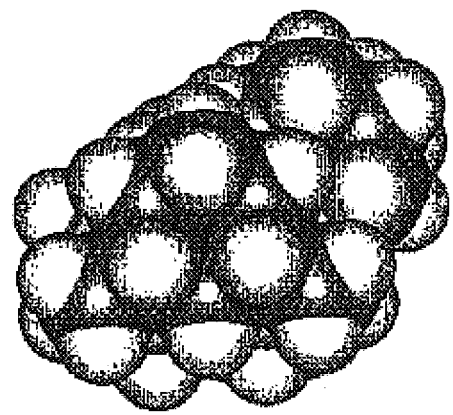
Figure 69:
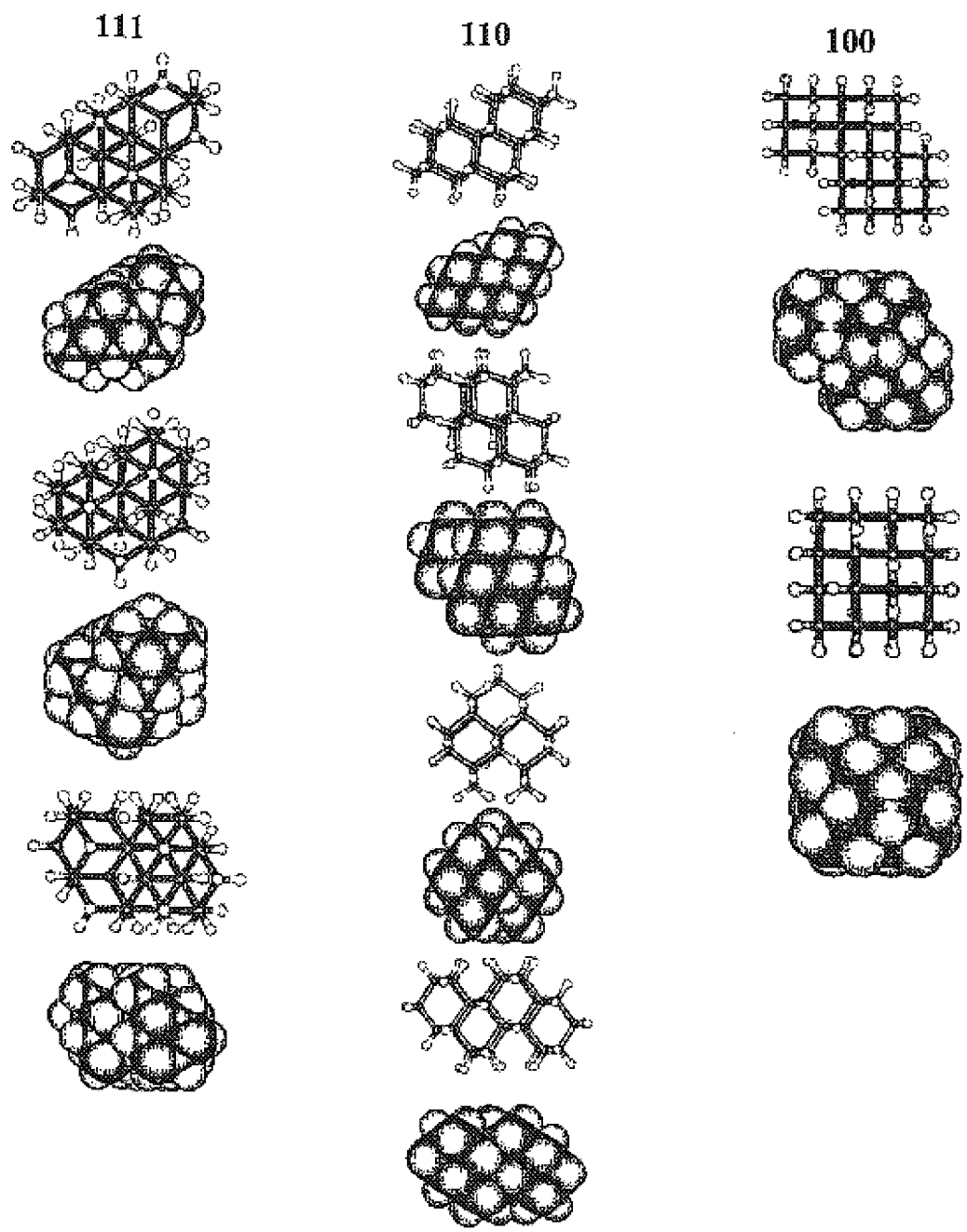
Figure 70:
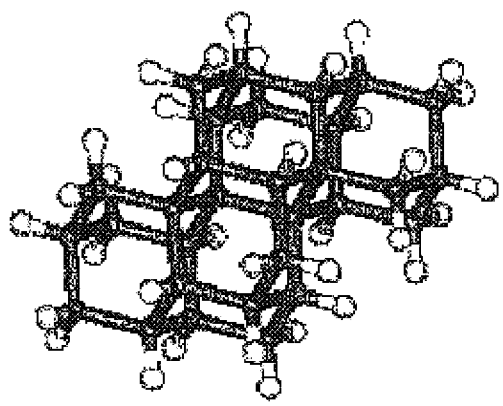
Figure 70:
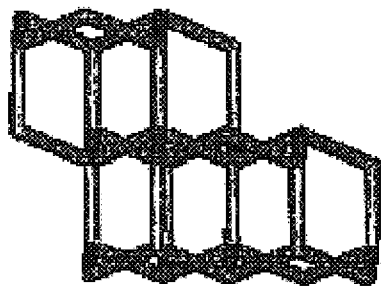
Figure 70:
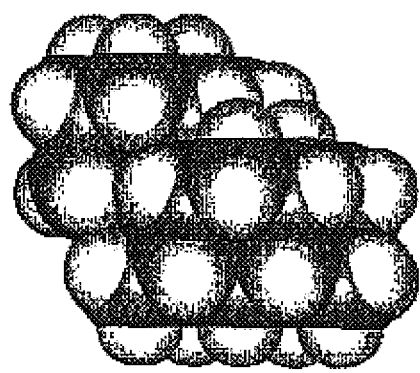
Figure 71:
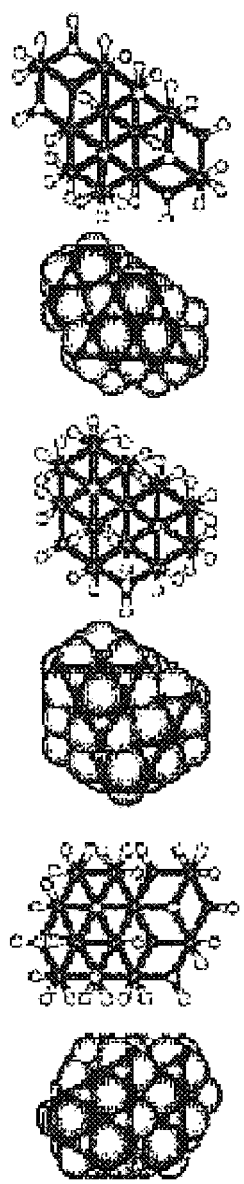
Figure 71:
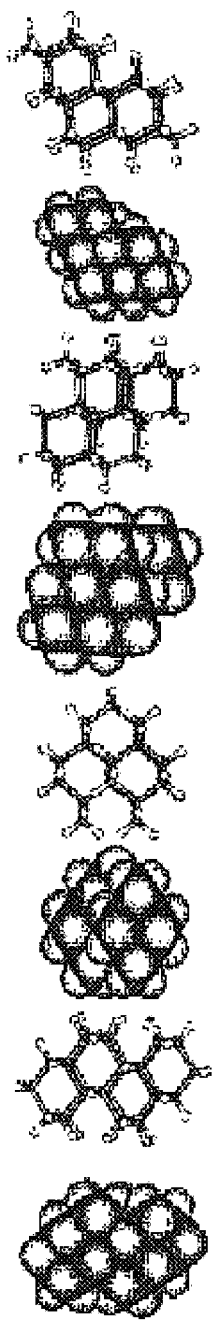
Figure 71:
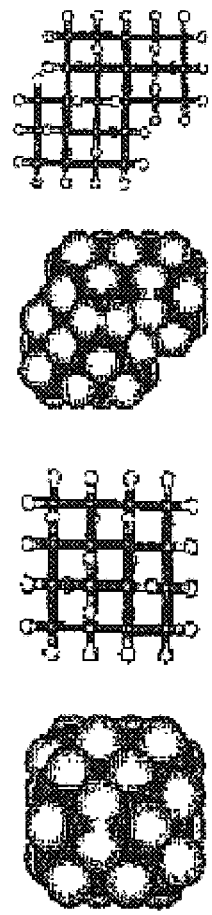
Figure 72:
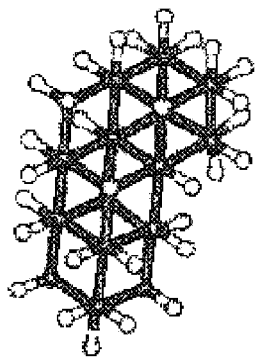
Figure 72:
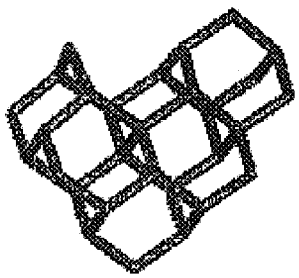
Figure 72:
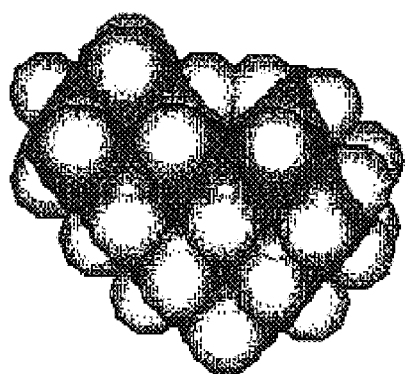
Figure 73:
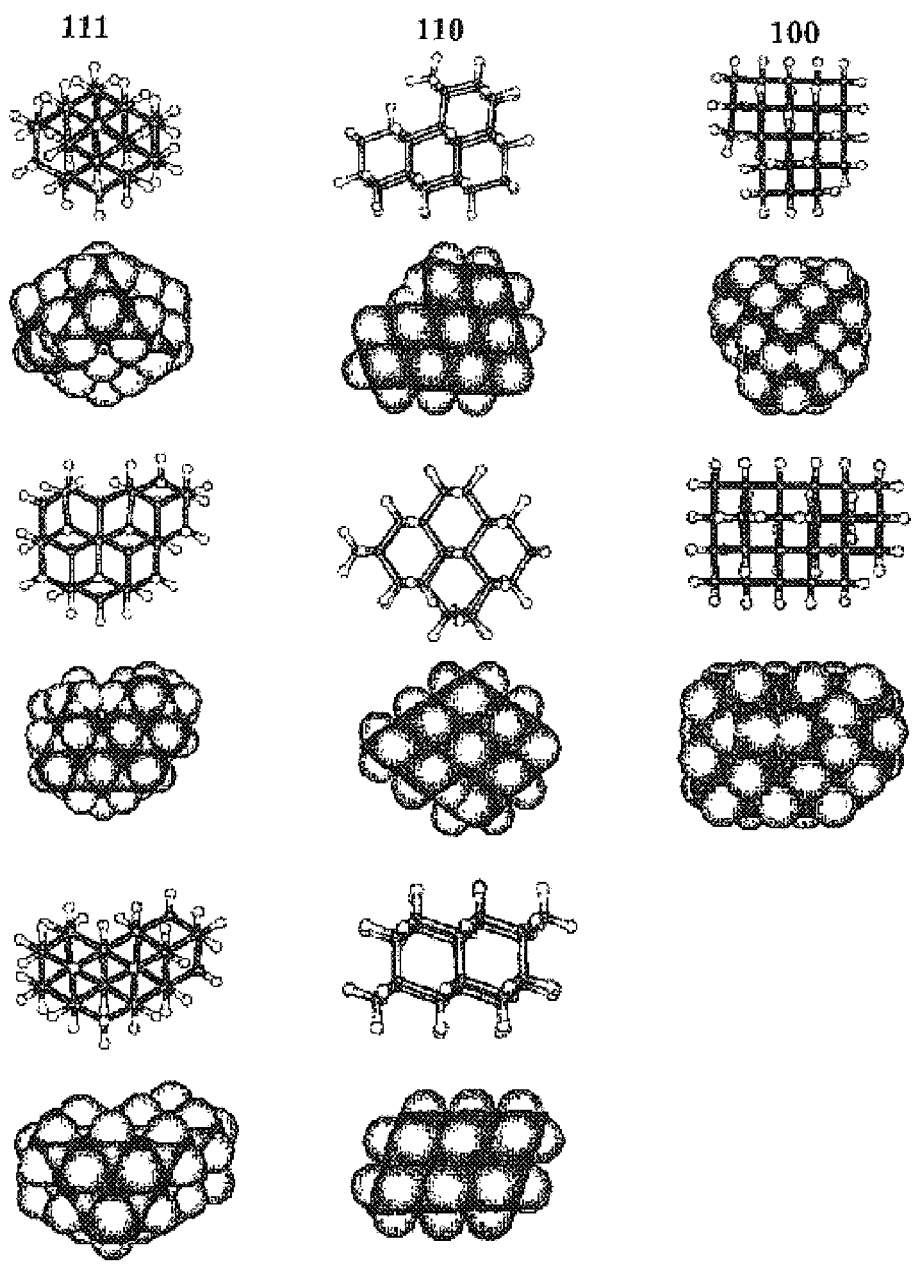
Figure 74:
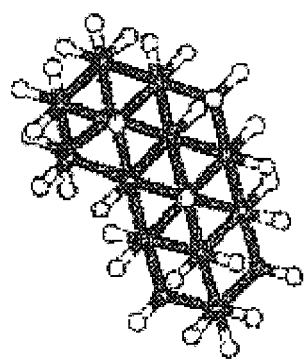
Figure 74:
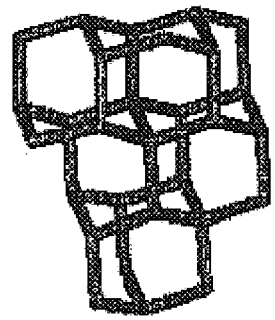
Figure 74:
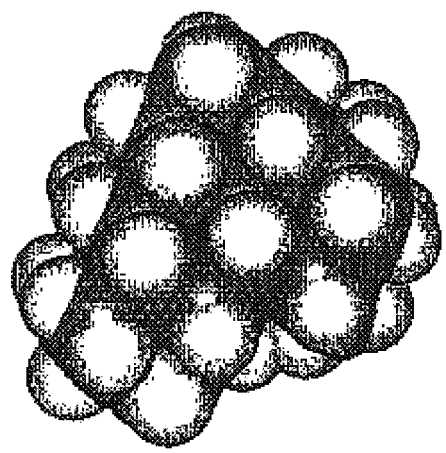
Figure 75:
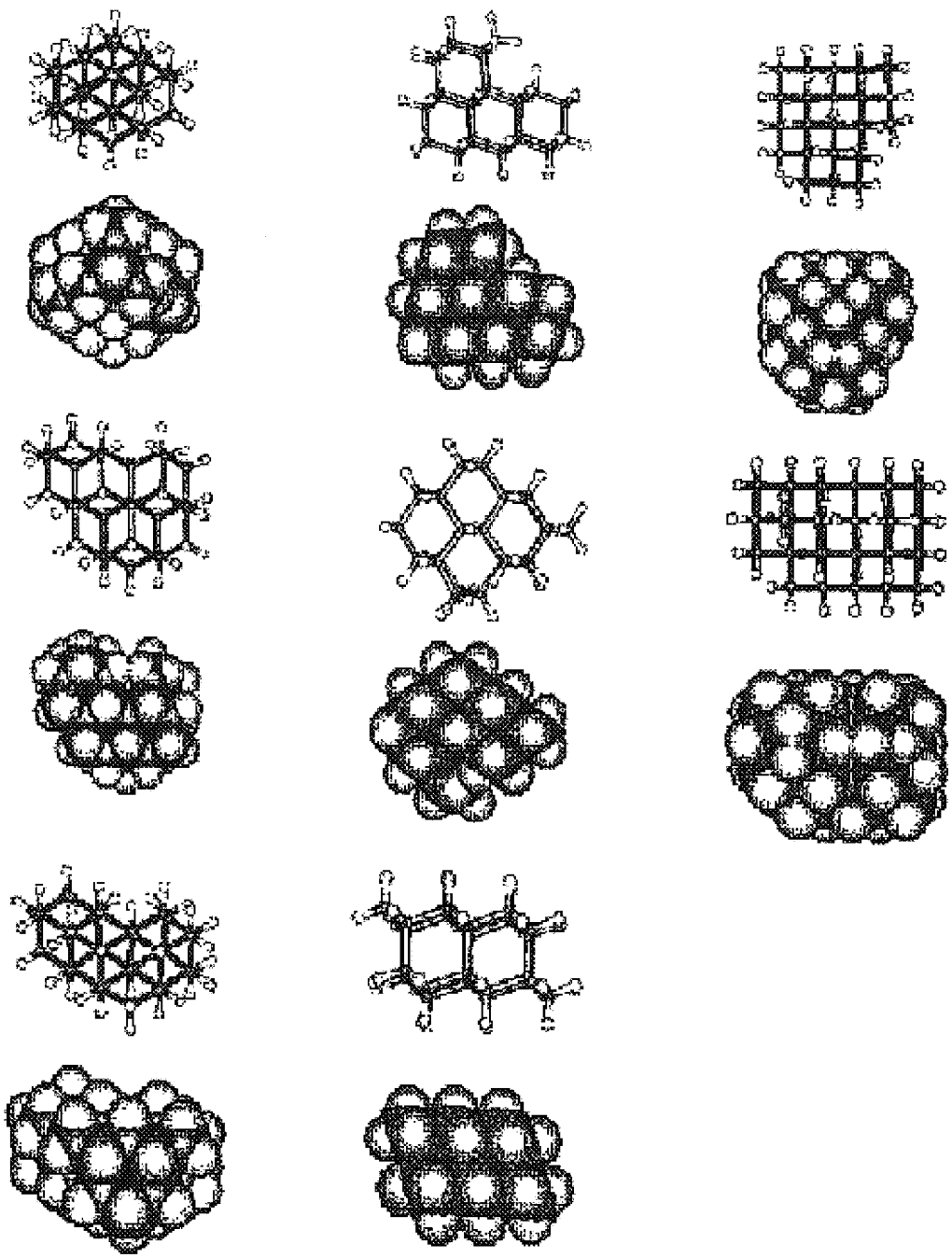
Figure 76:
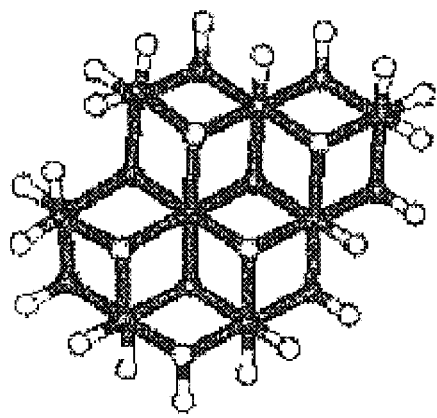
Figure 76:
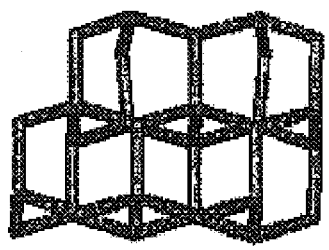
Figure 76:
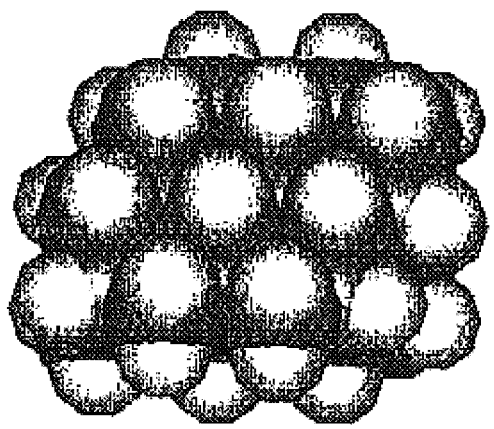
Figure 77:
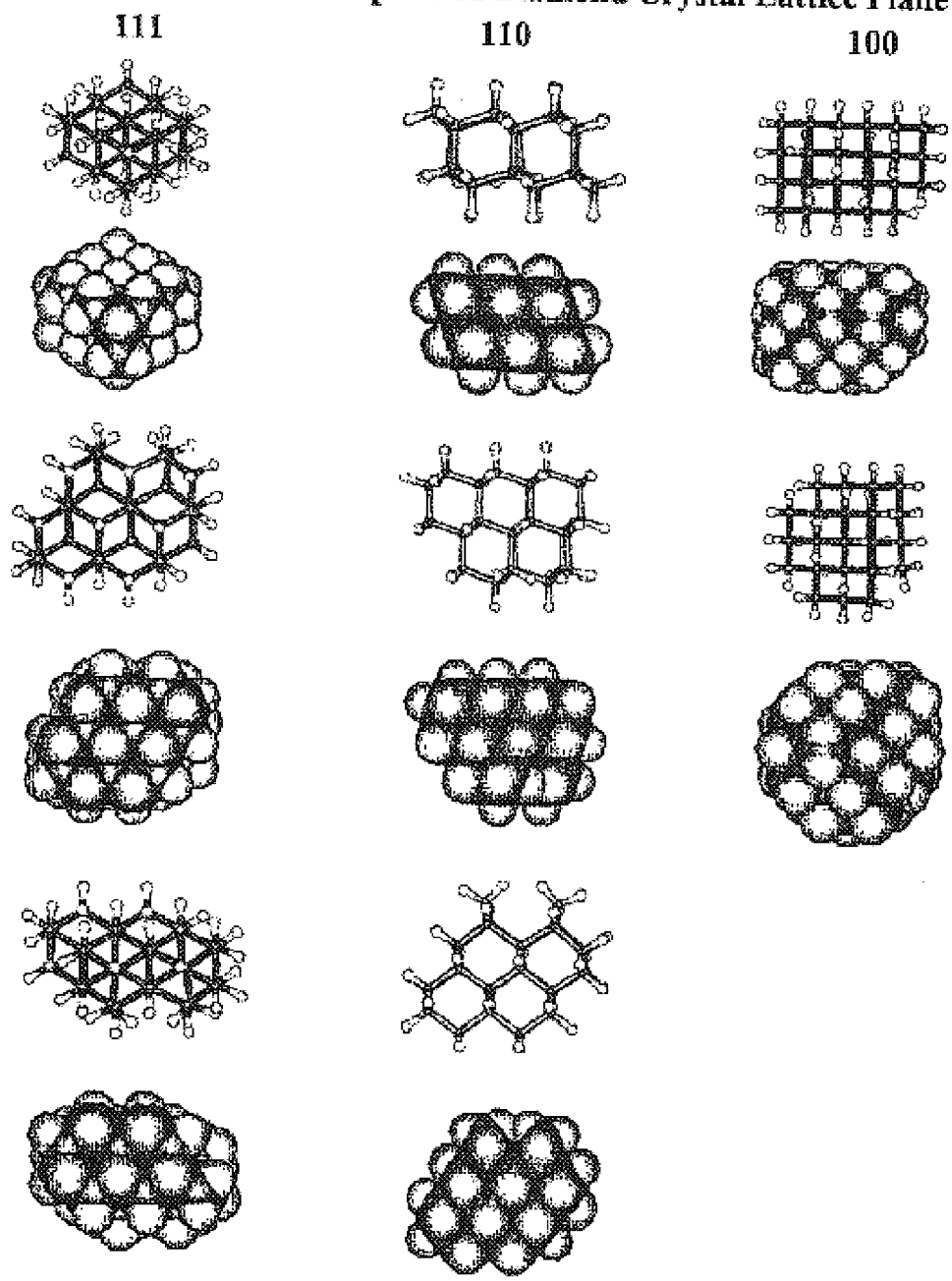
Figure 78:
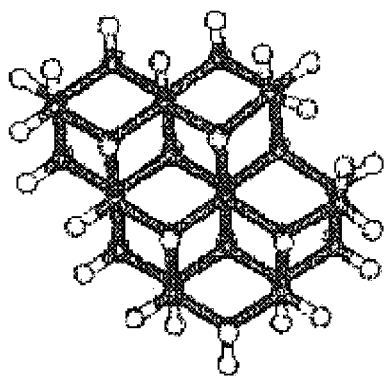
Figure 78:
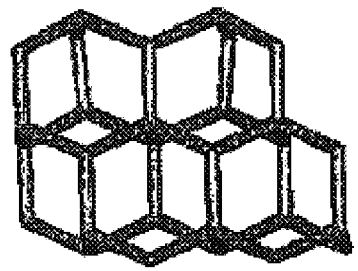
Figure 78:
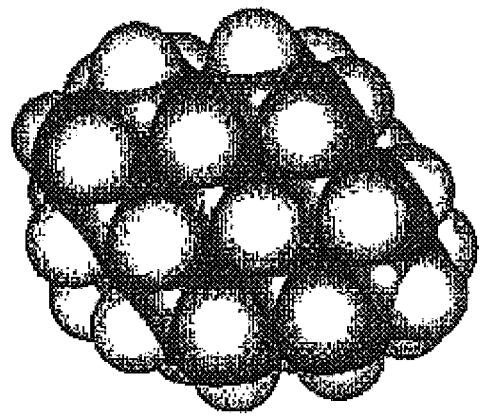
Figure 79:
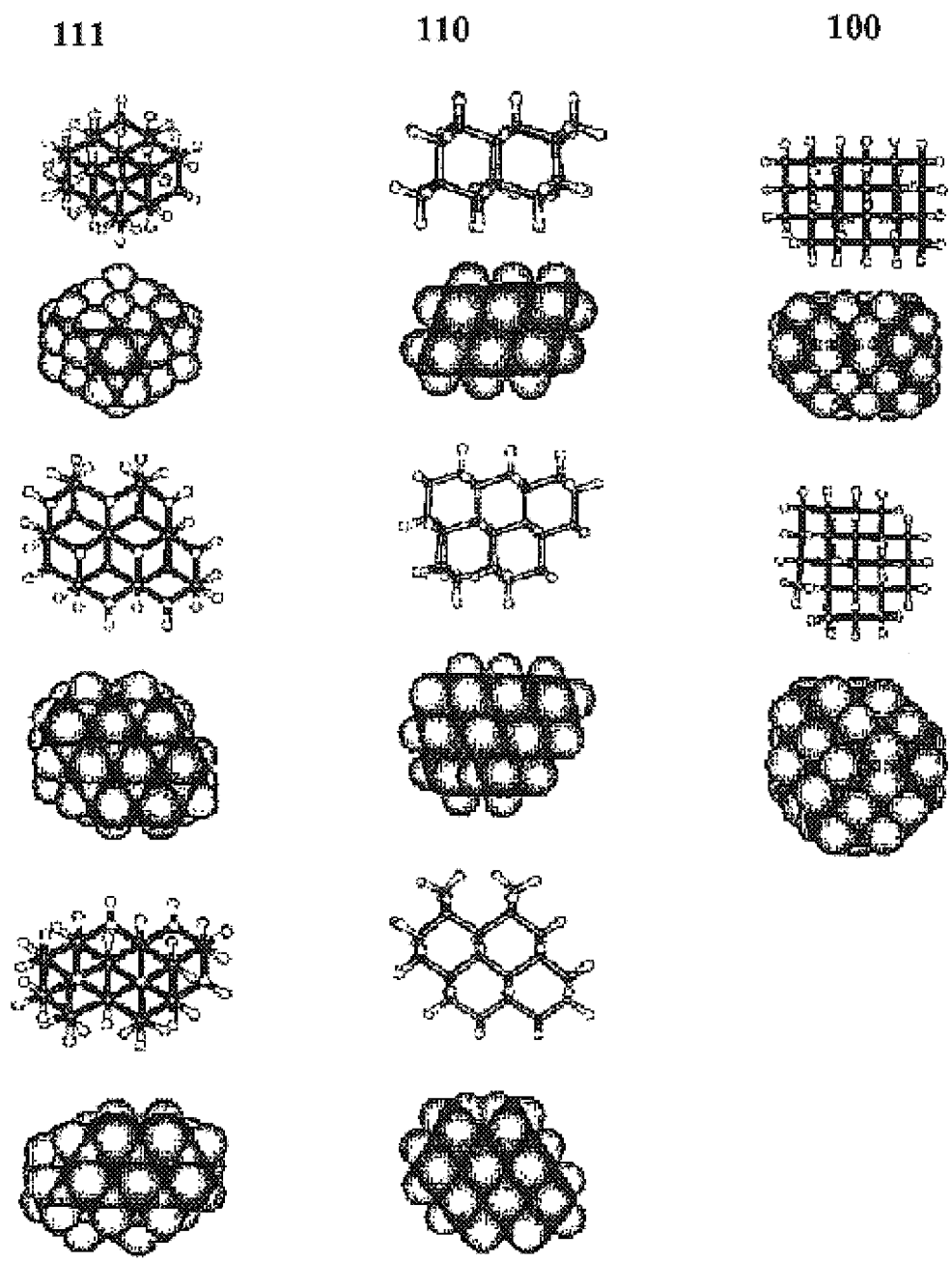
Figure 80:
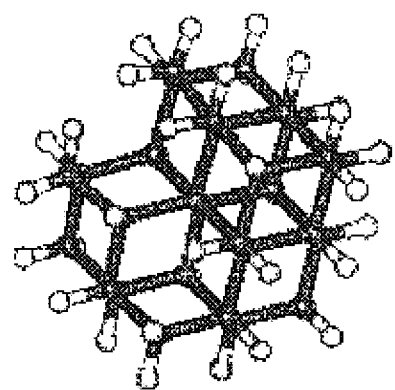
Figure 80:
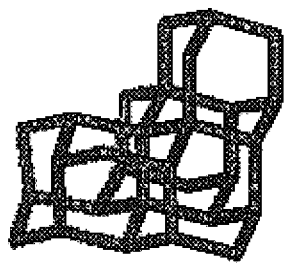
Figure 80:
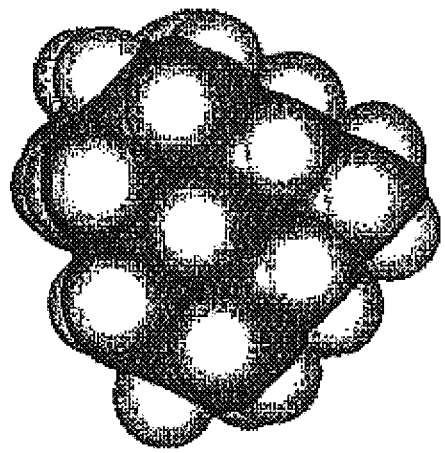
Figure 81:
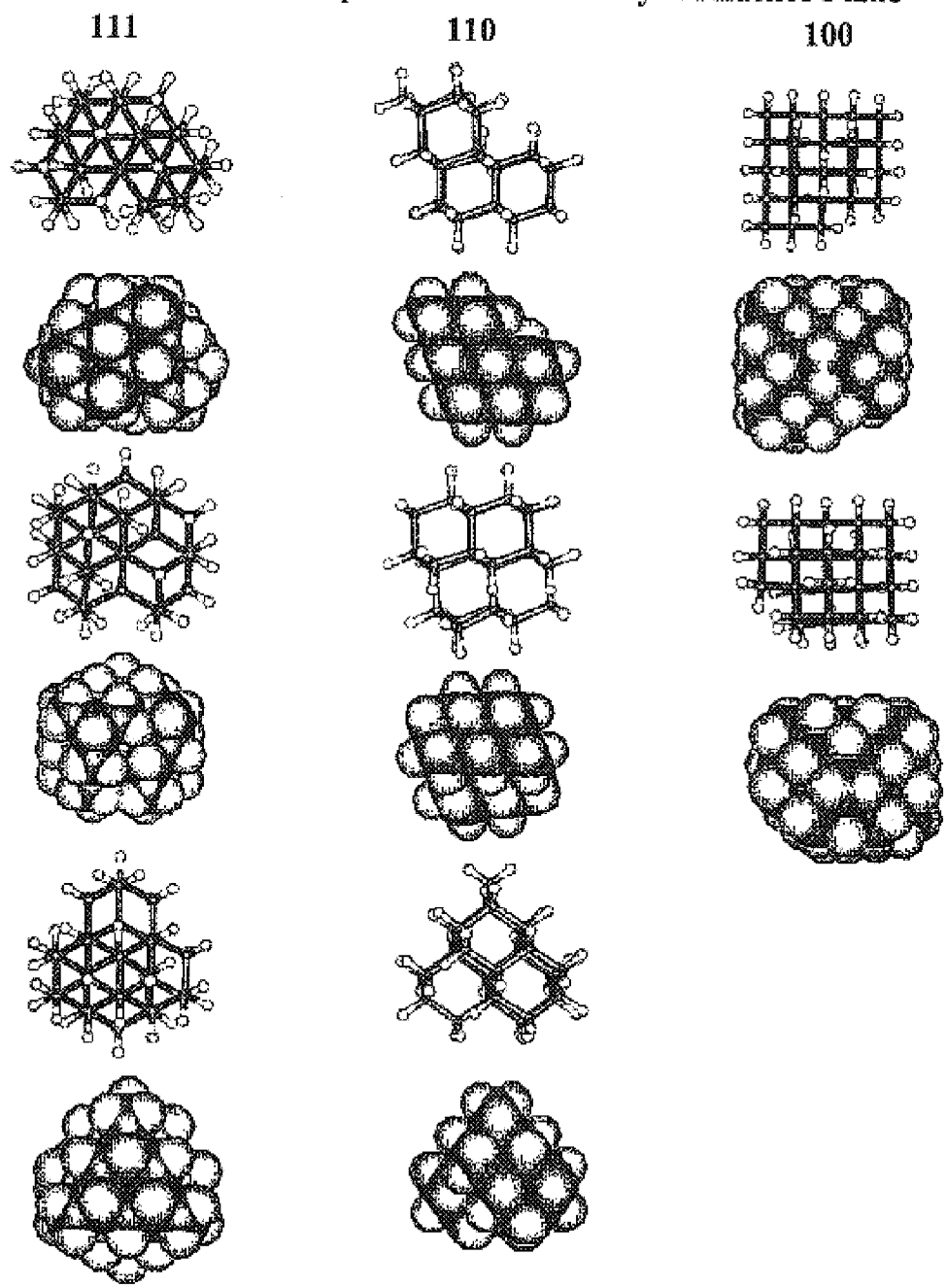
Figure 82:
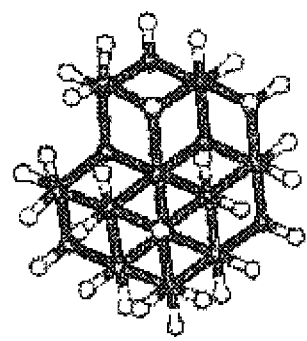
Figure 82:
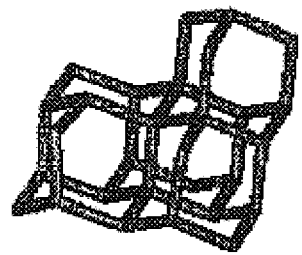
Figure 82:
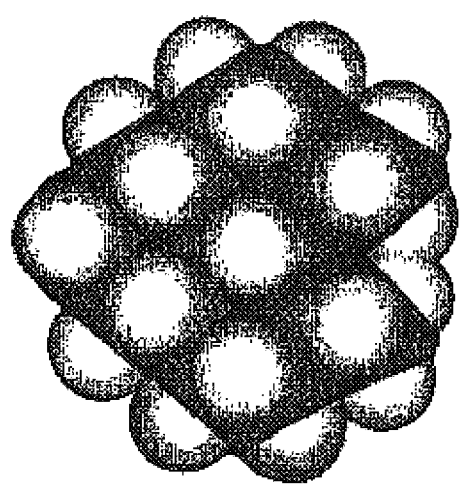
Figure 83:
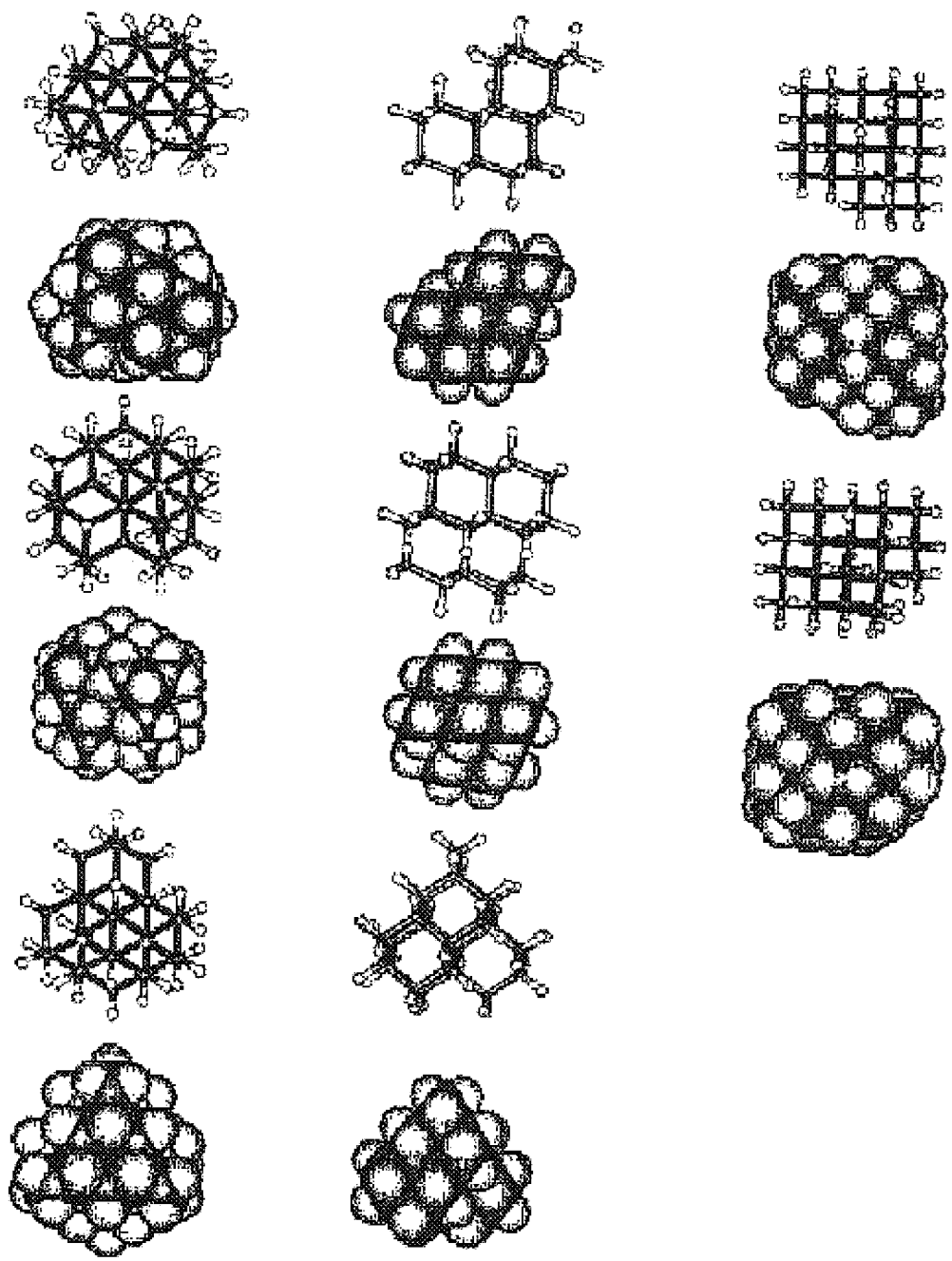
Figure 84:
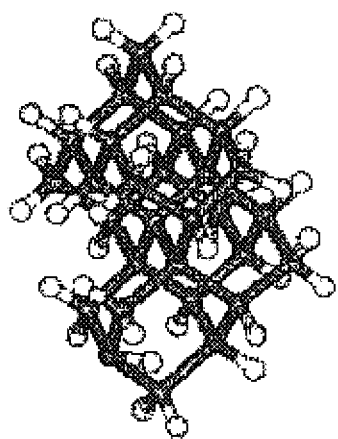
Figure 84:
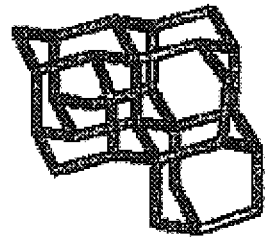
Figure 84:
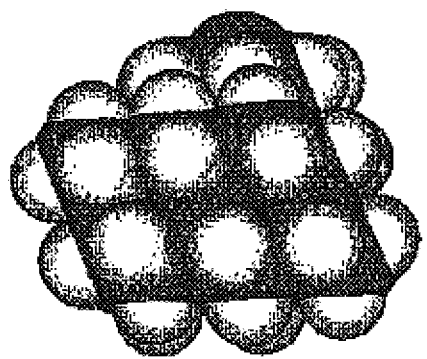
Figure 85:
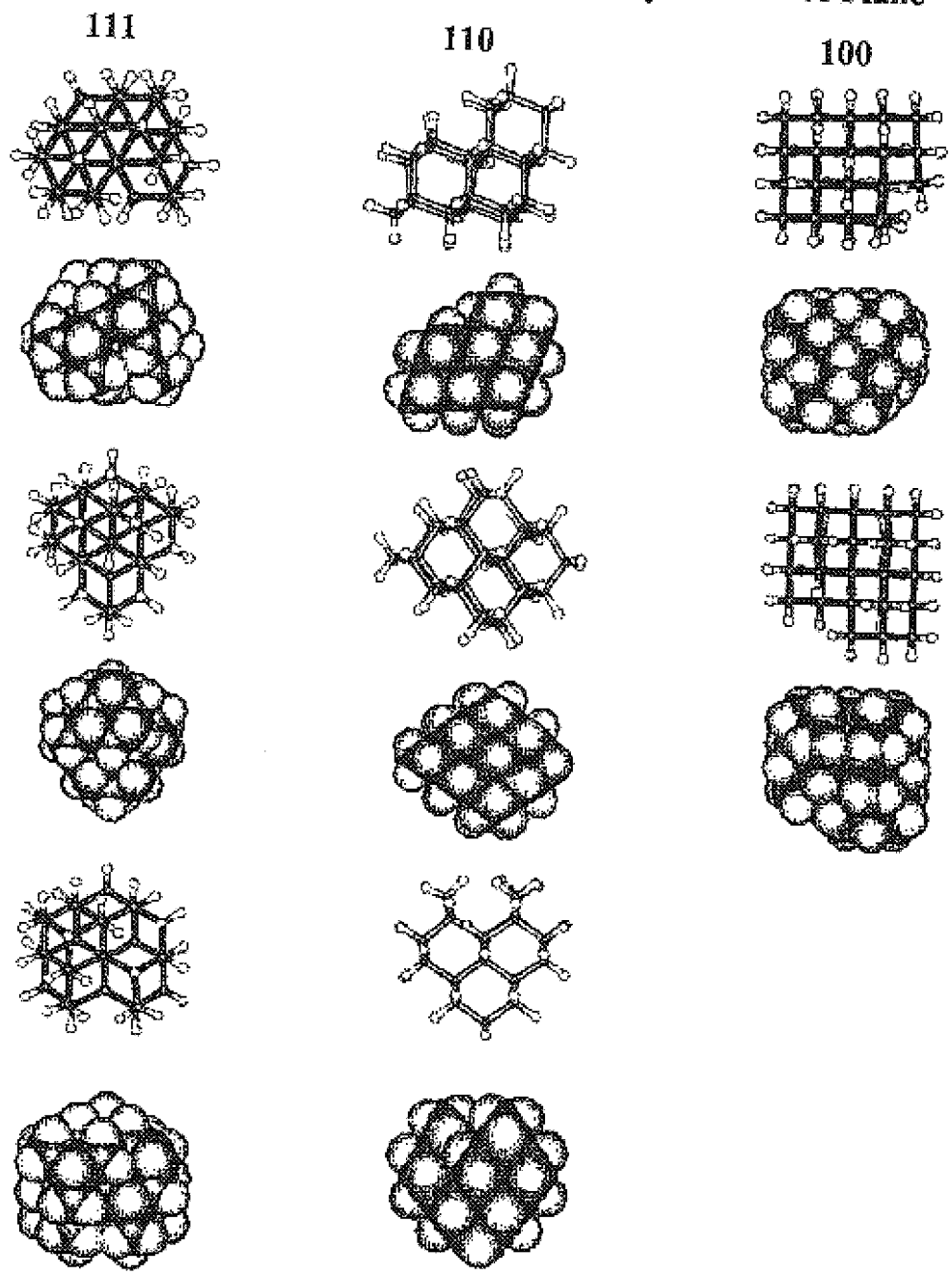
Figure 86:
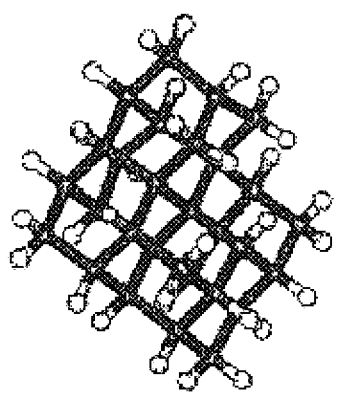
Figure 86:
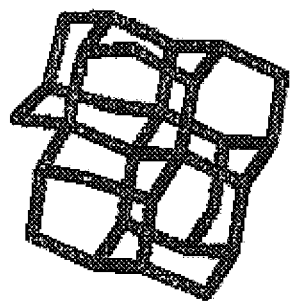
Figure 86:
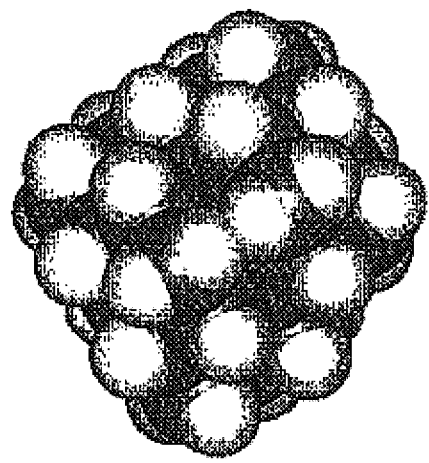
Figure 87:
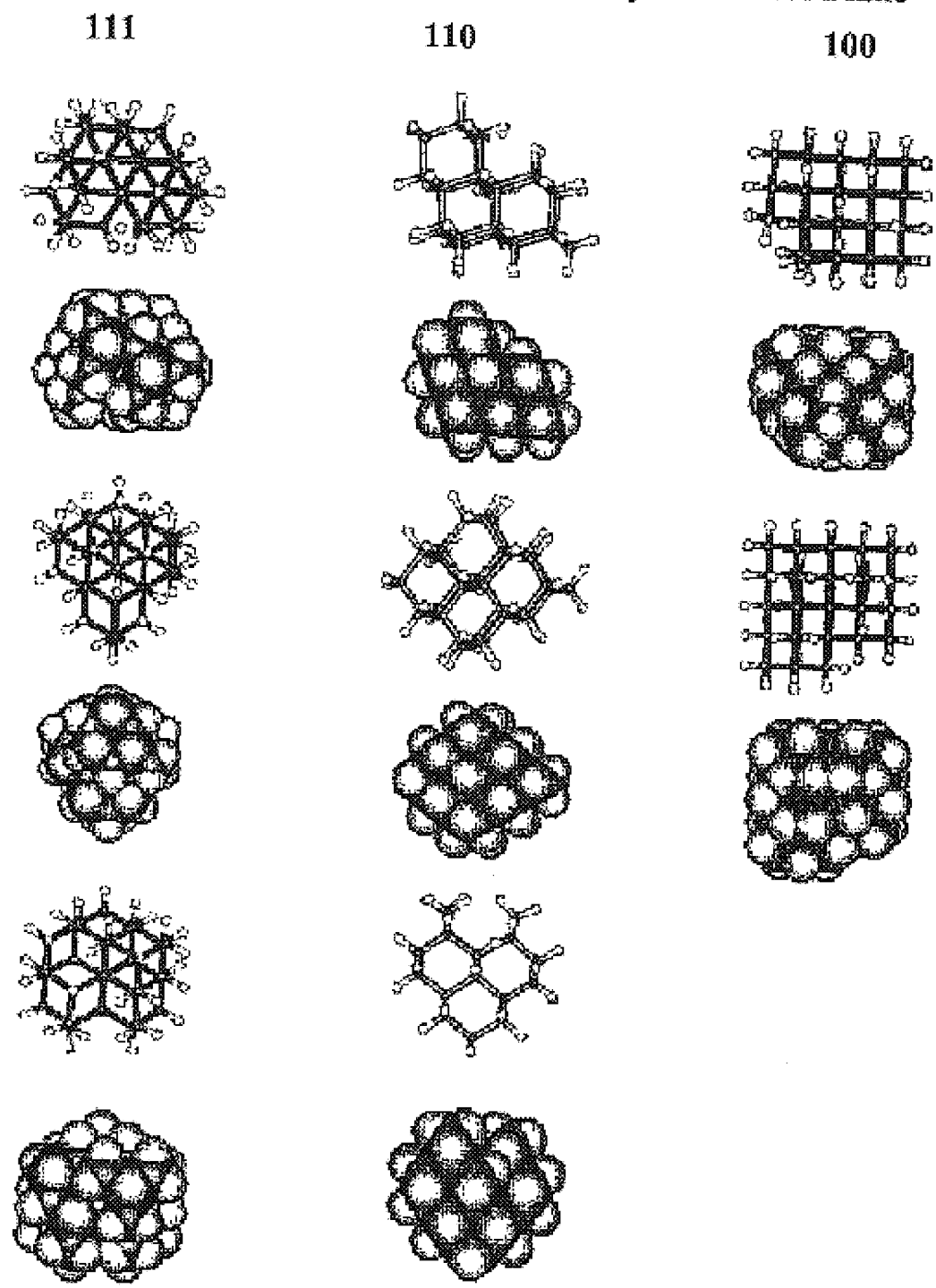
Figure 88:
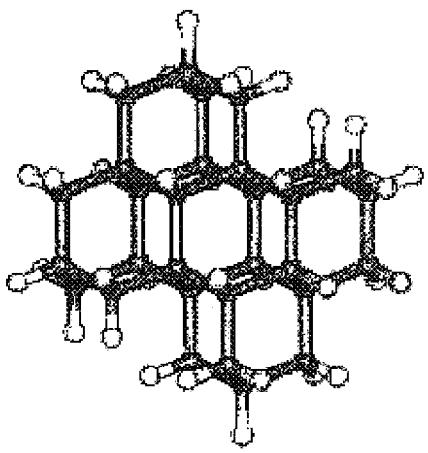
Figure 88:
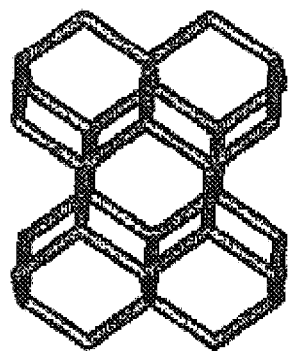
Figure 88:
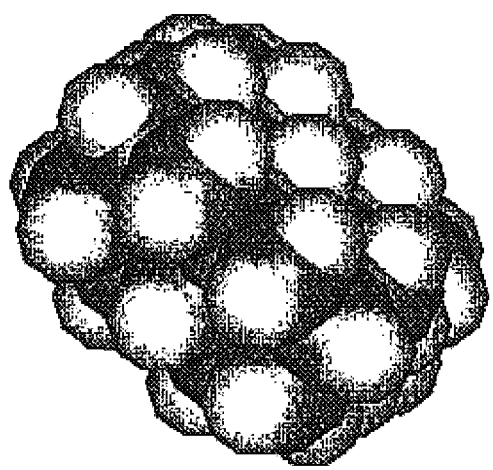
Figure 89:
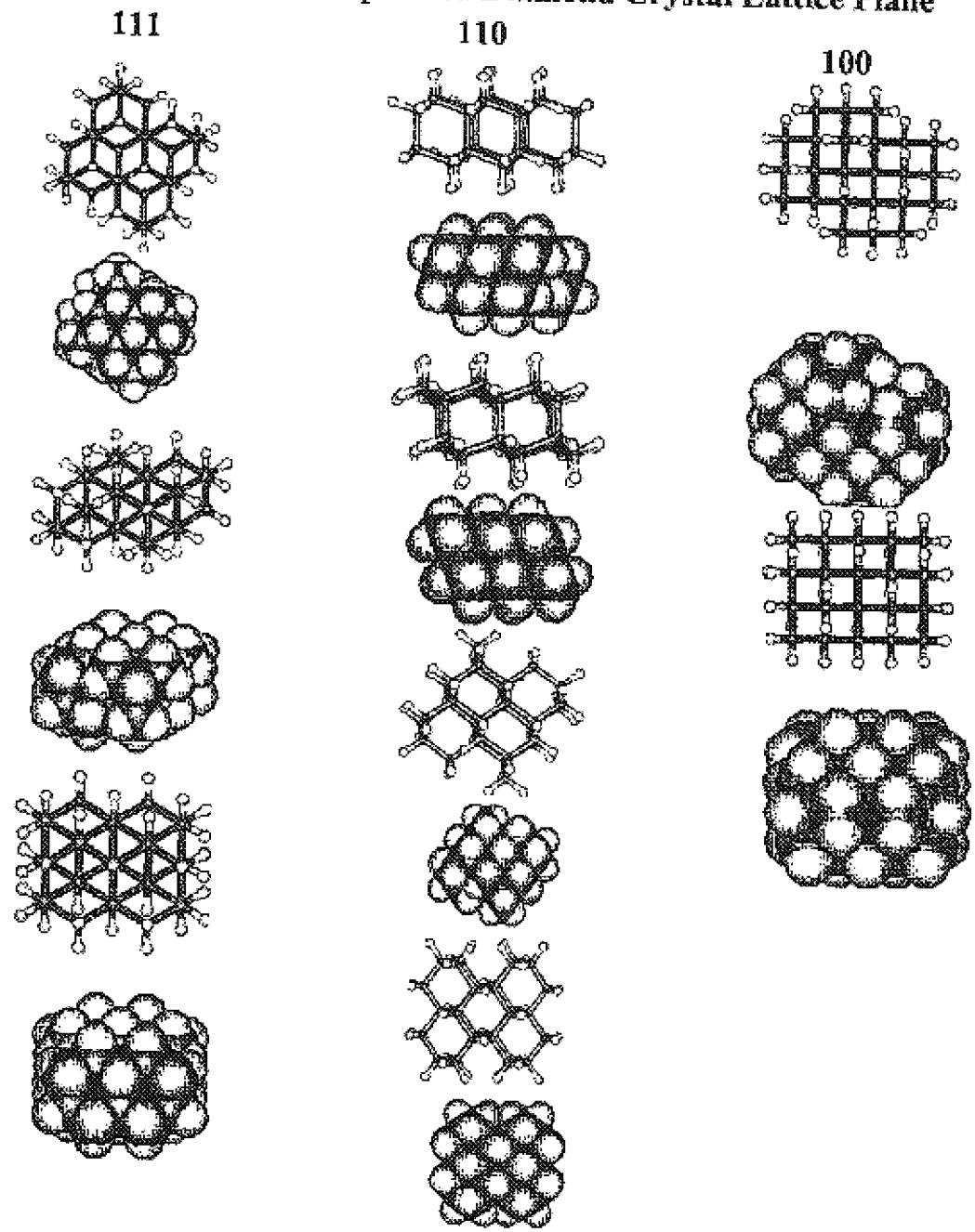
Figure 90:
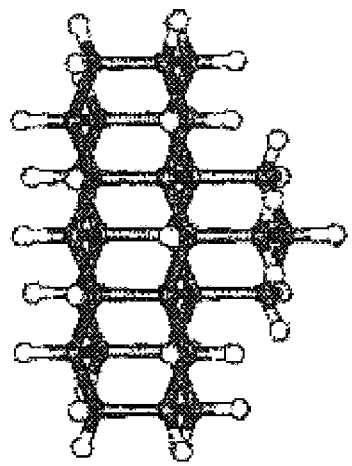
Figure 90:
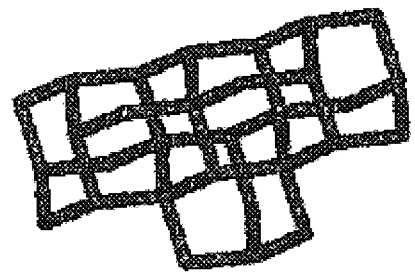
Figure 90:
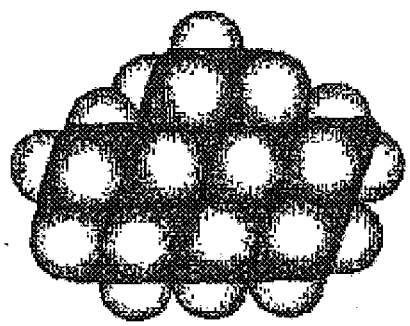
Figure 91:
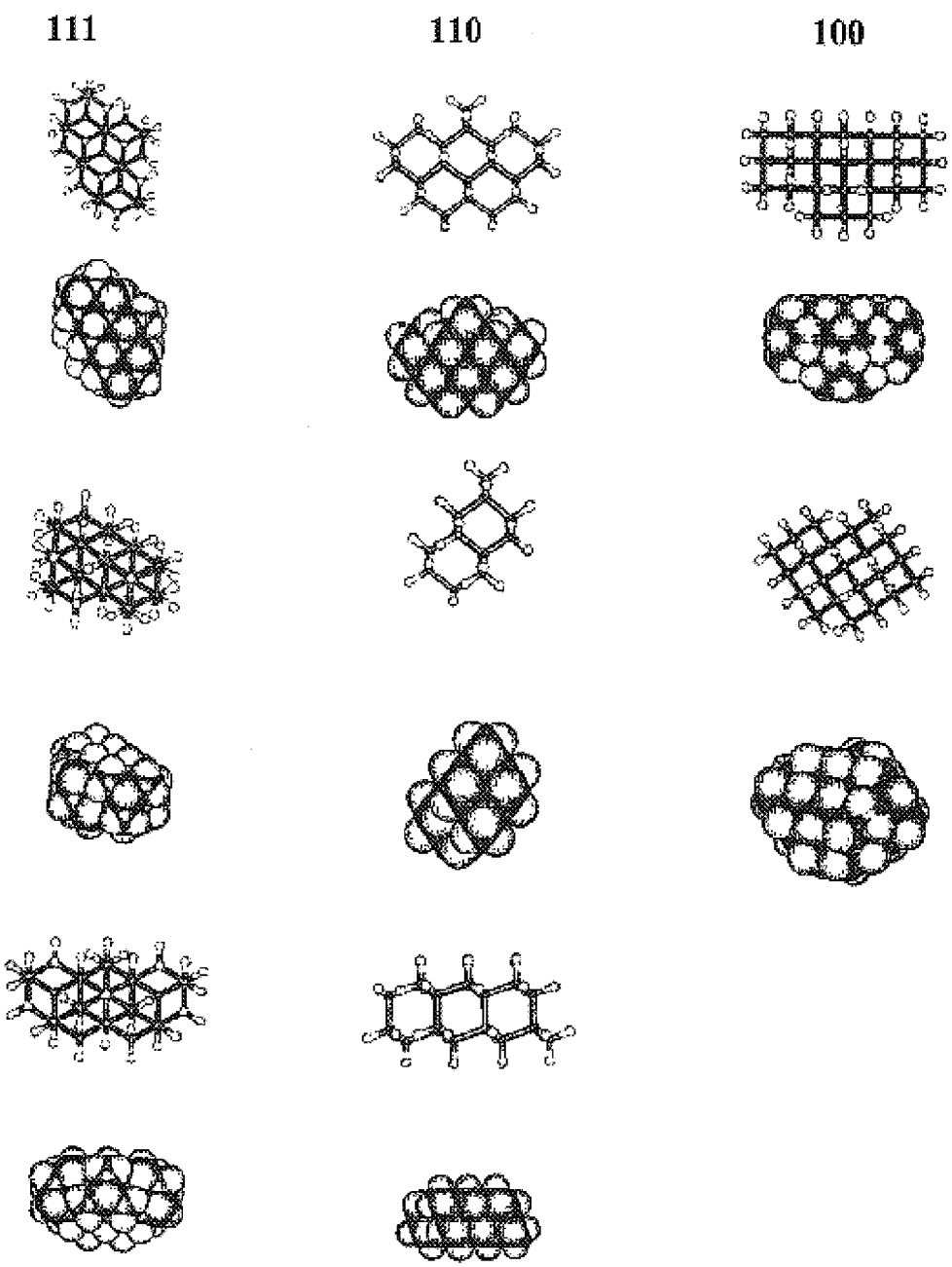
Figure 92:
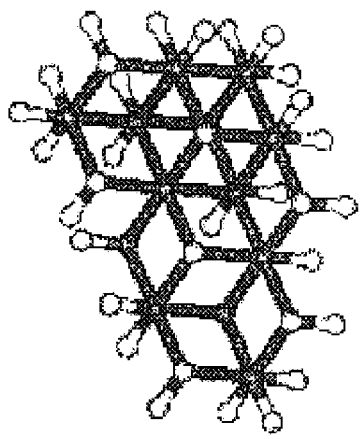
Figure 92:
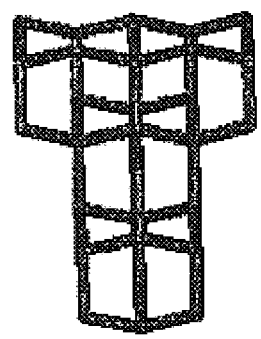
Figure 92:
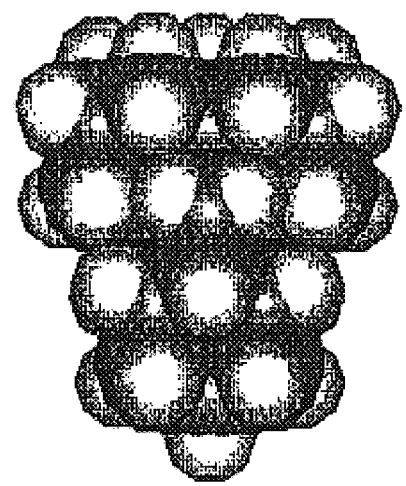
Figure 93:
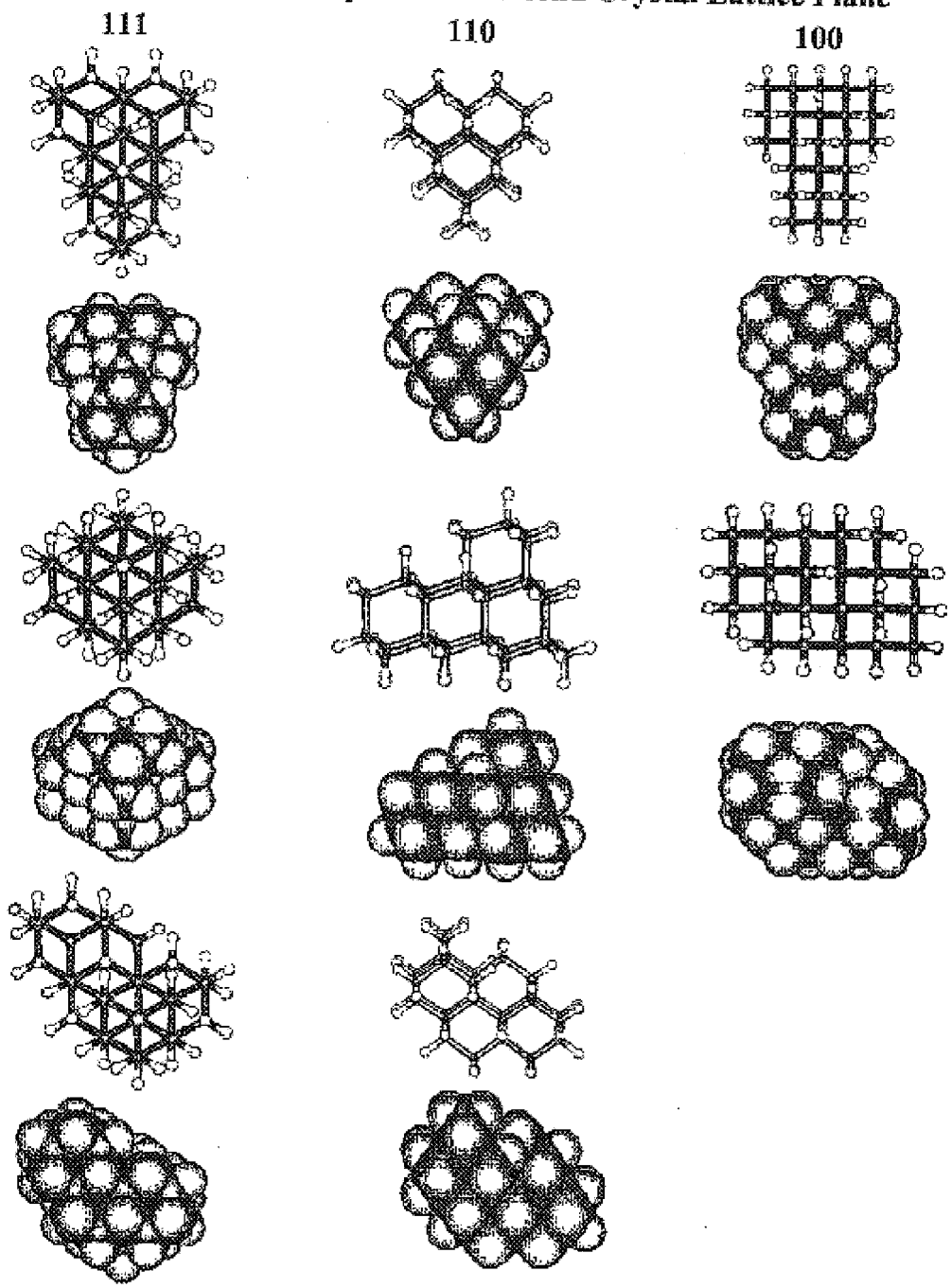
Figure 94:
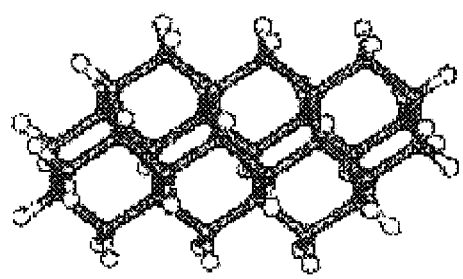
Figure 94:
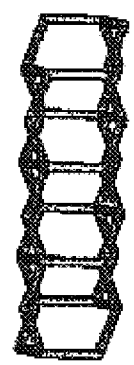
Figure 94:
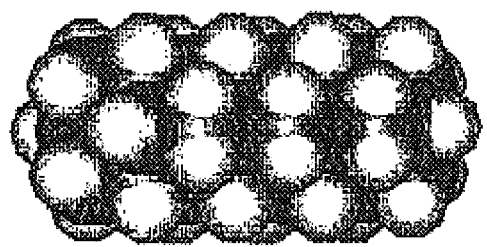
Figure 95:
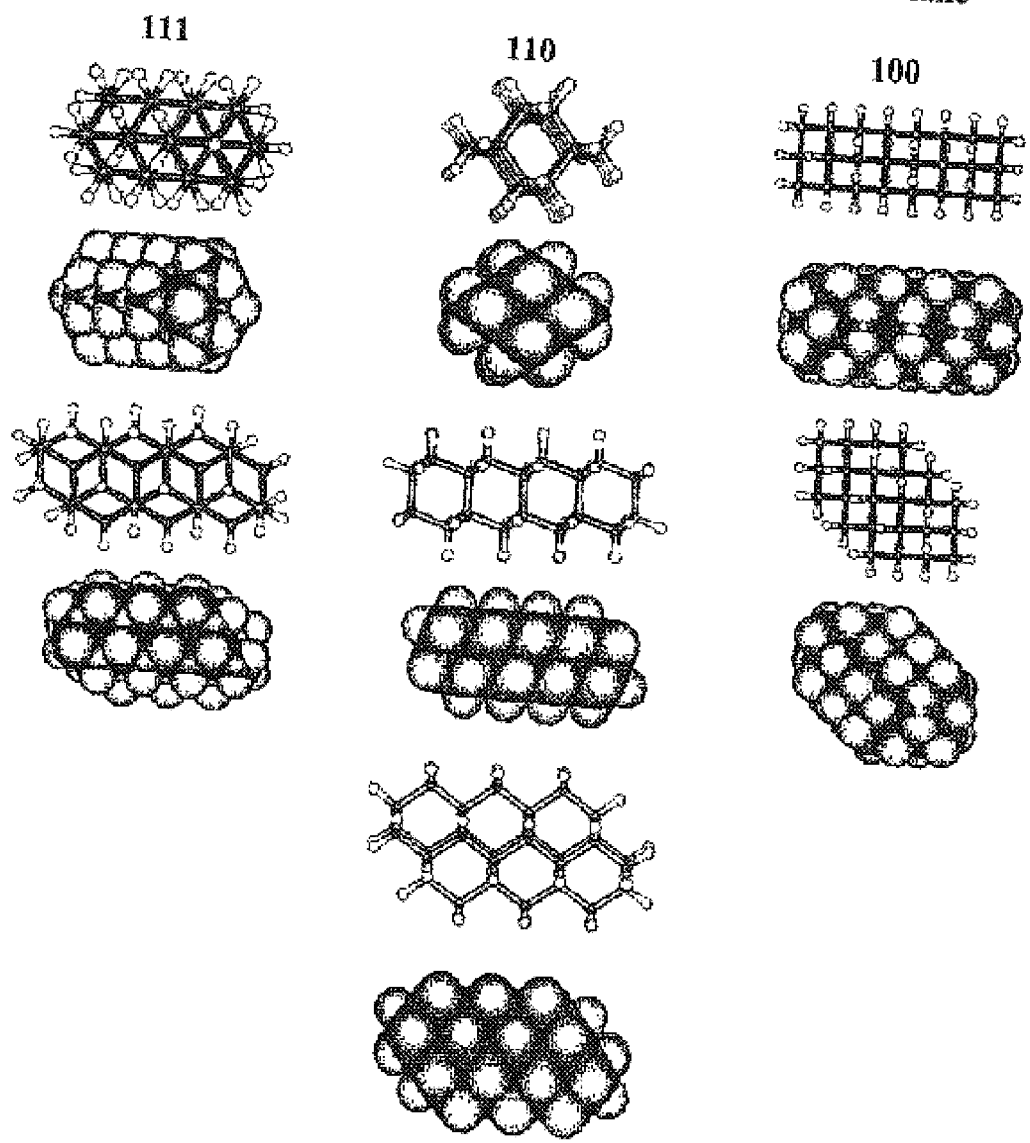
Figure 96:
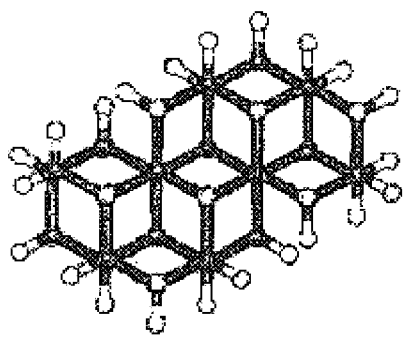
Figure 96:
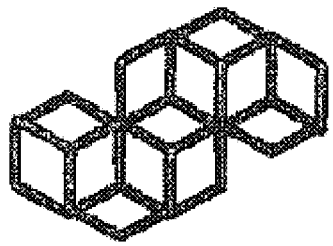
Figure 96:
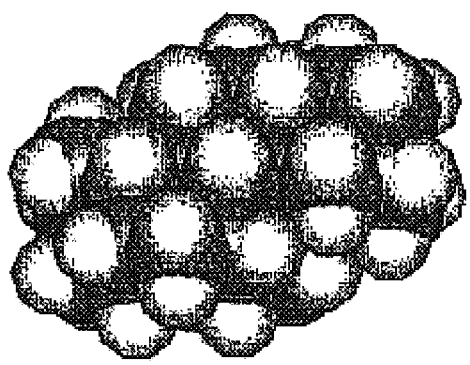
Figure 97:
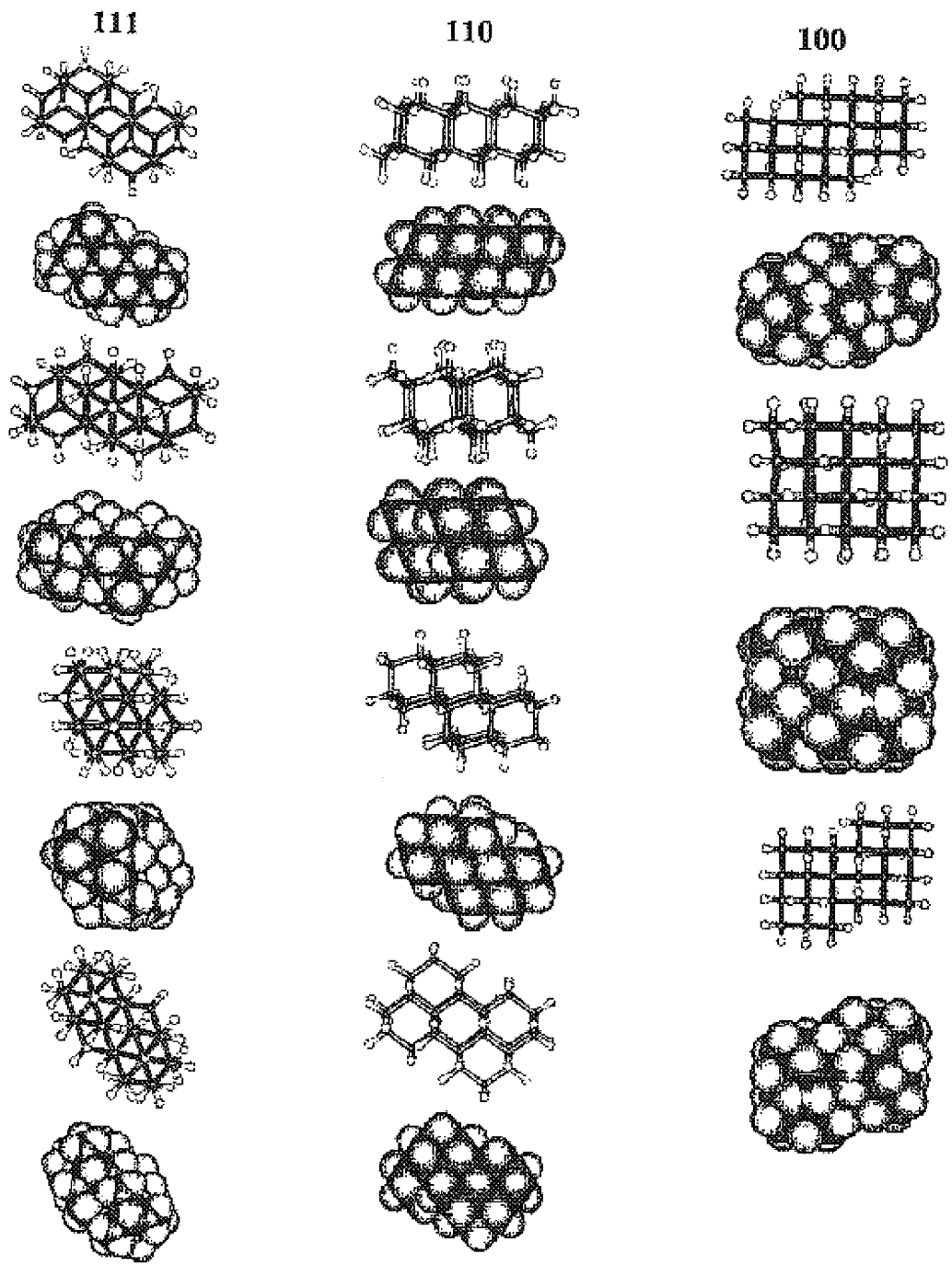
Figure 98:
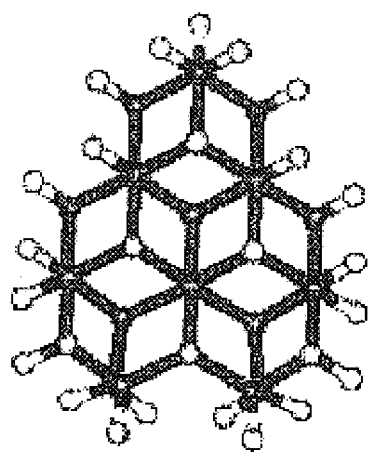
Figure 98:
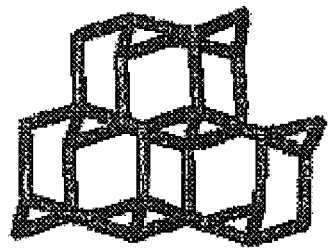
Figure 98:
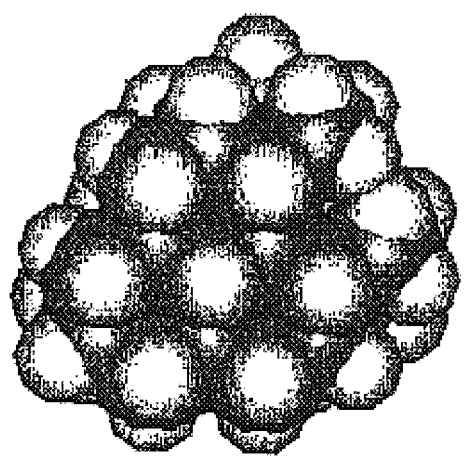
Figure 99:
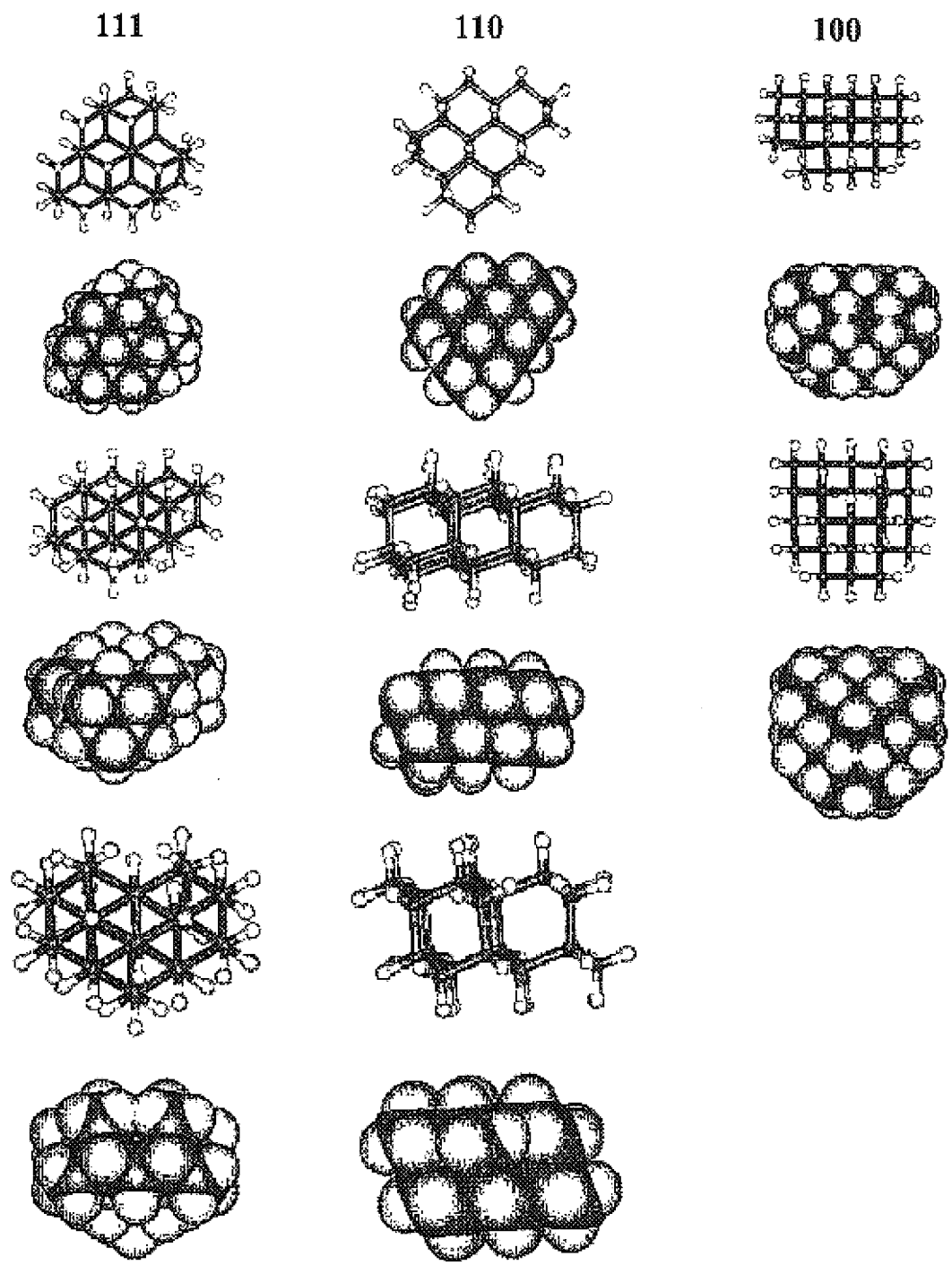
Figure 100:
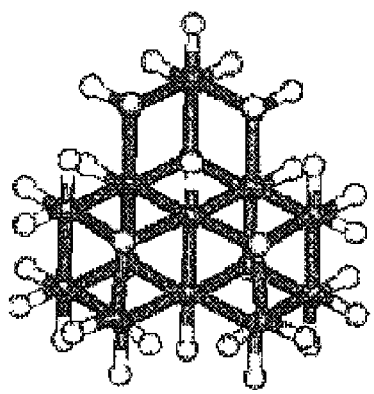
Figure 100:
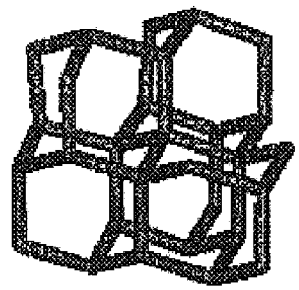
Figure 100:
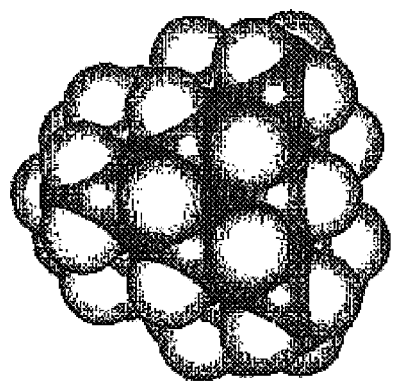
Figure 101:
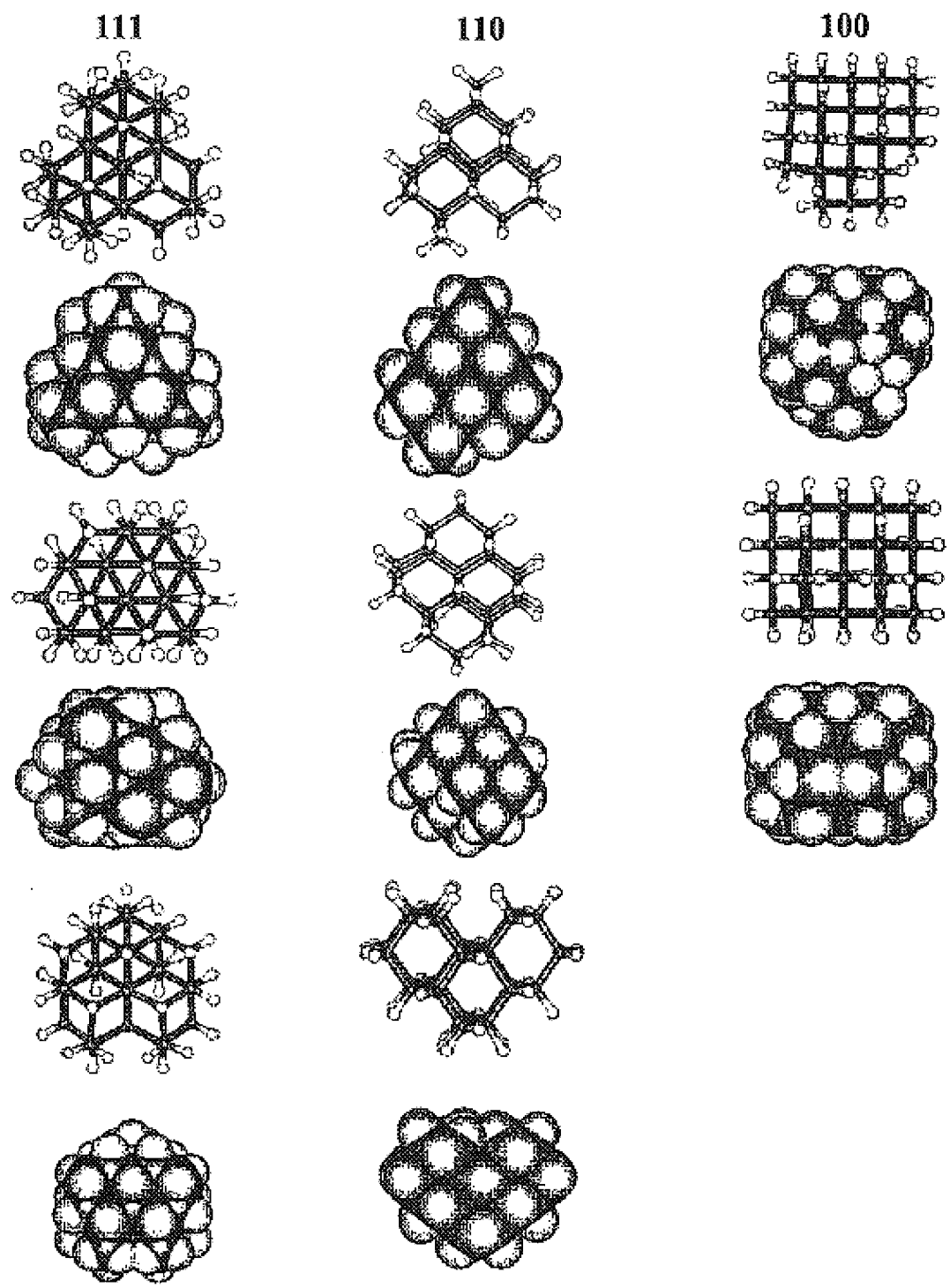
Figure 102:
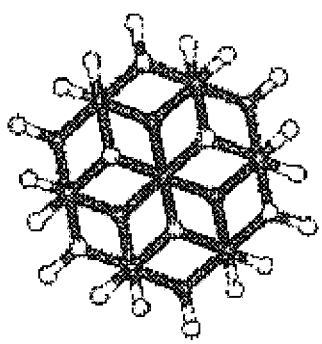
Figure 102:
Figure 102:
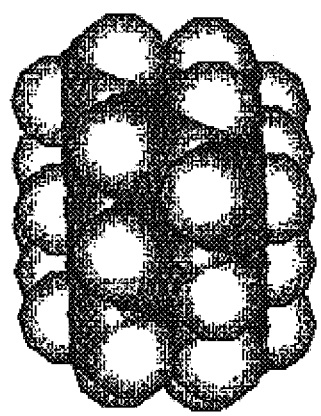
Figure 103:
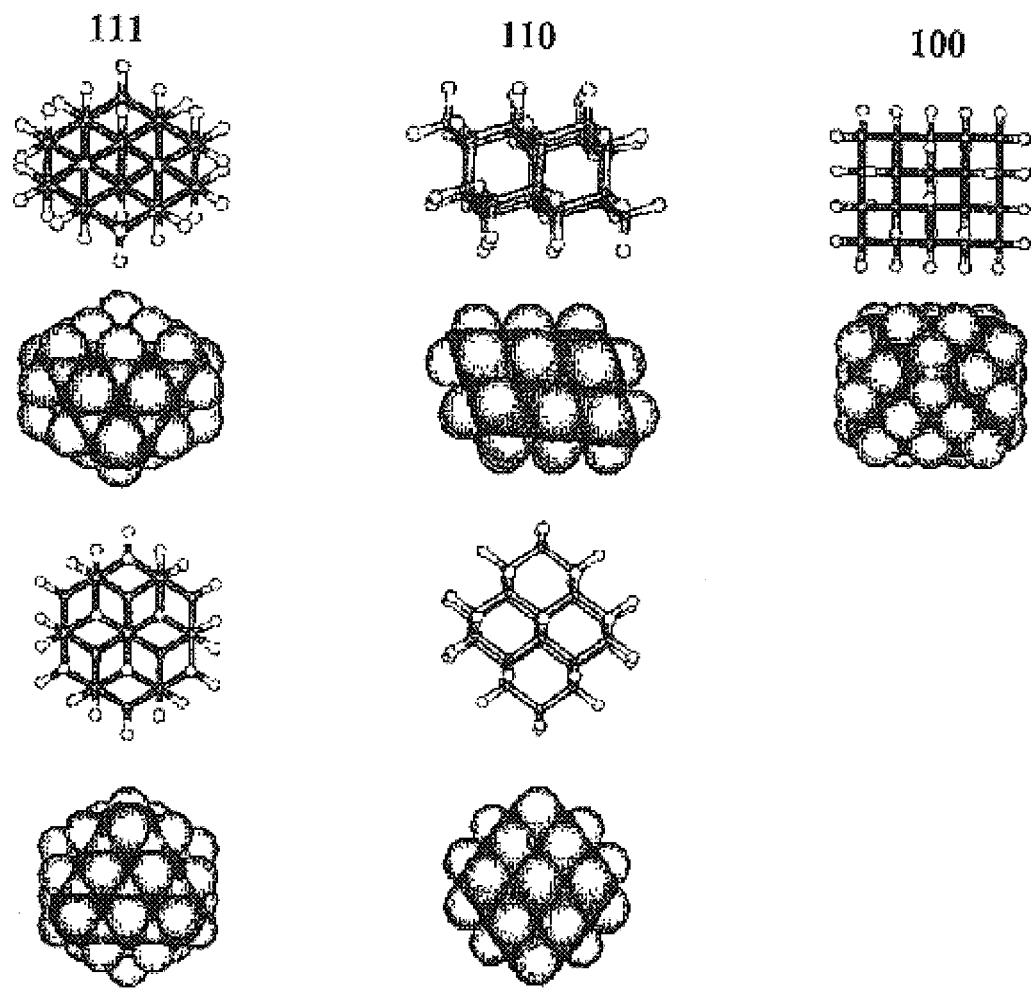
Figure 104:
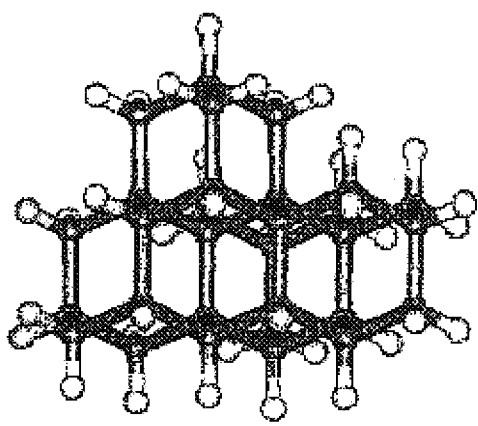
Figure 104:
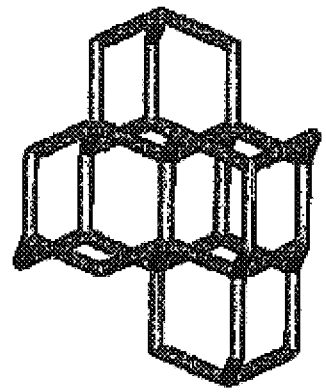
Figure 104:
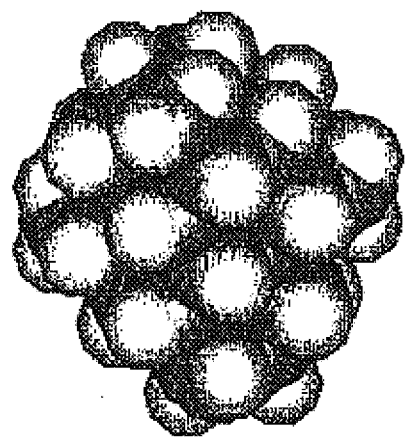
Figure 105:
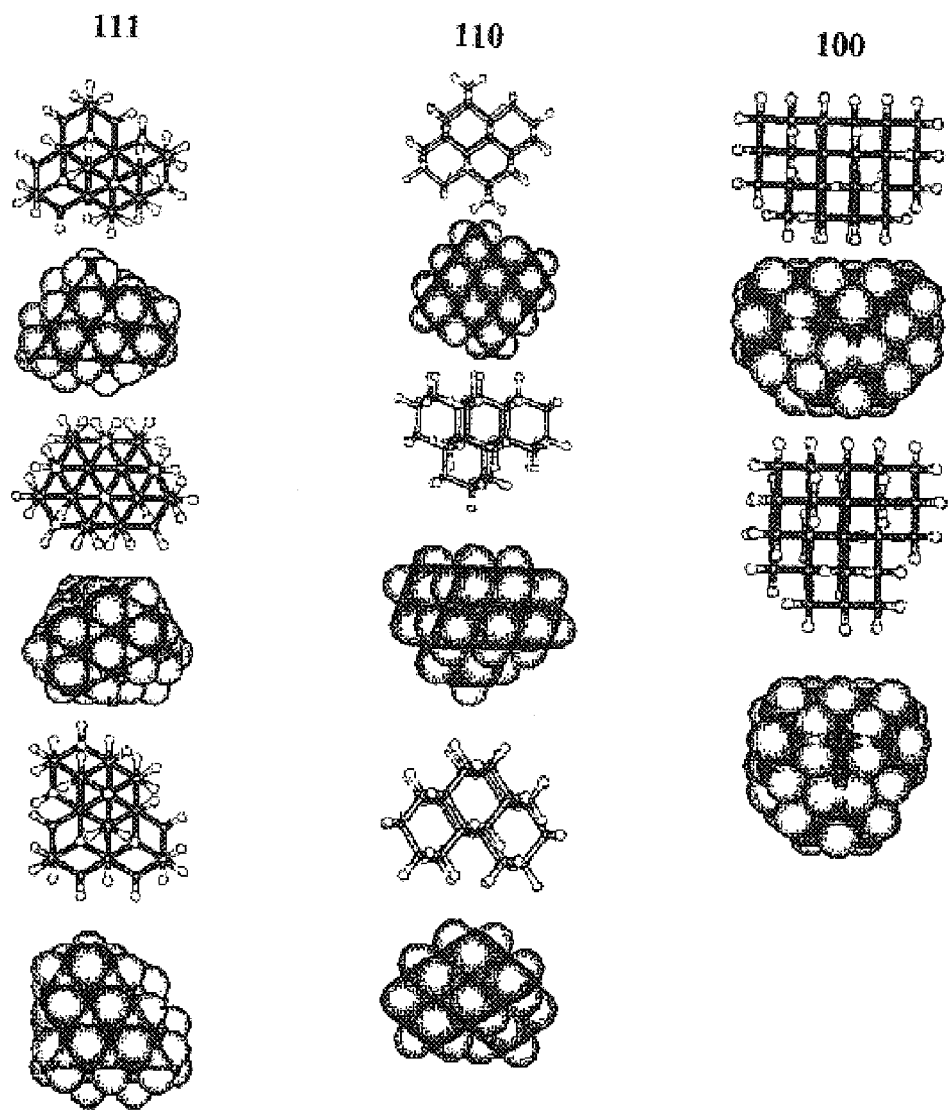
Figure 106:
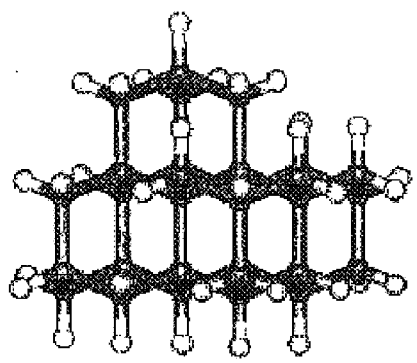
Figure 106:
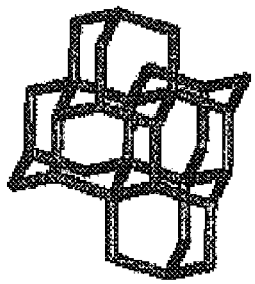
Figure 106:
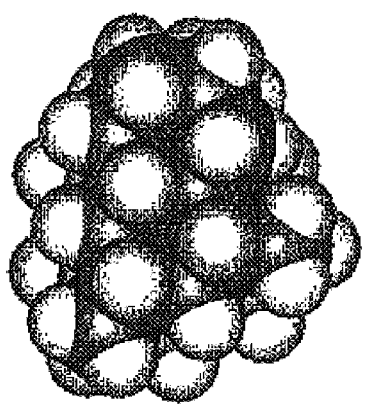
Figure 107:
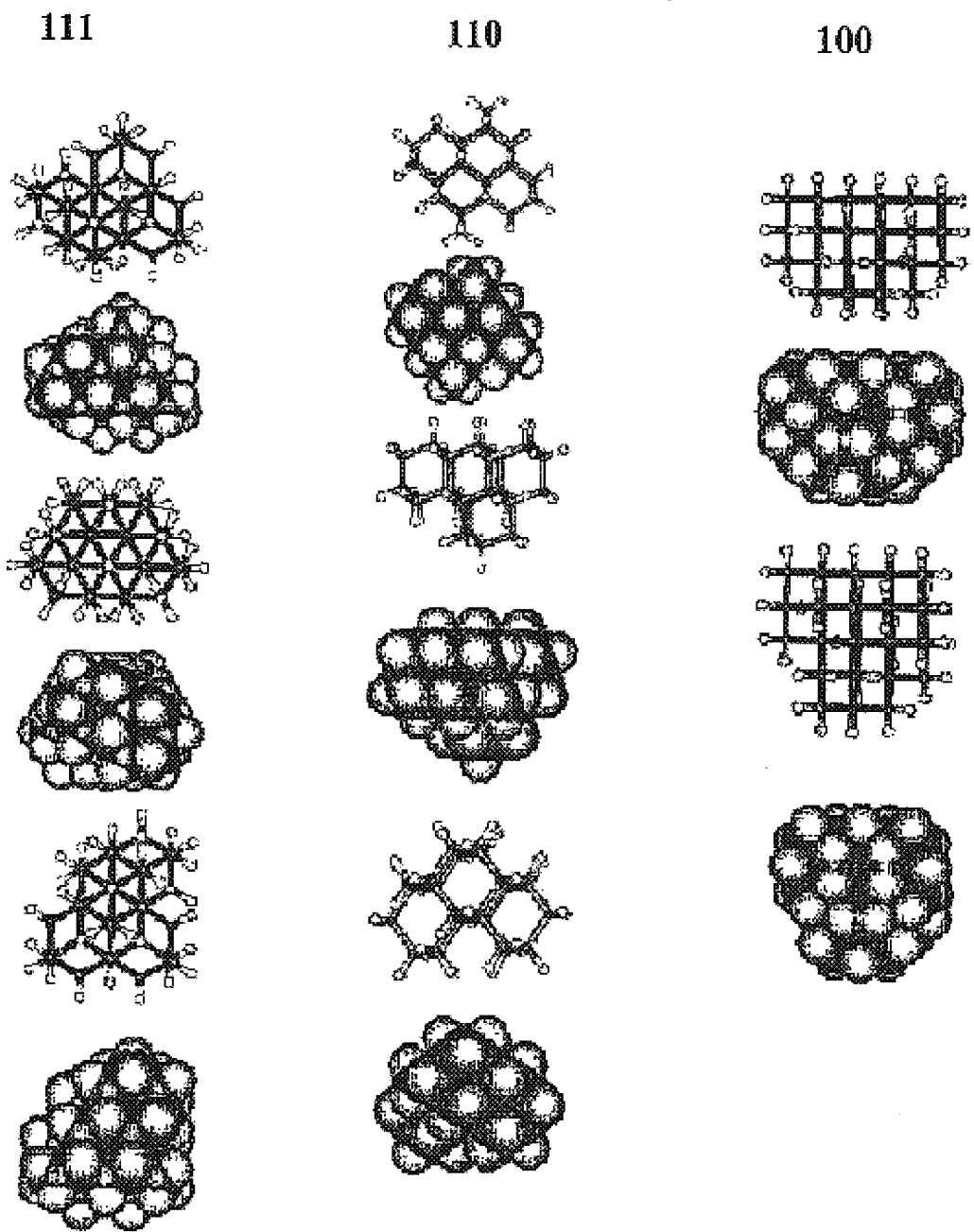

The thirty-nine unsubstituted hexamantanes are individually named and their structures are shown in FIGS. 30-107. Structures are also shown in FIG. 2. The $C_{30}H_{36}$ hexamantanes are preferred hexamantane components and appear in greater concentrations (due to less steric strain). These $C_{30}H_{36}$ materials include:

[1(2)314] enantiomer A hexamantane
[1(2)314] enantiomer B hexamantane
[12(1)32] enantiomer A hexamantane
[12(1)32] enantiomer B hexamantane
[12(1)34] enantiomer A hexamantane
[12(1)34] enantiomer B hexamantane
[12(1,3)4] hexamantane
[12(3)14] enantiomer A hexamantane
[12(3)14] enantiomer B hexamantane
[121(2)3] enantiomer A hexamantane
[121(2)3] enantiomer B hexamantane
[12123] enantiomer A hexamantane
[12123] enantiomer B hexamantane
[12131] enantiomer A hexamantane
[12131] enantiomer B hexamantane
[12134] enantiomer A hexamantane
[12134] enantiomer B hexamantane
[12124] enantiomer A hexamantane
[12124] enantiomer B hexamantane
[12341] enantiomer A hexamantane
[12134] enantiomer B hexamantane
[1(2)3(1)2] hexamantane
[12(3)12] hexamantane
[121(3)4] hexamantane
[12121] hexamantane
[12321] hexamantane
[1(2)3(1)4] enantioner A hexamantane
[1(2)3(1)4] enantiomer B hexamantane This invention is also directed to mixtures of these hexamantane components, as well as substituted hexamantane components alone or together with unsubstituted hexamantane components.

When such compositions are sufficiently enriched in hexamantane components the hexamantane components can form crystal structures. Accordingly, another aspect of this invention is directed to a composition comprising a hexamantane crystal with the proviso that when there is only a single hexamantane component, then it is not the fully condensed unsubstituted hexamantane having the molecular weight of 342 hexamantane components can co-crystallize. Another aspect of this invention is directed to the co-crystals comprising crystals of at least two hexamantane components or co-crystals of hexamantane with other higher diamondoids, such as heptamantane components.

The hexamantanes recovered and isolated in this invention include substituted hexamantane components. These naturally occurring substituted hexamantanes have similar properties to the unsubstituted hexamantane components described herein and are present in the feedstocks. Substituted hexamantanes may act as useful intermediates in various hexamantane applications or can be de-alkylated to yield the corresponding unsubstituted hexamantanes. Substituted hexamantanes contain 1 to 10 alkyl substituents, and more preferably 1 to 4 such substituents.

The most prevalent substituted hexamantanes in the feedstocks used are hexamantanes substituted with lower alkyls. The most prevalent of these are methyl and ethyl-substituted hexamantanes, including methyl, ethyl, dimethyl, and trimethyl hexamantanes.

Utility

These hexamantane containing compositions are useful in micro- and molecular-electronics and nanotechnology applications. In particular, the rigidity, strength, stability, variety of structural forms and multiple attachment sites shown by hexamantanes makes possible accurate construction of robust, durable, precision devices with nanometer dimensions. These special structural characteristics set these compounds apart from acyclic molecules, from condensed ring systems and even from bridged ring counterparts. The great stability, nanometer size, variable yet rigid three-dimensional geometries, well defined distances for places of attachment and nonplanar bridgeheads lead to their unique features. Such features make these hexamantane compounds and compositions useful in nanotechnogy applications. In recent years there has been a rapidly rising interest in synthesizing large assemblies of organic molecules that might be able to serve as scaffolding structures in efforts to construct molecular objects of nanometer sized dimensions. Due to rigidity and special geometries of the hexamantane components it is expected that molecular aggregates and molecular building blocks comprising them will enable the construction and synthesis of an unprecedented array of desirable materials and may find applications in molecular electronic and computing devices, reduced size of machines such as molecular robotics and self replicated manufacturing systems or simply as novel materials with special chemical, optical, electrical properties and thermal conductivity properties for coatings, film layering, and other applications taking advantage of the diamond-like properties, etc.

In addition, hexamantane containing compositions can also be used in a high quality lubricant which exhibits a high Viscosity Index and a very low pour point.[4] When so employed, these lubricants comprise from about 0.1 to 10 weight percent hexamantanes.

[4] Wu, et al., High Viscosity Index Lubricant Fluid, U.S. Pat. No. 5,306,851, issued Apr. 26, 1994.

Still further, these hexamantane containing compositions can be used as high density fuels in the manner described by Chung, et al.[5], incorporated herein by reference.

[5] Chung et al., *Recent Development in High-Energy Density Liquid Fuels*, Energy and Fuels, 13, 641–649 (1999).

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | |
|---|---|
| API = | American Petroleum Institute |
| ATM EQV = | atmospheric equivalent |
| EOR Traps = | end of run traps |
| FID = | flame ionization detector |
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

EXAMPLES 1
Isolation of Hexamantane Components

The purpose of this example is to demonstrate procedures which can be used for the enrichment and isolation of the thirty-nine hexamantane components. These procedures employed Feedstock B and a pyrolysis step, however this procedure could be facilitated using other feedstocks and without the pyrolysis step. After removal of lower boiling point nonhexamantane components (including some lower diamondoid and tetramantanes and some heptamantanes) from the feedstock by distillation, the hexamantane components in this example were recovered by chromatography and crystallization. The distillation preferably can be operated to provide specific cuts, thus removing both lower and higher boiling point components, leaving only components within a desired boiling point range. Such fractionation can provide an increased concentration for a desired product within the temperature range.

Step 1

Figure 3:
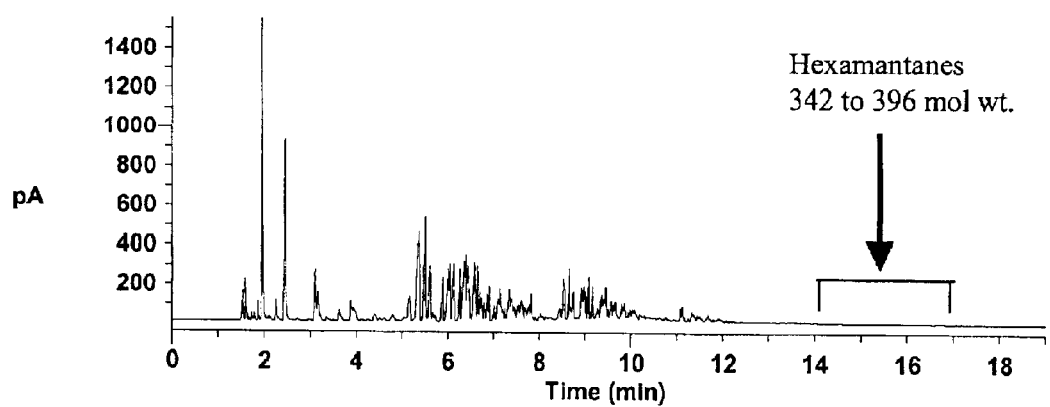
FIG. 3 illustrates the gas chromatogram of a gas condensate feedstock; one of the original feedstocks used in the Examples (Feedstock A). Hexamantanes are present at low concentrations, not detectable, but are shown in vacuum distillation fractions (FIG. 6).
Figure 4:
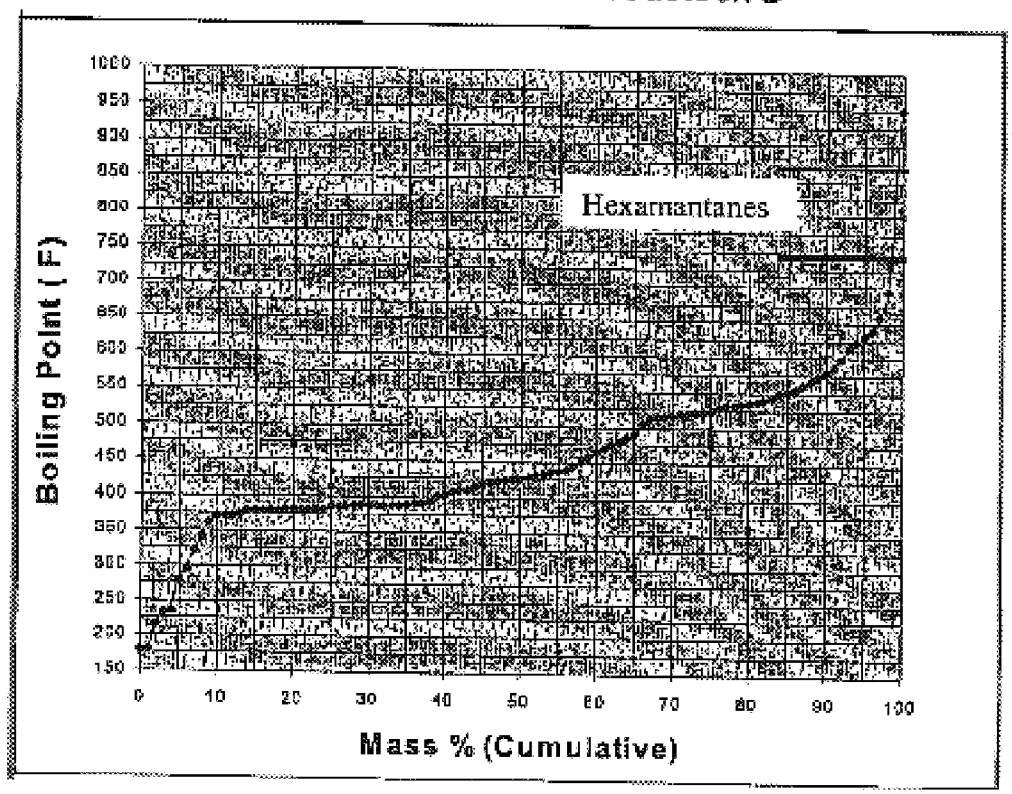
FIG. 4 illustrates a simulated distillation profile of a gas condensate feedstock containing petroleum byproducts used in the Examples (Feedstock B). Boiling points depicted are atmospheric equivalents. Hexamantanes were found in the atmospheric residue (650° F.+) of Feedstock B.

Suitable starting materials were obtained. These materials included a gas condensate oil, Feedstock A (a gas chromatogram of this material is depicted in FIG. 3), and a gas condensate oil containing petroleum byproducts Feedstock B (a high temperature simulated distillation profile of this type of material is depicted in FIG. 4). Although other condensates, petroleums, or refinery cuts and products could have been used, these two materials were chosen due to their high concentration of higher diamondoids, (0.3 weight percent), as determined by GC and GC/MS. Both feedstocks were light colored and had API gravities between 19 and 20° API.

Step 2

Samples from Feedstocks A and B were distilled into a number of fractions based on boiling points to separate the lower boiling point components (non-diamondoids and lower diamondoids) and to further concentrate and enrich hexamantanes in various fractions. The yields of atmospheric distillate fractions of two separate samples of Feedstock B are shown in Table 1, below, and are contrasted to the simulated distillation yields calculated for that feedstock. As seen from Table 1, the simulation data is in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 5:
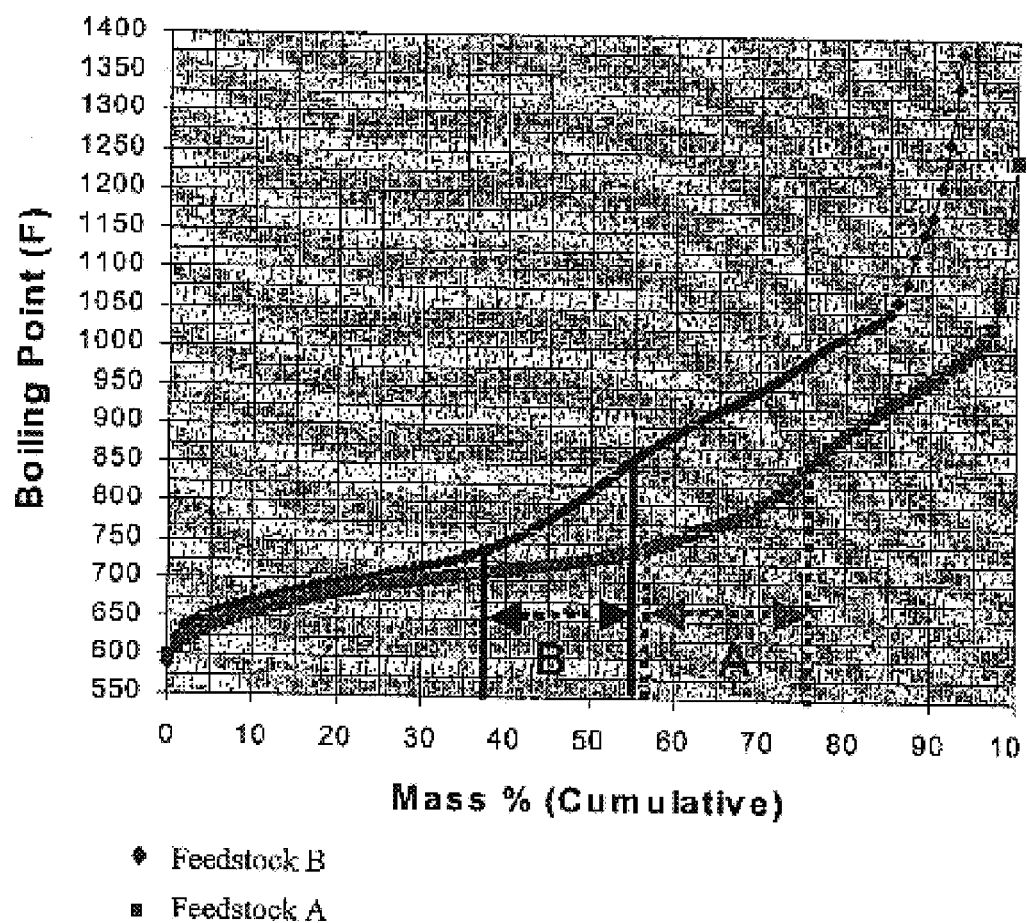
FIG. 5 illustrates a high temperature simulated distillation profile of atmospheric residue of diamondoid rich gas condensates; Feedstock A and Feedstock B. Labels A and B show the portions of each feedstock which contain the hexamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the hexamantane containing fractions. In terms of atmospheric equivalent boiling points the hexamantanes were anticipated to be predominately within the range of 330° F. to about 550° F. with a large portion within the range of 740° F. to about 470° F. The lower mass percent shown for the hexamantane-containing fractions of Feedstock B as compared to Feedstock A was due to nondiamondoid materials in Feedstock B, The nondiamondoid material can be removed by subsequent processes such as pyrolysis.

A sample of gas condensate, Feedstock A was distilled into 38 fractions to remove lower diamondoids and concentrate higher diamondoids of interest as verified by GC (see FIG. 6) wherein residue left after the distillation of 38 fractions was recovered, predominately boiling in the range of from 750+° F. The temperature range for these fractions are atmospheric equivalent temperatures, wherein the actual distillation can occur under various conditions including reduced pressure.

Figure 6:
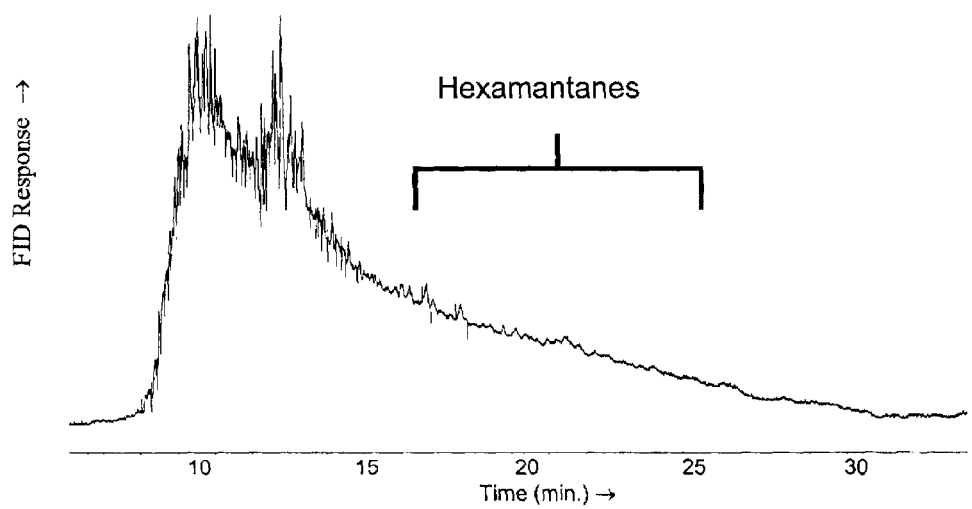
FIG. 6 illustrates gas chromatographic profiles of vacuum distillate residue containing hexamantanes and higher diamondoids from a gas condensate, Feedstock A. The GC range of uncondensed hexamantanes is indicated.
Figure 12:
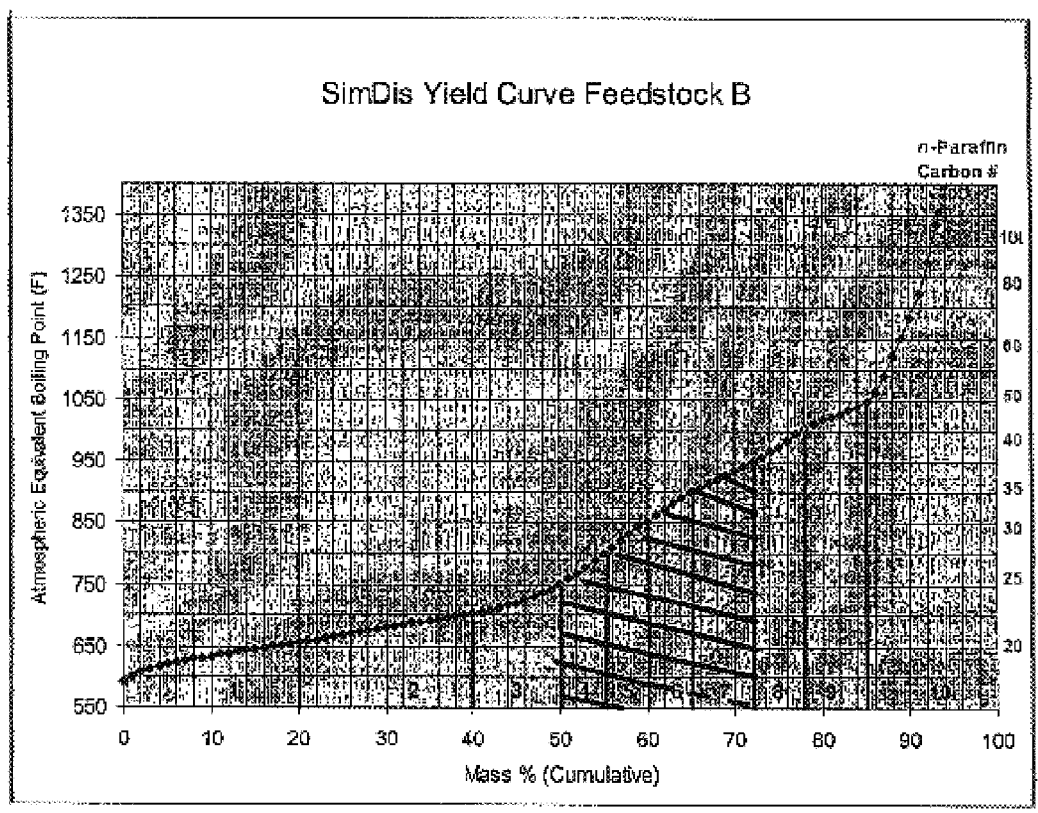
FIG. 12 illustrates a high temperature simulated distillation profile of Feedstock B using the atmospheric distillation 650° F.+bottoms as feedstock. This FIG. also illustrates the targeted cut points (1–10) for higher diamondoid isolations. Hexamantanes are contained primarily in distillate fractions 4 through 7.
Figure 13:
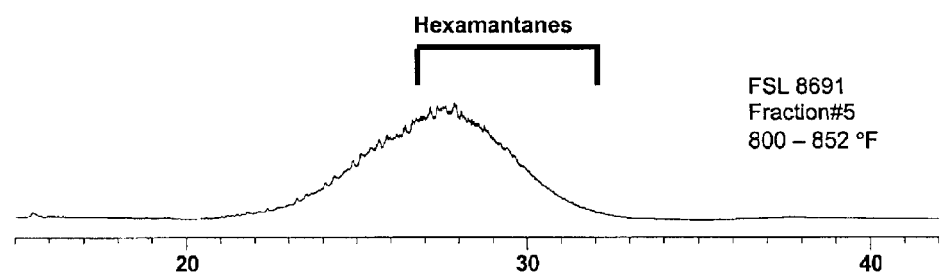
FIGS. 13(A, B, C) illustrates the gas chromatograms of vacuum distillate Fractions #5, #6, and #7 of Feedstock B atmospheric distillation 650° F.+bottoms illustrated in FIG. 12 and exemplified in Example 1. Fraction #4 also contains condensed hexamantanes but is not shown here.
Figure 13:
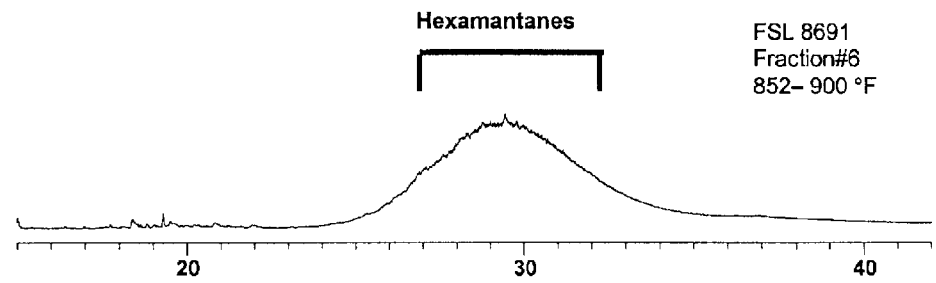
Figure 13:
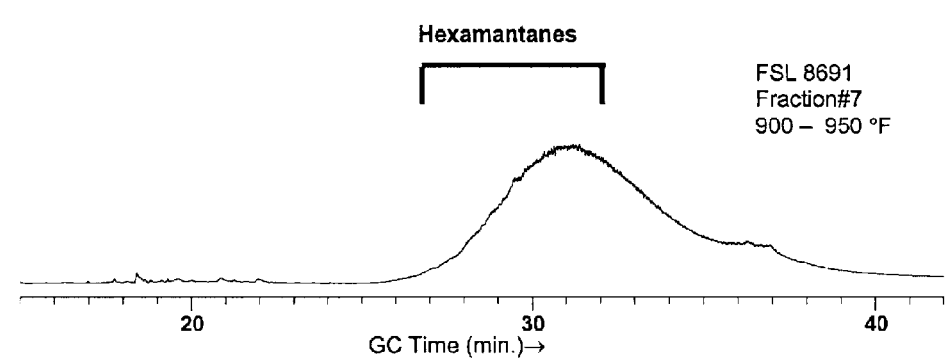

Additionally, Feedstock B was distilled into fractions containing higher diamondoids guided by high temperature simulated distillation curve (FIG. 12). Comparison of FIGS. 6 and 13 shows that Feedstock B contains impurities not present in Feedstock A. The feed to the high temperature distillation process was the atmospheric 650° F.+bottoms. Whole Feedstock B distillation reports are given in Tables 2A&B. Tables 3A&B, illustrate the distillation reports for Feedstock B 643° F.+distillation bottoms.

TABLE 2A

Distillation Report for Feedstock B
(FSL # 8471)
Feedstock B
Column Used: Clean 9" x 1.4" Protruded Packed

| | VAPOR TEMP ST–END | | | DISTILLATION RECORD | | | | NORMALIZED | | ACTUAL | |
|---|---|---|---|---|---|---|---|---|---|---|---|
| CUT | | | | WEIGHT G | VOLUME ml @ 60° F. | API 60/60 | DENSITY @ 60° F. | WT PCT | VOL PCT | WT PCT | VOL PCT |
| 1 | 226 | – | 349 | 67.0 | 80 | 38.0 | 0.8348 | 7.61 | 8.54 | 7.39 | 8.26 |
| 2 | 349 | – | 491 | 507.7 | 554 | 22.8 | 0.9170 | 57.65 | 59.12 | 55.98 | 57.23 |
| 3 | 491 | – | 643 | 269.6 | 268 | 9.1 | 1.0064 | 30.62 | 28.60 | 29.73 | 27.69 |
| COL HOLDUP | | | | 0.2 | 0 | 6.6 | 1.0246 | 0.02 | 0.00 | 0.02 | 0.00 |
| BTMS | 643 | + | | 36.1 | 35 | 6.6 | 1.0246 | 4.09 | 3.74 | 3.98 | 3.62 |
| EOR TRAPS | | | | 0.0 | 0 | | | 0.00 | 0.00 | | 0.00 |
| TOTALS | | | | 880.6 | 937 | | | 100.00 | 100.00 | 97.09 | 96.80 |
| LOSS | | | | 26.4 | 31 | | | | | 2.91 | 3.20 |
| FEED | | | | 907.0 | 968 | 19.5 | 0.9371 | | | 100.00 | 100.00 |
| BACK CALCULATED API AND DENSITY | | | | | | 19.1 | 0.9396 | | | | |

TABLE 2B

Distillation Report for Feedstock B
(FSL # 8471)
Feedstock B
Column Used: Clean 9" x 1.4" Protruded Packed

| TEMPERATURE DEGREES F. | | | | | | | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | | START OVERHEAD | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| Cut 2 looks Milky, White crystals form in Run Down Line. Heat Lamp applied to drip tube. Cool to transfer btms to smaller flask. | | | | | | | | | | |
| 208 | 437.7 | 323 | 10.000 | 3:1 | | | START OVERHEAD | | | |
| 378 | 643.3 | 550 | 10.000 | 3:1 | 3 | 268 | 269.6 | 9.9 | 75.0 | 9.1 |
| Shutdown due to dry pot | | | | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B
(FSL # 8691)
Feedstock B - Atmospheric distillation resid 650° F. + bottoms
Column Used: Sarnia Hi Vac

| TEMPERATURE DEGREES F. | | | | | | | API GRAVITIES | | |
|---|---|---|---|---|---|---|---|---|---|
| VAPOR | | | | | VOL | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |

| VLT | ATM EQV. | POT | PRESSURE TORR | REFLUX RATIO | CUT NO | ml 60° F. | WEIGHT G | HYD RDG | TEMP ° F. | 60° F. |
|---|---|---|---|---|---|---|---|---|---|---|
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | MID AND | END OF RUN TRAPS | | | | 20 | 17.8 | (mathematically combined) | | |
| | | VOLUME DISTILLED | | | | 2701 | | | | |
| | | COLUMN HOLDUP | | | | 4 | 4.0 | 0.0 | 0.0 | 3.4 |
| | | BOTTOMS | | | | 593 | 621.8 | 11.0 | 214.0 | 3.4 |
| | | RECOVERED | | | | 3298 | 3311.7 | | | |
| | | FEED CHARGED | | | | 3298 | 3326.3 | 18.0 | 234.0 | 8.6 |
| | | LOSS | | | | −5 | 14.6 | | | |

TABLE 3B

Distillation Report for Feedstock B-btms
(FSL # 8691)
Feedstock B - Atmospheric distillation resid 650° F. + bottoms
Column Used: Sarnia HiVac

| CUT | VAPOR TEMP ST–END | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|
| 1 | 601 | − 656 | 666.4 | 639 | 4.1 | 1.0435 | 20.12 | 19.38 | 20.03 | 19.40 |
| 2 | 656 | − 702 | 666.9 | 646 | 5.6 | 1.0321 | 20.14 | 19.59 | 20.05 | 19.62 |
| 3 | 702 | − 752 | 334.3 | 330 | 8.3 | 1.0122 | 10.09 | 10.01 | 10.05 | 10.02 |
| 4 | 752 | − 800 | 167.7 | 173 | 14.5 | 0.9692 | 5.06 | 5.25 | 5.04 | 5.25 |
| 5 | 800 | − 852 | 167.3 | 181 | 21.7 | 0.9236 | 5.05 | 5.49 | 5.03 | 5.50 |
| 6 | 852 | − 900 | 167.1 | 181 | 21.9 | 0.9224 | 5.05 | 5.49 | 5.02 | 5.50 |
| 7 | 900 | − 950 | 238.4 | 257 | 21.2 | 0.9267 | 7.25 | 7.79 | 7.17 | 7.80 |
| 8 | 950 | − 976 | 85.4 | 91 | 18.9 | 0.9408 | 2.58 | 2.76 | 2.57 | 2.76 |
| 9 | 976 | − 1000 | 80.8 | 85 | 18.2 | 0.9452 | 2.44 | 2.58 | 2.43 | 2.58 |
| 10 | 1000 | − 1026 | 93.8 | 98 | 16.9 | 0.9535 | 2.83 | 2.97 | 2.82 | 2.98 |
| COL HOLDUP | | | 4.0 | 4 | 3.4 | 1.0489 | 0.12 | 0.12 | 0.12 | 0.12 |
| BTMS | 1026 | + | 621.8 | 593 | 3.4 | 1.0489 | 18.78 | 17.98 | 18.69 | 18.01 |
| EOR TRAPS | | | 17.8 | 20 | | | 0.54 | 0.61 | 0.54 | 0.61 |
| TOTALS | | | 3311.7 | 3298 | | | 100.00 | 100.00 | 99.56 | 100.15 |
| LOSS | | | 14.6 | −5 | | | | | 0.44 | −0.15 |
| FEED | | | 3326.3 | 3293 | 8.6 | 1.0100 | | | 100.00 | 100.00 |
| BACK CALCULATED API & DENSITY | | | | | 9.4 | 1.0039 | | | | |

TABLE 4

Elemental Composition of Feedstock B
Analyses on Feedstock B Atmospheric Distillation 650 + F Resid

| Measured | Value |
| --- | --- |
| Nitrogen | 0.991 wt % |
| Sulfur | 0.863 wt % |
| Nickel | 8.61 ppm |
| Vanadium | <0.2 ppm |

Table 4 illustrates the elemental composition of Feedstock B atmospheric distillation (650+F) residue including some of the identified impurities. Table 4 displays the weight percent nitrogen, sulfur, nickel and vanadium present within this feedstock. These materials are removed in subsequent steps.

Step 3

The higher diamondoids enriched by the separations of Step 2 were further treated to isolate a hexamantane fraction. In one case the distillation fraction 38 of Feedstock A was passed through a silica-gel gravity liquid chromatographic column (using cyclohexane elution solvent) to remove polar compounds and asphaltenes and concentrate higher diamondoids. The use of silver nitrate impregnated silica gel (10% by weight $AgNO_3$) provides cleaner diamondoid-containing fractions by removing the free aromatic and polar components. Higher diamondoids elute in the first eluting cyclohexane fraction off the column (before aromatic hydrocarbons appeared in the column eluent column. While it is not necessary to use this chromatographic separation method, it facilitates subsequent steps.

Alternatively, pyrolysis products (as disclosed in Example 2) prepared using distillate fractions of Feedstock B could be passed through a silica-gel or $AgNO_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Step 4

The eluent from the column chromatography was analyzed by GC/MS to determine the GC retention times of hexamantanes. Individual hexamantane components with molecular weight 396 were assigned a number according to their elution order on this GC/MS assay. These hexamantanes were the most abundant and selected for convenience. Similar assays could be prepared for the other molecular weights, see Example 5. This assigned number was used to identify individual hexamantanes in subsequent steps. Note that enantiomeric pairs are not resolved in this analysis and so these enantiomeric pairs (racemic mixtures) were assigned as single number. Hexamantane elution times ran between 17.88 min. (hexamantane #1) and 19.51 min. (hexamantane #7) in a typical GC/MS assay used in Examples 3 and 4. Retention times vary with changing GC columns and conditions requiring remeasurement of retention times.

Step 5

Figure 7:
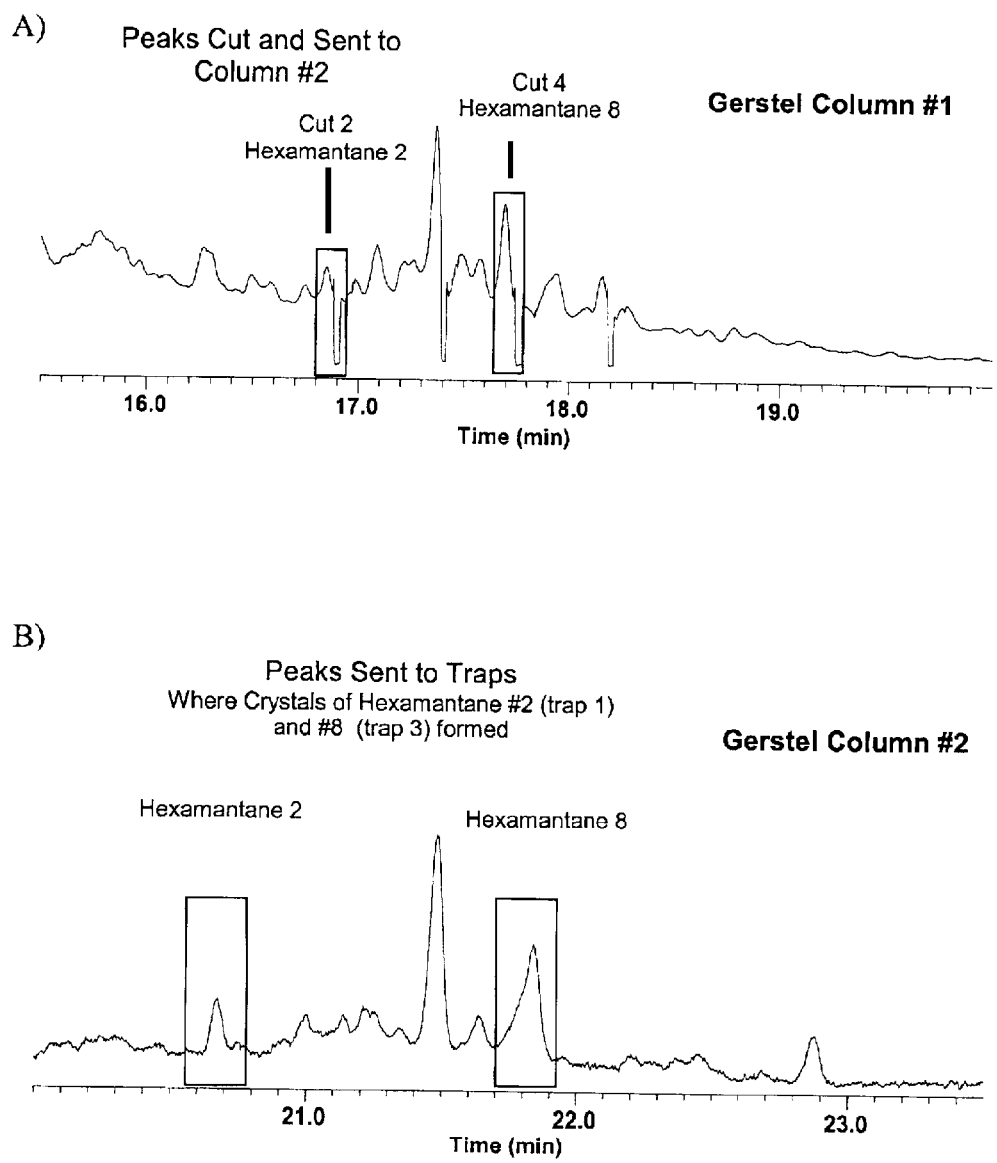
FIGS. 7(A, B) illustrates the preparative capillary gas chromatographic data for hexamantane isolations.

A two-column preparative capillary gas chromatograph was then used to isolate hexamantanes from the distillate fractions cleaned-up by column chromatography. The cut times for the hexamantanes were set for the first preparative capillary GC column, methyl silicone DB-1 equivalent, using the retention times and patterns from GC/MS assay (from step 4 above). The results are shown in the top of FIG. 7A, identified as "peak cut and sent to column 2" which contains two of the hexamantane fractions from Feedstock B. The preparative capillary gas chromatograph used was manufactured by Gerstel, Inc., Baltimore, Md., USA. However, other gas chromatographs could be used.

Figure 8:
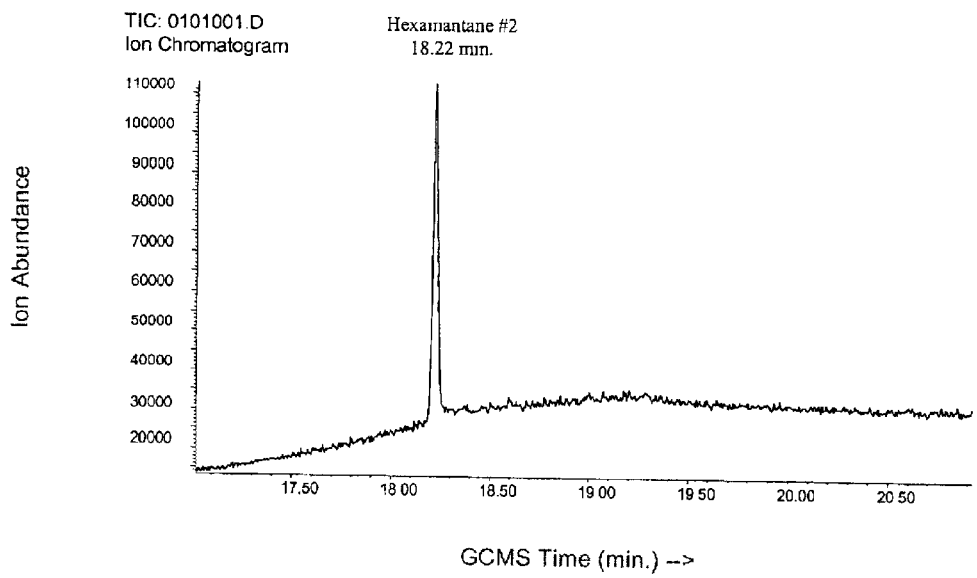
FIGS. 8(A, B) illustrates the GC/MS total ion chromatogram and mass spectrum of a hexamantane #2 isolated by preparative capillary gas chromatography.
Figure 8:
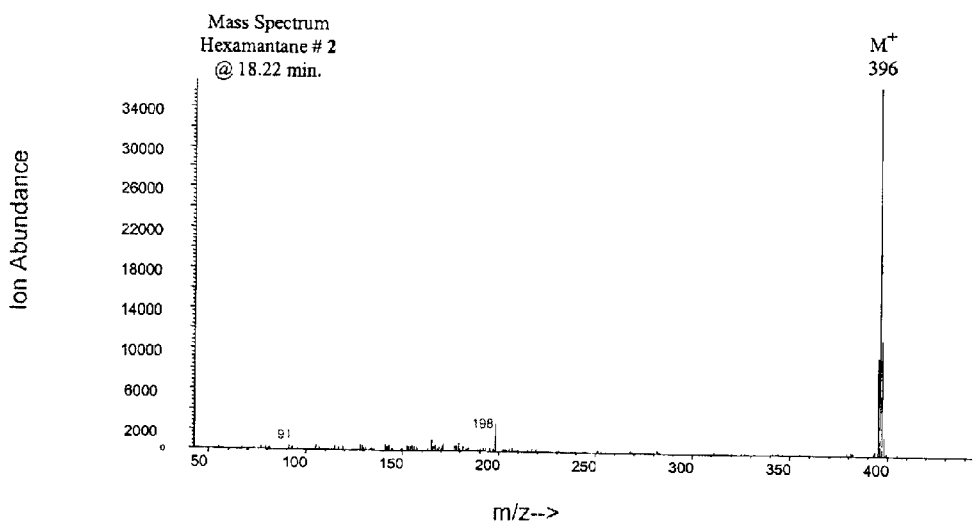
Figure 9:
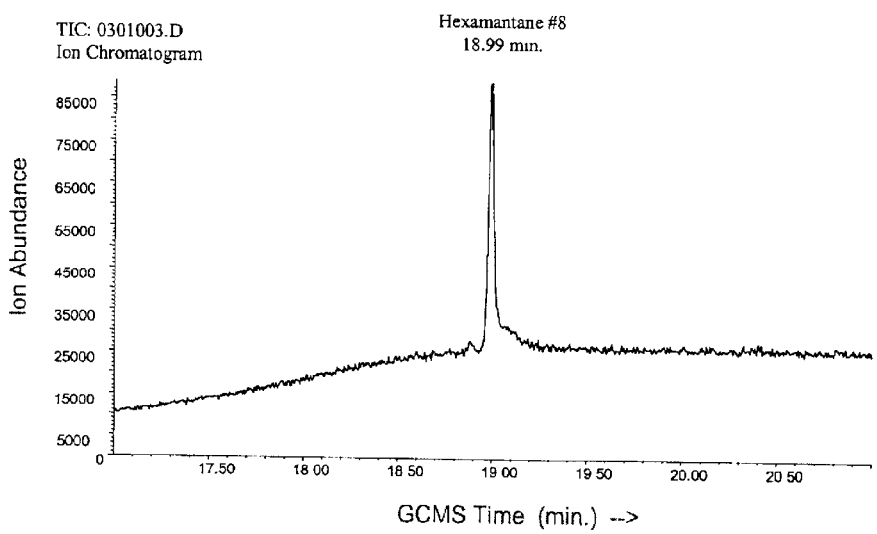
FIGS. 9(A, B) illustrates the GC/MS total ion chromatogram and mass spectrum of a hexamantane #8 highly concentrated by preparative capillary gas chromatography.
Figure 9:
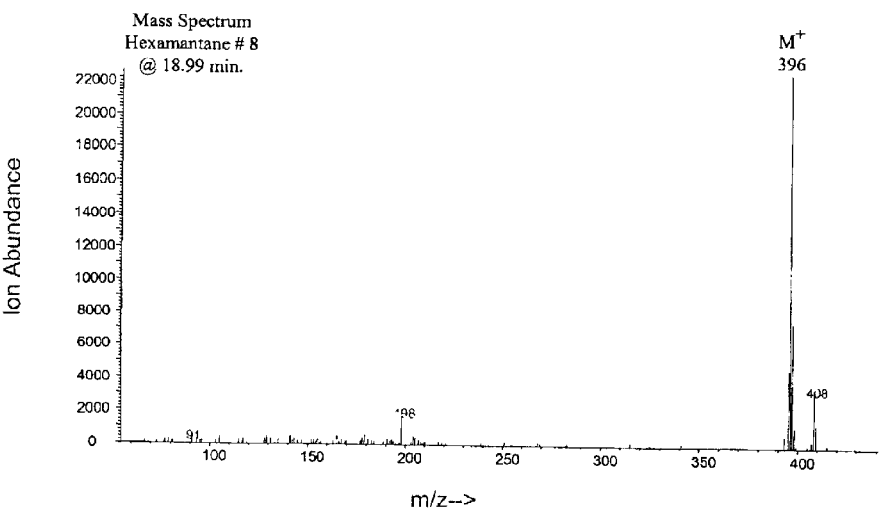

The first column was used to concentrate the hexamantanes by taking cuts that were then sent to the second column (see FIG. 7B illustrated for hexamantane #2 and #8). The second column, phenyl-methyl silicone a DB-17 equivalent, further separated and purified the hexamantanes and then was used to isolate peaks of interest and retain them into individual vials (traps 1–6). GC trap fraction 1 was collected and further processed for the separation of hexamantane #2. GC trap fraction 3 was collected and further processed for the separation of hexamantane #8. Subsequent GC/MS analysis of trap #1 material (FIG. 8) showed it to be hexamantane #2 based upon the earlier run GC/MS assay of step 4. Similarly, the GC analysis of trap #3 material (FIG. 9) showed it to be hexamantane #8. This procedure could be repeated to isolate the other hexamantanes.

Step 6

Figure 10:
FIG. 10 illustrates a photomicrograph of hexamantane #2 crystals isolated from Feedstock B by preparative gas chromatography (FIGS. 7 and 8).
Figure 11:
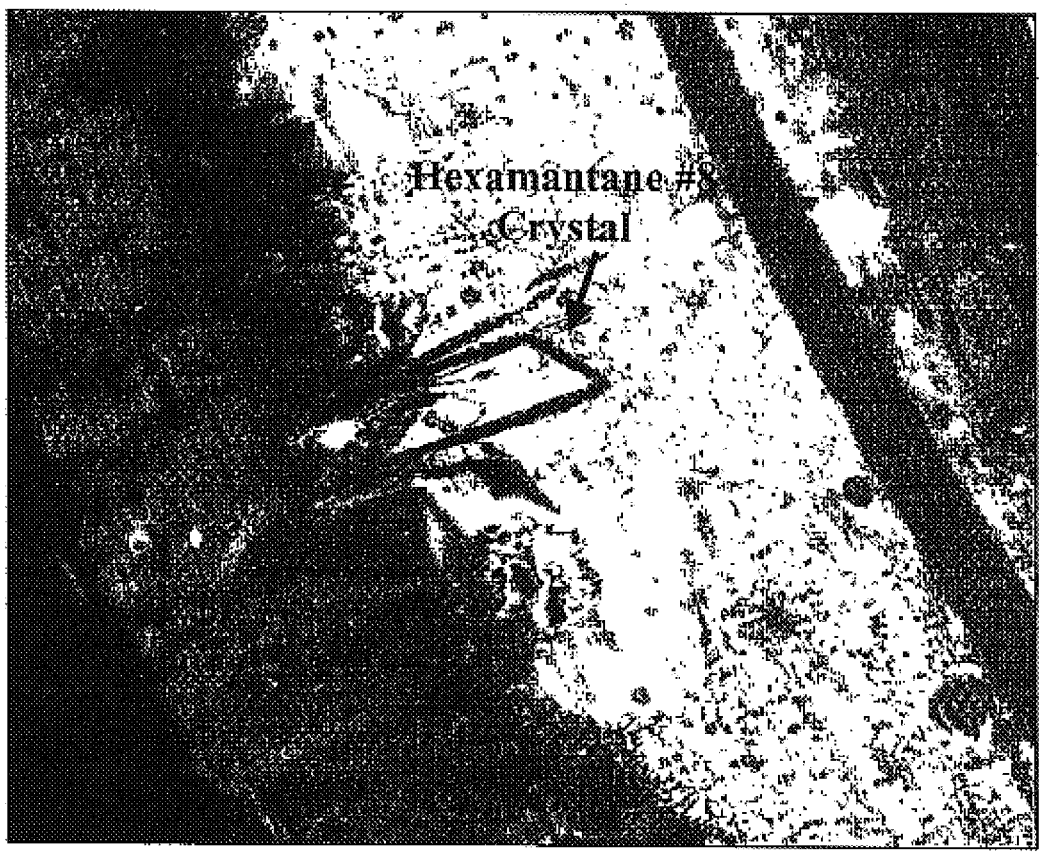
FIG. 11 illustrates a photomicrograph of hexamantane #8 crystals isolated from Feedstock B by preparative gas chromatography (FIGS. 7 and 9).

The highly concentrated hexamantanes were then allowed to crystallize either directly in the trap or from solution. Under the microscope at 30× magnification, crystals were visible in preparative GC trap fraction 1 (see FIG. 10). These crystals were perfectly clear and showed high refractive index. Crystals of hexamantane #2 had never existed before this isolation. Where concentrations are not high enough for crystallization to occur, further concentration by preparative GC may be necessary. FIG. 11 is a photomicrograph of hexamantane #8 that crystallized in preparative GC trap 3. Crystals of hexamantane #8 had never existed before this isolation.

Step 7

After obtaining crystals of suitable size, non-enantiomeric hexamantane components could be sent for structural determination using X-ray diffraction. Enantiomeric hexamantanes must undergo further separations to resolve the two components. Carbon framework structures of hexamantane components are shown in FIG. 2, including hexamantanes having enantiomeric forms. Detailed structural drawings are given in FIGS. 30 through 107.

EXAMPLE 2
Enrichment of Hexamantanes Using Pyrolysis

A method was developed to further purify distillate fractions such as distillate fractions #5–7 obtained from Feedstock B—Atmospheric distillation 650° F.+bottoms (Table 3A/B) exploiting the great thermal stability of the hexamantanes relative to other crude oil components. FIGS. 13(A, B,C) respectively, shows the GC profile of the distillate fractions #5–7 from Feedstock B—Atmospheric distillation 650° F.+bottoms (see FIG. 12 and Table 3A&B).

Removal of Non-Diamondoids Using Pyrolysis

Figure 14:
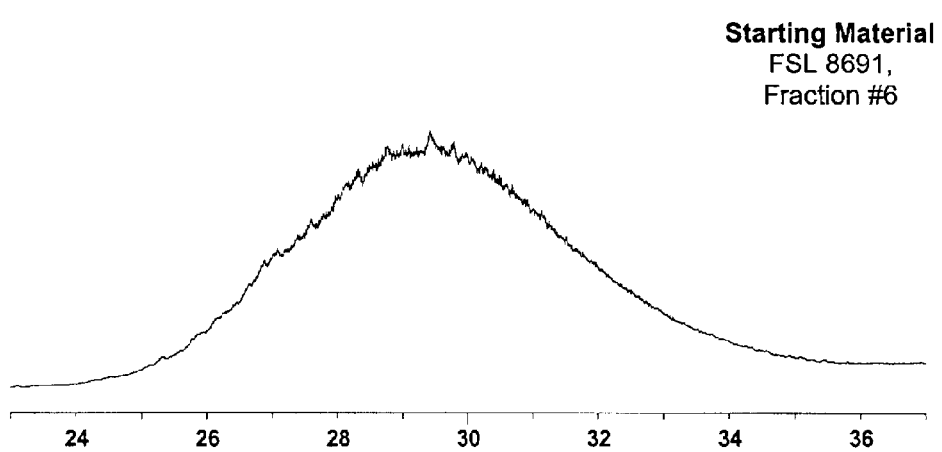
FIGS. 14(A, B) illustrates the gas chromatograms of the concentration of hexamantanes using pyrolysis.
Figure 14:
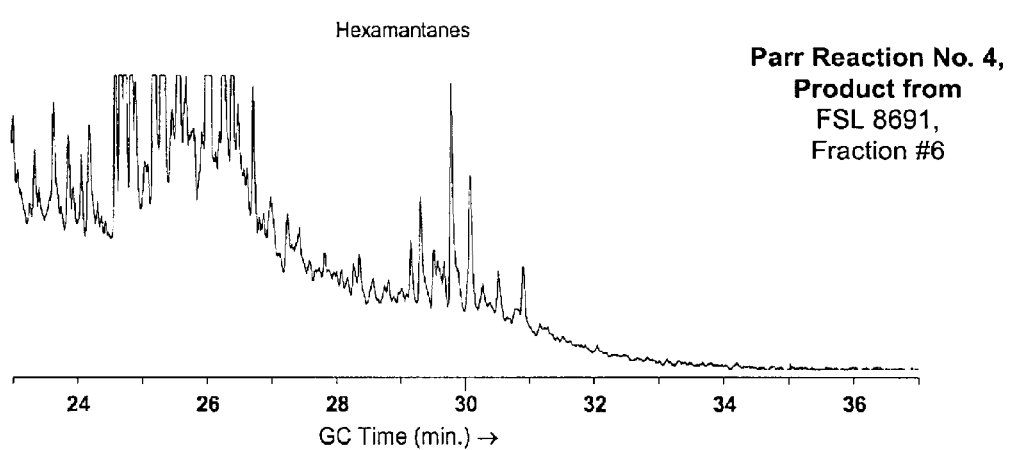

This method uses a reactor to pyrolyze and degrade a portion of the non-diamondoid components while enriching the diamondoids in the residue. Such reactors can operate at a variety of temperatures and pressures. FIGS. 14(A,B) illustrates this methods and show a gas chromatogram of the Feedstock B 650° F.+distillation fraction 6 (Table 3, FIG. 13) before pyrolysis and the resulting pyrolysis product. Prior to pyrolysis, the hexamantane peaks are obscured by the presence of non-diamondoid components. Pyrolysis can be used to degrade the non-diamondoid components to easily removable gas and coke like solids. As shown in FIG. 14B, the hexamantane peaks are clearly visible after pyrolysis.

A PARR® reactor, from PARR INSTRUMENT COMPANY, Moline, Ill., was used to process the distillation fractions obtained from vacuum distillation of a feedstream. For this example, Feedstock B 650° F.+distillation fraction 6 was used as a feedstock for pyrolysis. Pyrolysis was then conducted on 15 grams of this sample by heating the sample under vacuum in a vessel at 450° C. for 19.5 hours.

FIG. 14A shows the gas chromatogram of the distillation fraction and FIG. 14B shows the chromatograph of the products of the pyrolytic process. A comparison of the traces in FIGS. 14(A,B) show that the pyrolysis process has removed major non-diamondoid components leaving a residue enriched in hexamantane components.

EXAMPLE 3
Isolation of Hexamantanes Using HPLC

Figure 15:
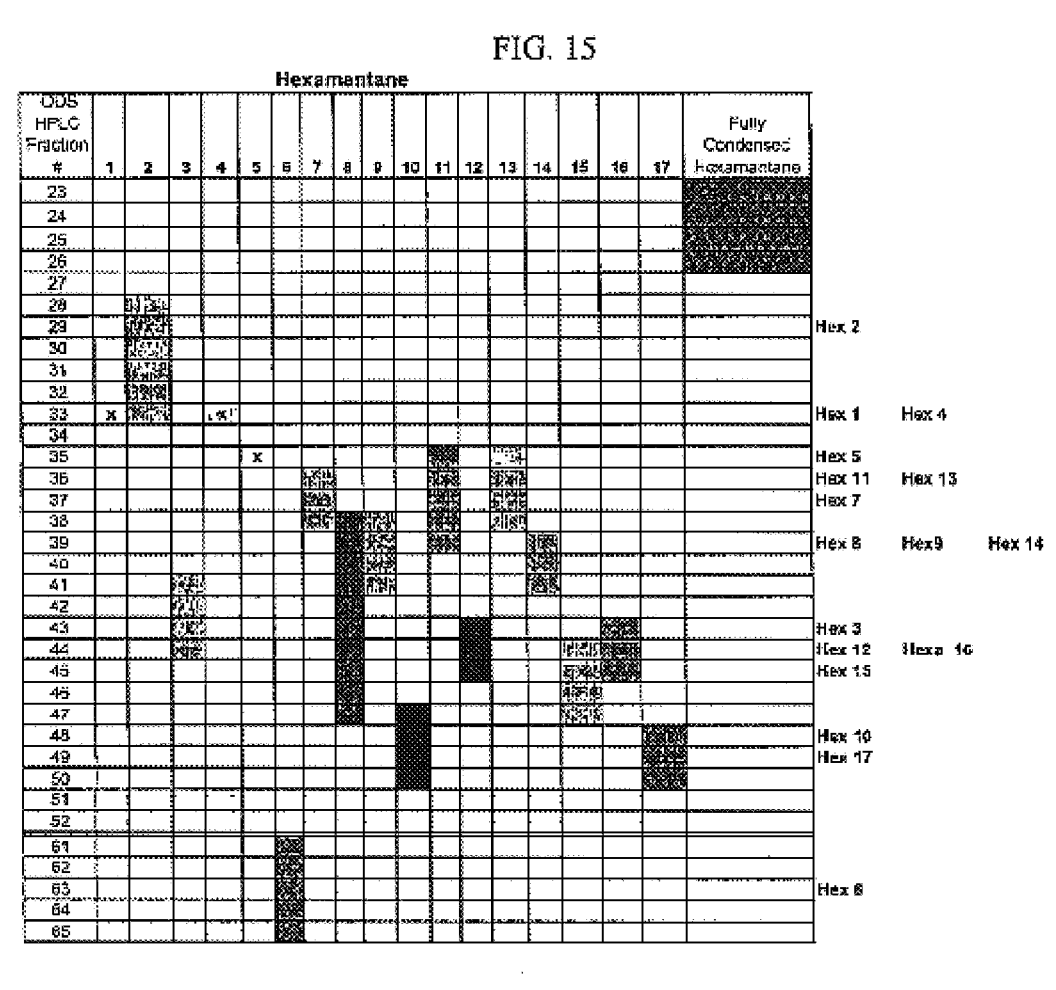

In addition to the gas chromatography and pyrolysis methods described above, HPLC was also shown to provide sufficient enrichments of some hexamantanes to allow for their crystallization. Suitable columns for use are well known to those skilled in the art. In some cases, reverse-phase HPLC with acetone as mobile phase can be used to effect this purification. A preparative ODS HPLC run of Feedstock B distillate cut 6 pyrolysis product saturated hydrocarbon fraction was performed and the HPLC chromatogram recorded using a differential refractometer: results are shown in FIG. 15. Fractions where taken during the run as indicated in FIG. 15. Most hexamantanes were found by GS/MS analysis of the fractions to display a different elution time on HPLC as indicated in FIG. 15. This is somewhat unexpected due to the similarity of the 396 molecular weight hexamantane isomers, but demonstrates the significant variation in properties of these hexamantanes based on differences in their carbon framework.

Figure 16:
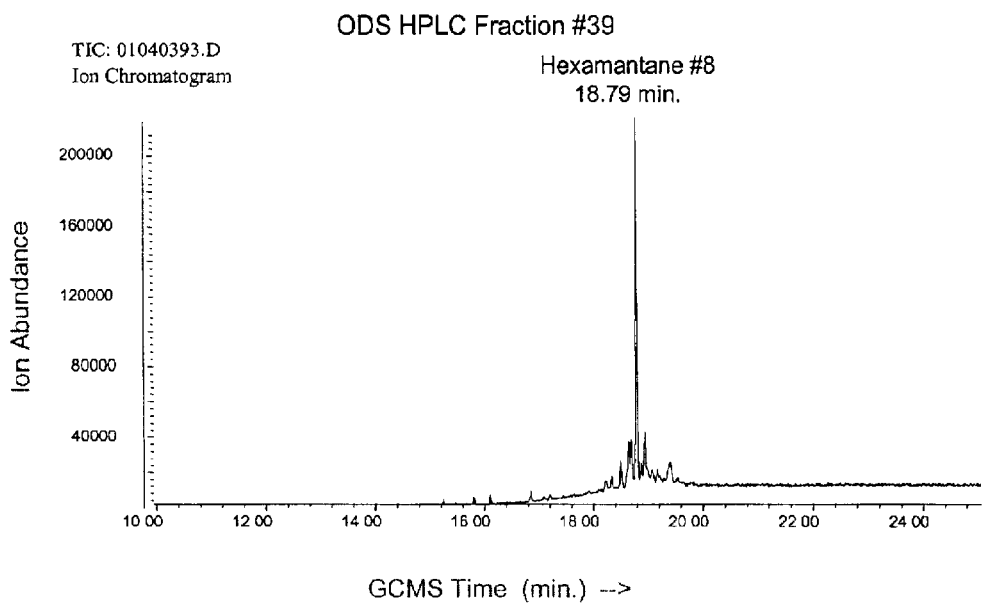
FIGS. 16(A, B) illustrates GC/MS total ion chromatogram (TIC) and mass spectrum of hexamantane #8 in ODS HPLC fraction #39 (FIG. 15).
Figure 16:
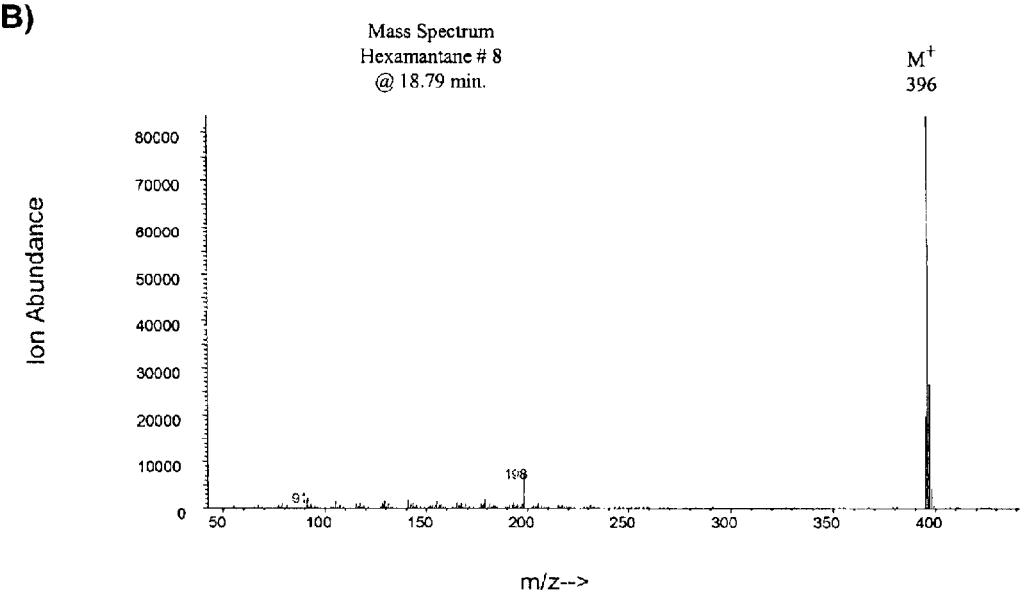
Figure 17:
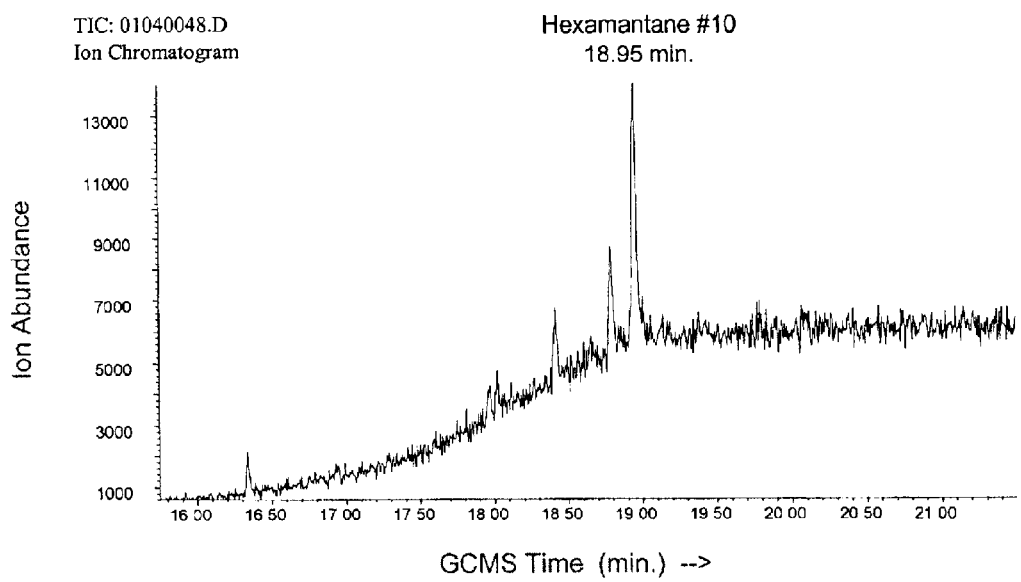
FIGS. 17(A, B) illustrates GC/MS total ion chromatogram (TIC) and mass spectrum of hexamantane #10 in ODS HPLC fraction 48 (FIG. 15).
Figure 17:
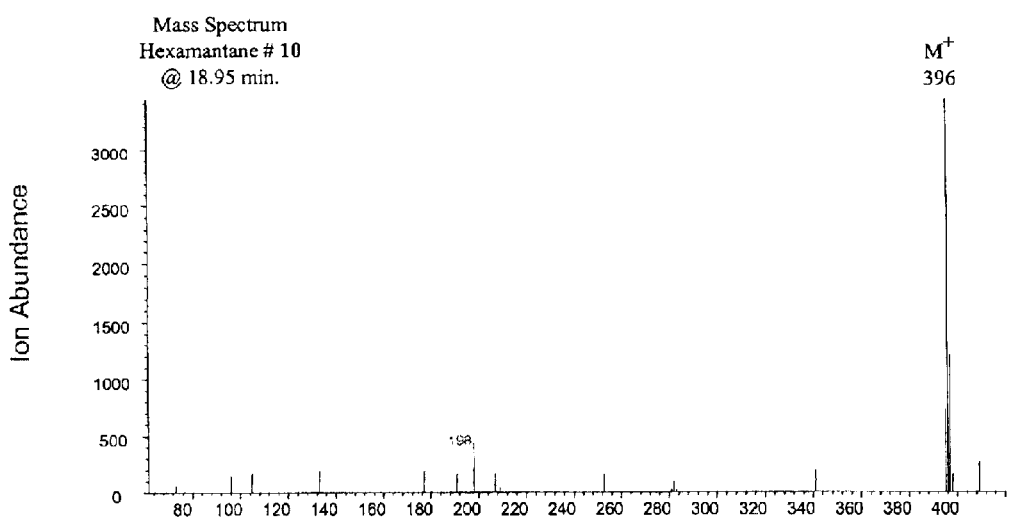
Figure 18:
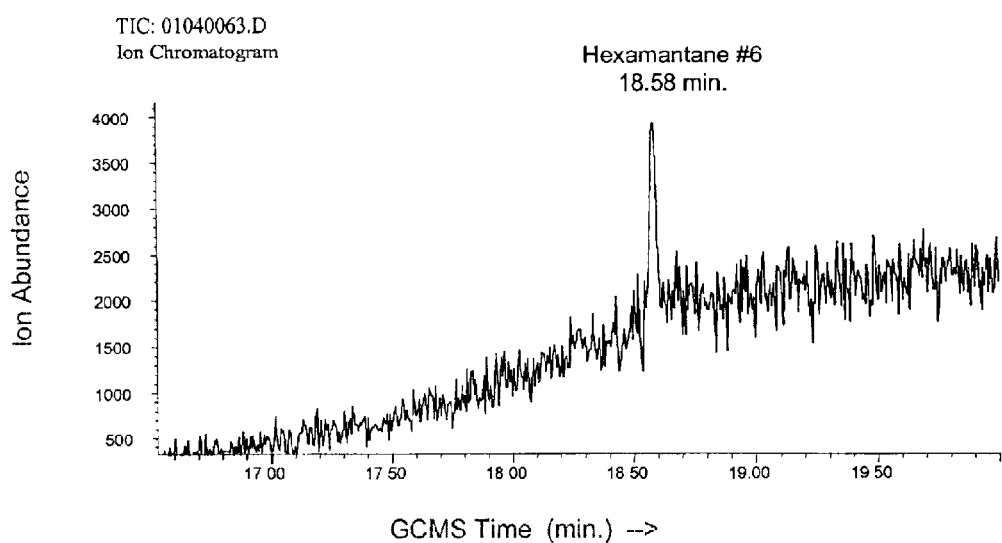
FIGS. 18(A, B) illustrates GC/MS total ion chromatogram (TIC) and mass spectrum of hexamantane #6 in ODS HPLC fraction 63 (FIG. 15).
Figure 18:
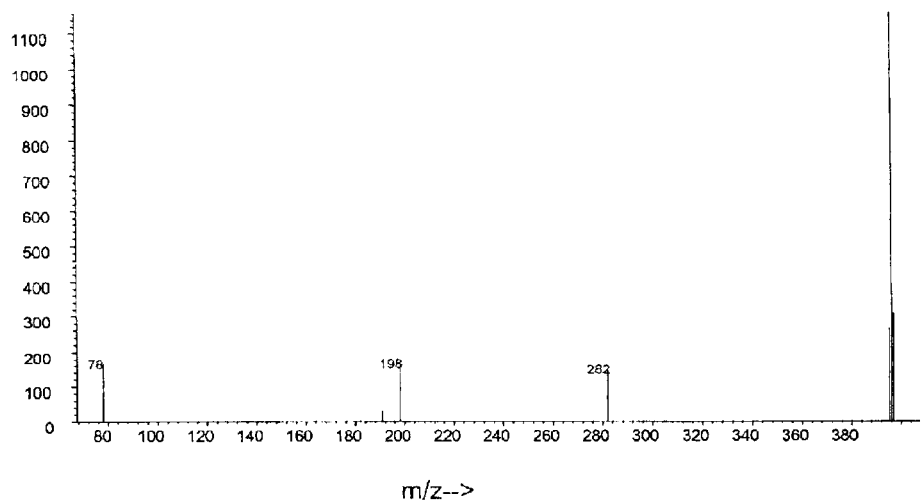
Figure 20:
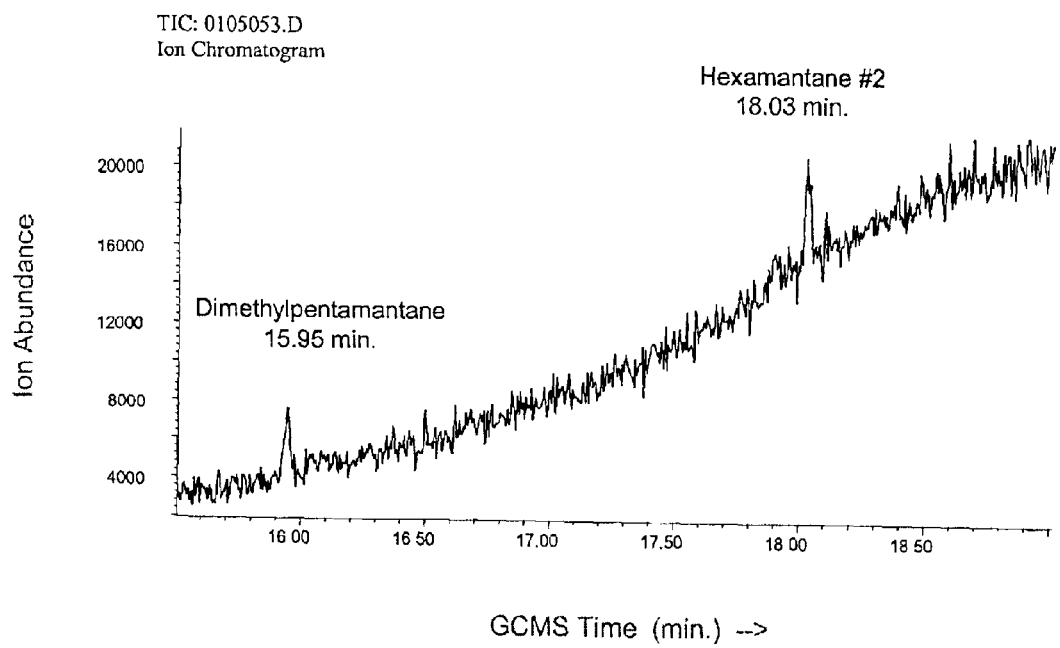
FIGS. 20(A, B) illustrates GC/MS total ion chromatogram (TIC) and mass spectrum of hexamantane #2 greatly enriched in Hypercarb HPLC fraction #53 (FIG. 19).
Figure 20:
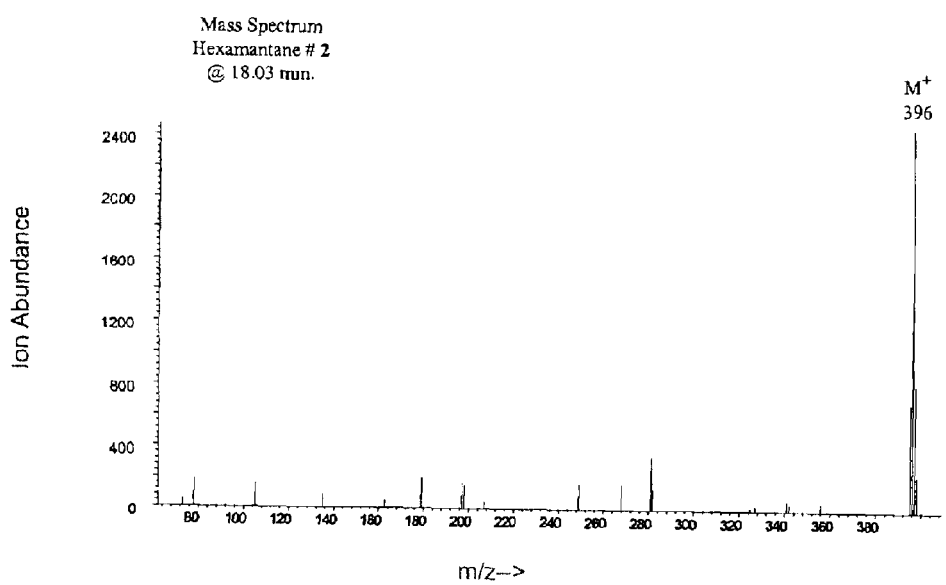

The HPLC columns used were two 50 cm×20 mm I.D. WHATMAN octadecyl silane (ODS) columns operated in series (Whatman columns are manufactured by Whatman Inc., USA). A 500 microliter sample of a solution of the cut 6 pyrolysis product saturated hydrocarbon fraction (54 mg) was injected into the columns. The columns were set-up using acetone at 5.00 ml/min as a mobile phase carrier. Some of the HPLC fractions reached the purity necessary for individual hexamantanes to crystallize As shown for Hexamantane #8 in ODS HPLC fraction #39 (FIG. 16), Hexamantane #10 in ODS HPLC fraction #48 (FIG. 17) and Hexamantane #6 in ODS HPLC fraction #63 (FIG. 18). Alternatively a HYPERCARB column (manufactured by Thermo Hypersil, Penn, USA) or other suitable column could be used to purify hexamantanes to concentrations necessary for them to crystallize. A preparative Hypercarb HPLC run of Feedstock B distillate cut 6 pyrolysis product saturated hydrocarbon fraction was performed and the HPLC chromatogram recorded using a differential refractometer: results are shown in FIG. 19. Fractions where taken during the run as indicated in FIG. 19. Most hexamantanes display different elution times (verified by GC/MS analysis) from one another on the Hypercarb HPLC system as indicated in FIG. 19. A comparison of FIGS. 15 and 19 illustrate the different elution times for the ODS versus Hypercarb HPLC systems. Some of the Hypercarb preparative HPLC fractions reached the purity necessary for individual hexamantanes to crystallize as shown for Hexamantane #2 in Hypercarb HPLC fraction #53 (FIG. 20). Also shown in this fraction is a substituted higher diamondoid, namely a dimethylpentamantane. The higher diamondoids in this fraction could be separated using further chromatographic techniques including preparative gas chromatography, additional HPLC runs using columns of different selectivity as outlined below. Additionally other techniques known in the crystallization art could be utilized including but not limited to fractional sublimation, progressive recrystalization or zone refining.

EXAMPLE 4
Purification of Single Hexamantane Isomers

As shown in Example 3, hexamantanes can be isolated in high purity by using HPLC methods. In this example, HPLC columns of different selectivities were used in succession to isolate single hexamantanes. FIG. 15 shows results of a preparative separation of the hexamantanes from distillation cut 6-pyrolysis product saturated hydrocarbon fraction using an octadecyl silane (ODS) HPLC column with acetone as a mobile phase. This first HPLC system consisted of two Whatman M20 10/50 ODS columns operated in series using acetone as mobile phase at 5.00 mL/min. The detector used was a differential refractometer. From this HPLC run, (FIG. 15) fractions 36 and 37 were combined and taken for further purification on a second HPLC system. This combined fraction (36 and 37) contained hexamantane #7, #11 and #13.

Further purification of combined ODS HPLC fractions (fractions 36 & 37) was achieved using a HYPERCARB stationary phase HPLC column having a different selectivity in the separation of various hexamantanes than the ODS column discussed above. FIG. 19 shows a preparative Hypercarb HPLC run for distillation cut 6 pyrolysis product saturated hydrocarbon indicating elution times of the individual hexamantanes as noted on the chart. The differences in elution times and elution order of hexamantanes on ODS and Hypercarb HPLC are seen by comparing FIGS. 15 and 19. For example, hexamantanes #11 and #13 elute together on the ODS HPLC system (FIG. 15) but in separate fractions (fractions 32 and 27, respectively) on the Hypercarb system (FIG. 19). By relying on the different elution order/times of these HPLC systems, fractions showing impurities or co-elution of higher diamondoids can be further purified by using an appropriate column of the different selectivities.

Using this method, a 50 microliter sample of approximately 1 mg of ODS HPLC combined fraction 36 & 37 in acetone was injected into the Hypercarb column, 10 mm I.D.×250 mm, operated using acetone at 3.00 mL/min as mobile phase (@480 psi), and using a differential refractometer detector.

Figure 21:
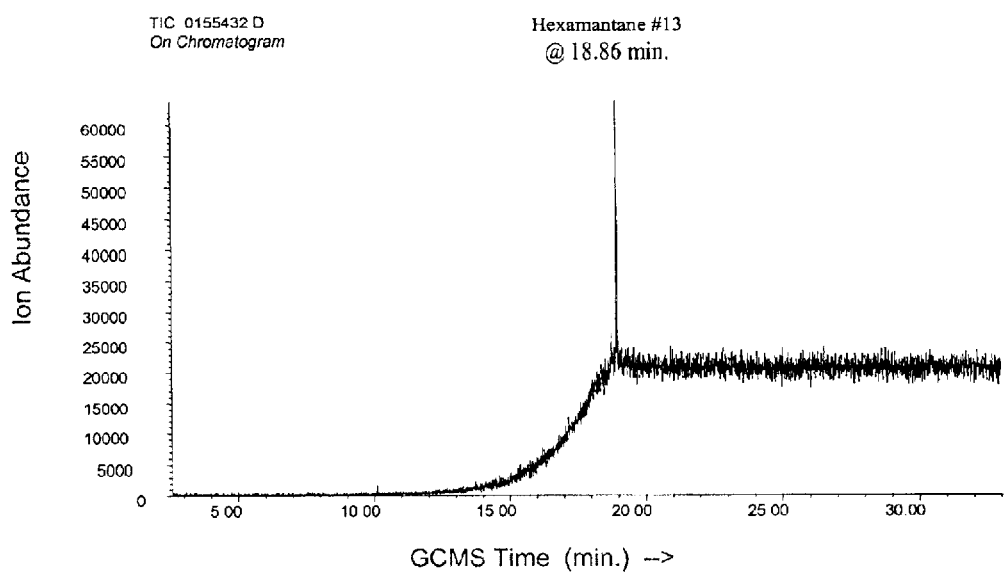
FIGS. 21(A, B) illustrates GC/MS total ion chromatogram (TIC) and mass spectrum of hexamantane #13 isolated using two different HPLC columns.
Figure 21:
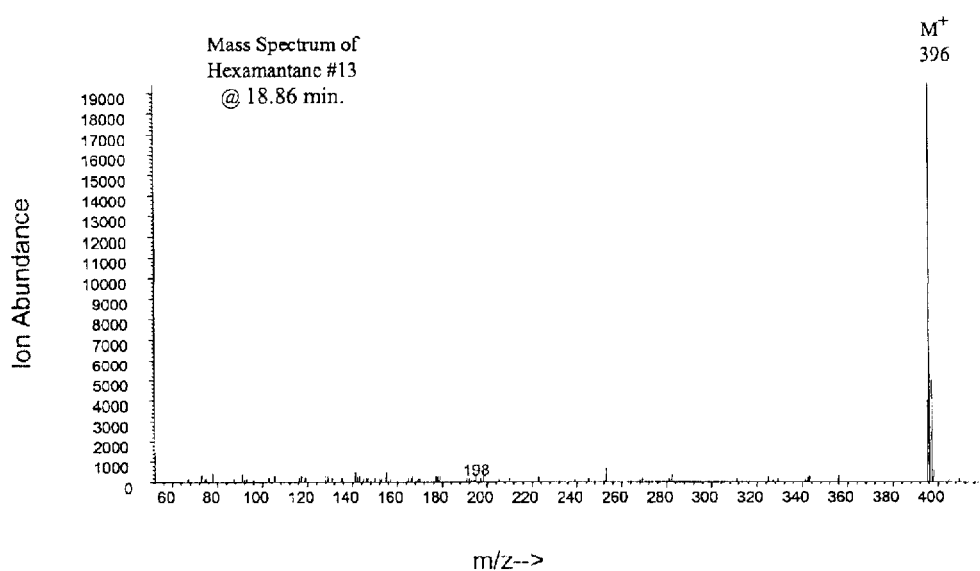
Figure 22:
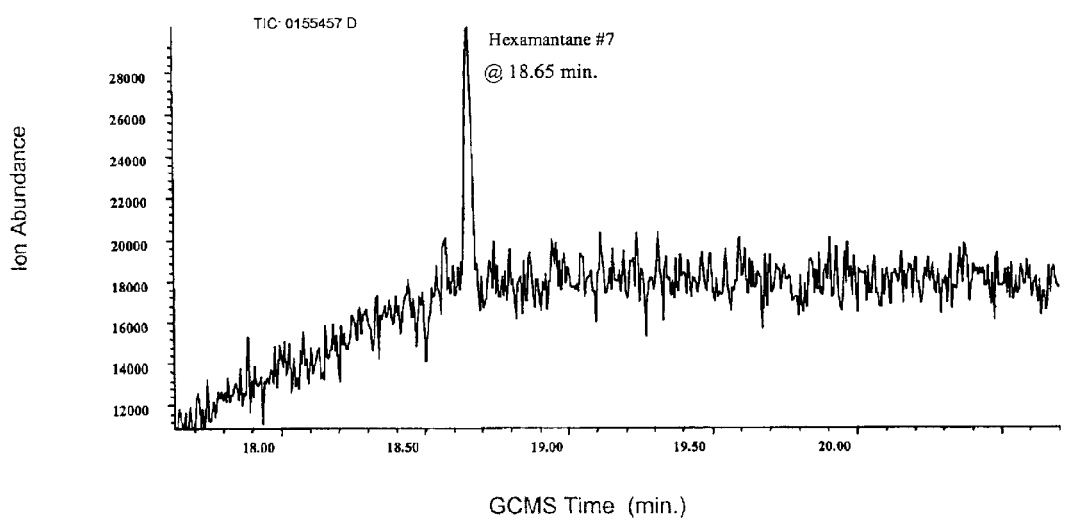
FIGS. 22(A, B) illustrates GC/MS total ion chromatogram (TIC) and mass spectrum of hexamantane #7 isolated using two different HPLC columns.
Figure 22:
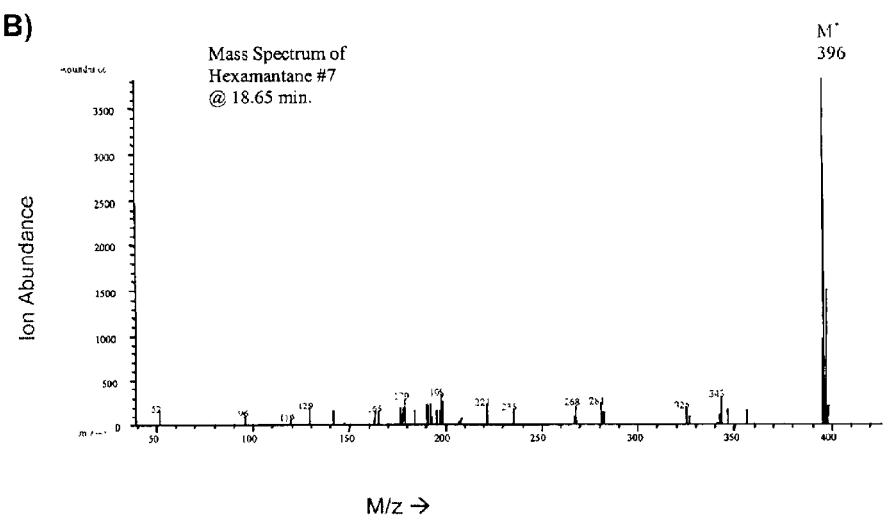

Using FIG. 19 as a guide, appropriate Hypercarb HPLC fractions were taken from this HPLC run thus obtain high purity hexamantane #13 demonstrated in FIG. 21. Other ODS HPLC fractions and Hypercarb HPLC cut points could be used to isolate the remaining hexamantanes. This different separation selectivity of ODS and Hypercarb facilitates isolation of hexamantanes or alternatively could be used to separate other higher diamondoids. The ODS and Hypercarb columns can also be used in reverse order for this isolation. FIG. 21 shows the GC/MS total ion chromatogram (TIC) of the hexamantane #13 containing Hypercarb HPLC fraction. The lower half of FIG. 21 illustrates the mass spectrum of the GC/MS peak, demonstrating the high purity of the isolated hexamantane #13. FIG. 22 shows the GC/MS total ion chromatogram (TIC) of the hexamantane #7 containing Hypercarb HPLC fraction. The lower half of FIG. 22 illustrates the mass spectrum of the GC/MS peak, demonstrating the high purity of the isolated hexamantane #7.

Figure 23:
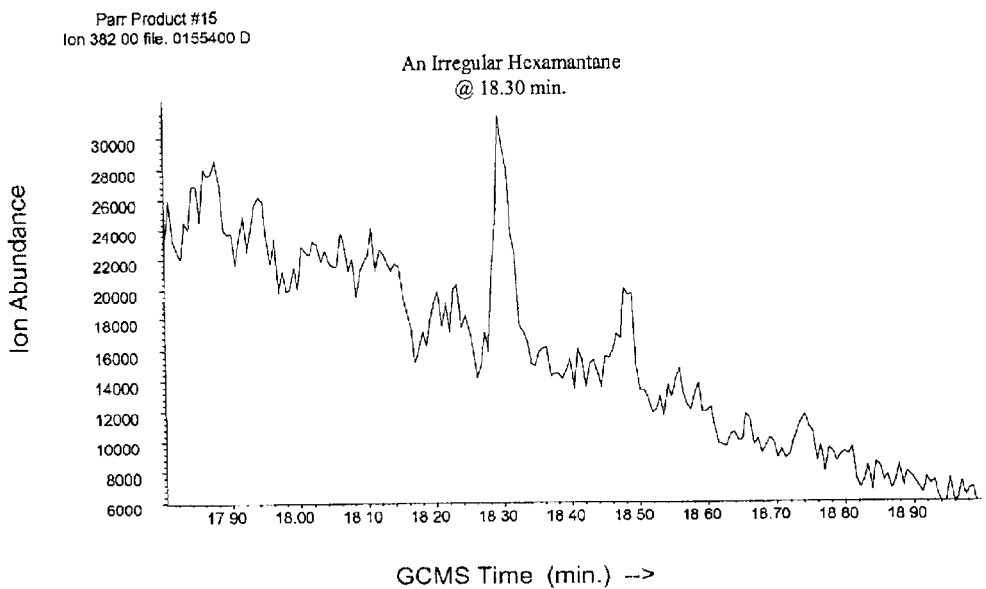
FIGS. 23(A, B) illustrates GC/MS reconstructed ion chromatogram m/z 382 and mass spectrum of a condensed "irregular" hexamantane (mol. wt. 382) in the saturated hydrocarbon fraction of the product of the pyrolytic processing of Feedstock B distillation fraction #6.
Figure 23:
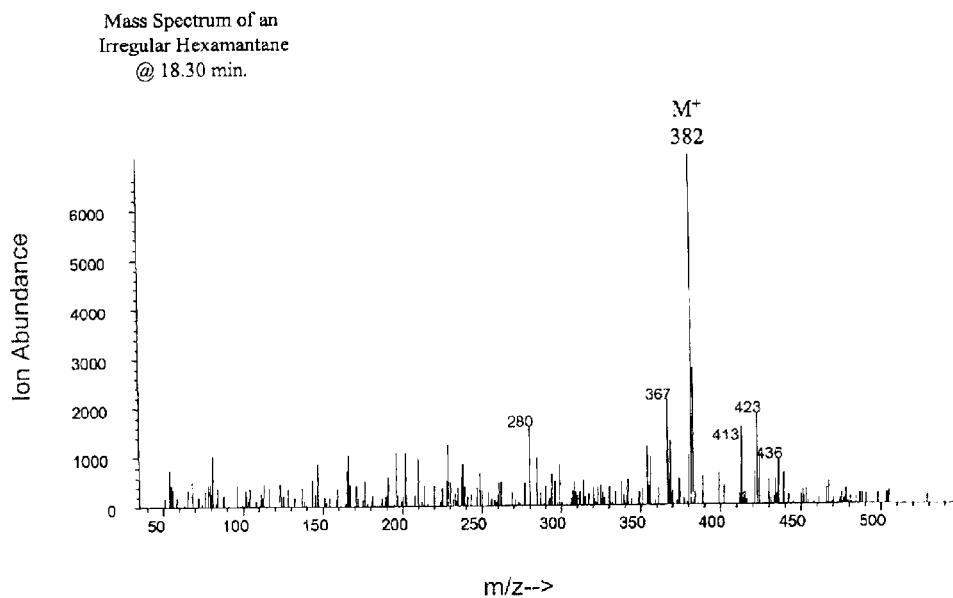
Figure 24:
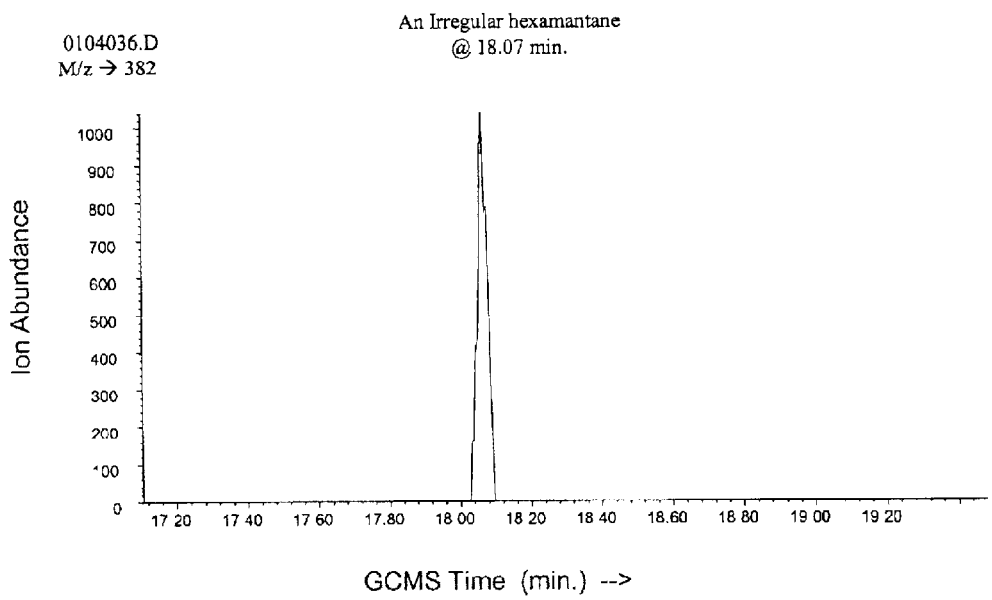
FIGS. 24(A, B) illustrates GC/MS reconstructed ion chromatogram m/z 382 and mass spectrum of an irregular hexamantane (mol. wt. 382) in the ODS HPLC fraction #36.
Figure 24:
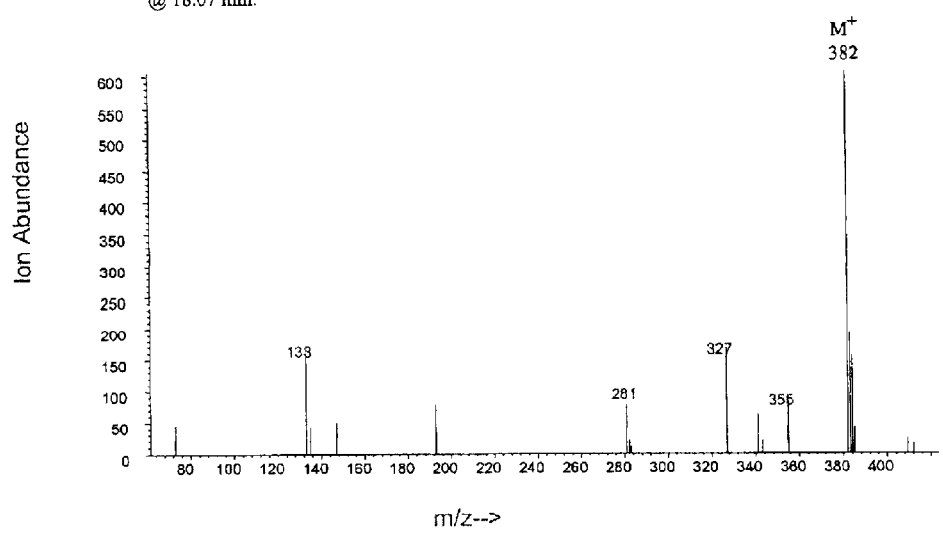

As indicated in FIG. 15, the various remaining ODS HPLC fractions containing other hexamantanes could be separated in the same way. By using similar methodology as above, i.e. fractionating hexamantane containing ODS fractions using the Hypercarb or other suitable column and collecting at corresponding elution times can lead to the isolation of the remaining hexamantanes in high purity. This is also true of the hexamantanes with molecular weights of 382, "irregular" hexamantanes, that are in much lower abundance in our feedstocks than hexamantanes showing molecular weight of 396. FIGS. 23A and 24A present reconstructed ion chromatograms for m/z 382 showing hexamantanes running at 18.30 min. and 18.07 min., respectively. FIGS. 23B and 24B also show the corresponding mass spectra for these 18.30 min. and 18.07 min. peaks, demonstrating the presence of hexamantanes with a 382 molecular weight in the saturated hydrocarbon fraction from the product of pyrolytic processing of Feedstock B distillation fraction #6. These low-concentration 382 molecular weight hexamantanes have an elution order on our GC/MS assay that is intermediate between 396 molecular weight hexamantanes #2 and 3. Another 382 molecular weight hexamantane shows up in ODS HPLC fraction #36 (FIG. 24A). A very strong molecular ion in the mass spectrum (in this case m/z 382, FIG. 24B) for the m/z 382 component running at 18.07 min. FIG. 24A is characteristic of a diamondoid component.

The enantiomeric hexamantanes are not resolved in GS/MS and therefore, these enantiomeric pairs are referenced within a single number. These enantiomers can be isolated by chiral separation methods.

FIGS. 30 through 107 illustrate the size and structure with views into various diamond crystal lattice planes for thirty-nine hexamantanes.

EXAMPLE 5
Isolation of Substituted Hexamantane

Figure 25:
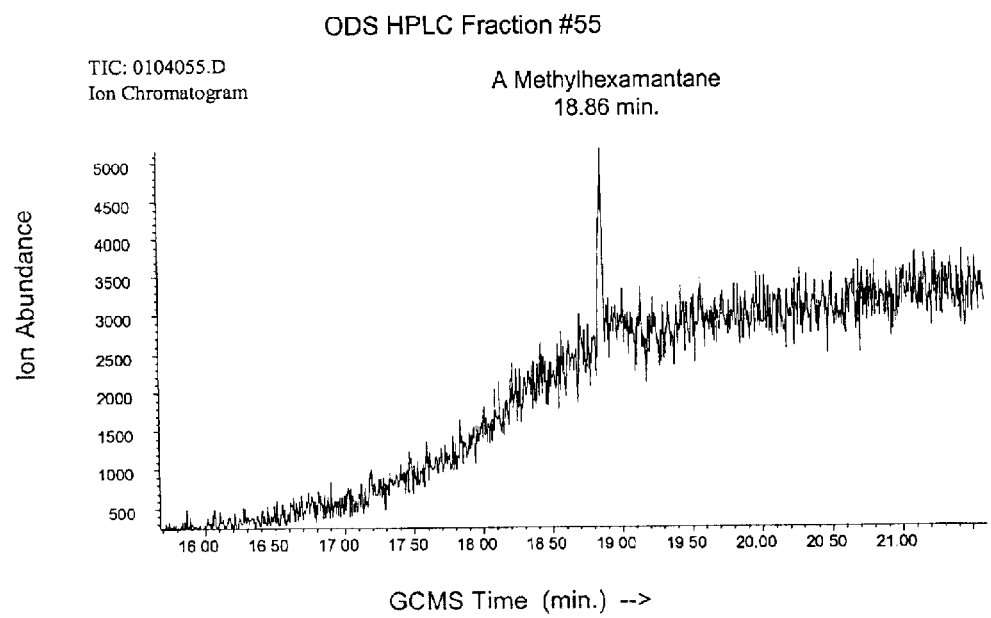
FIGS. 25A, B) illustrates GC/MS total ion chromatogram (TIC) and mass spectrum of a methylhexamantane (mol. wt. 410) isolated in high purity in ODS HPLC fraction #55.
Figure 25:
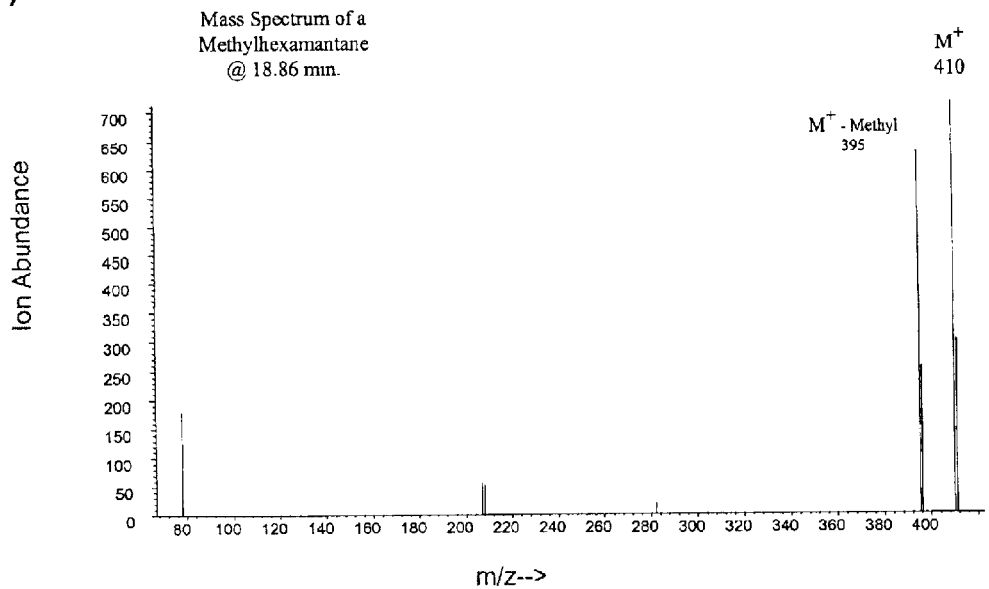
Figure 26:
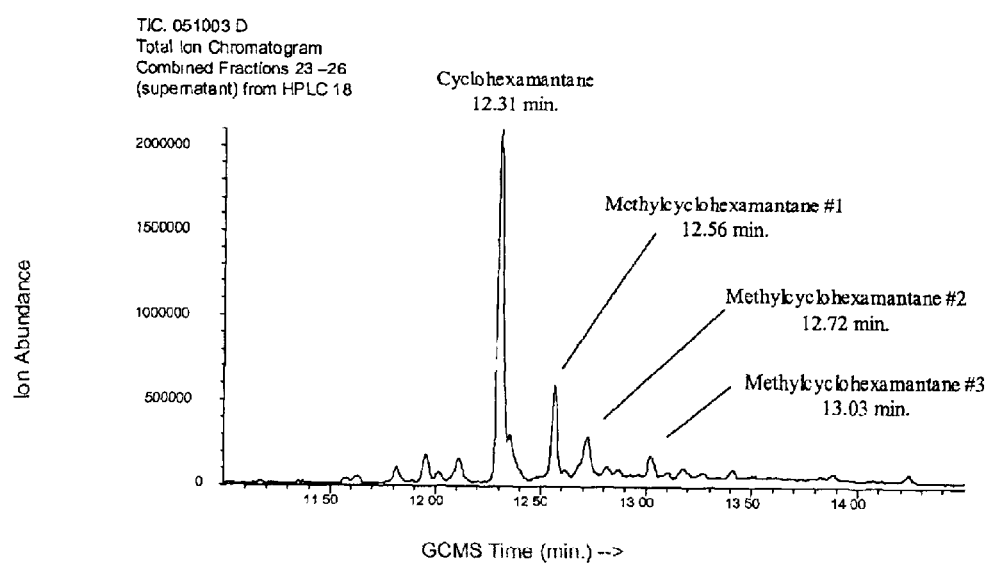
FIG. 26 illustrates GC/MS total ion chromatogram (TIC) and mass spectrum of ODS HPLC combined fractions #23–26.
Figure 27:
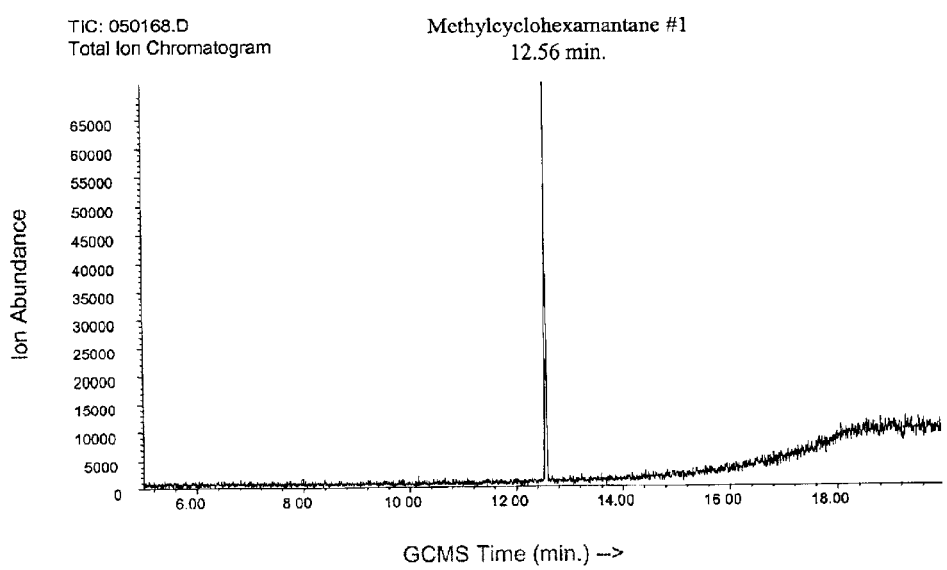
FIGS. 27A, B) illustrates GC/MS total ion chromatogram (TIC) and mass spectrum of a methylcyclohexamantane #1 (mol. wt. 356) isolated in high purity in using multi-column stationary phase HPLC (ODS followed by Hypercarb).
Figure 27:
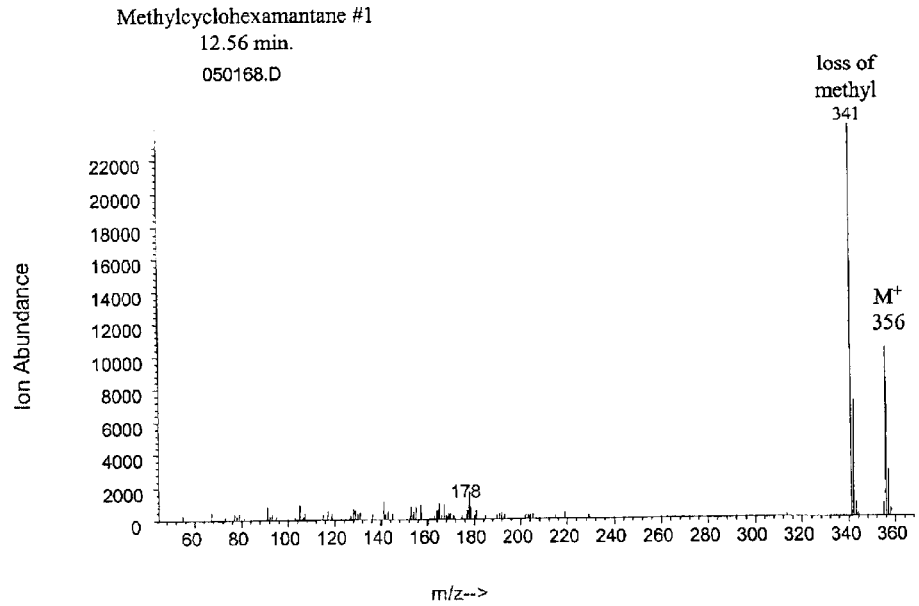
Figure 28:
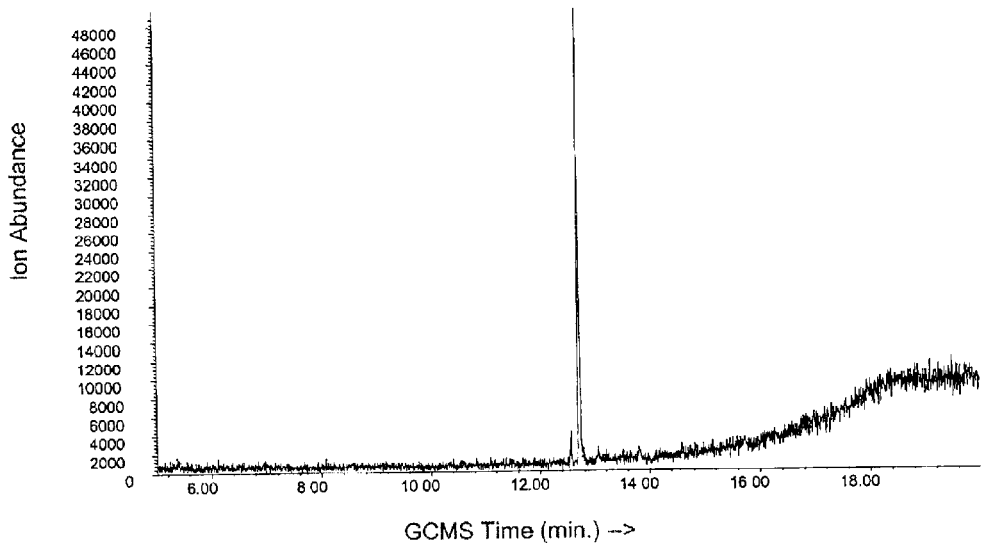
FIGS. 28A, B) illustrates GC/MS total ion chromatogram (TIC) and mass spectrum of a methylcyclohexamantane #2 (mol. wt. 356) isolated in high purity using multi-column stationary phase HPLC (ODS followed by Hypercarb).
Figure 28:
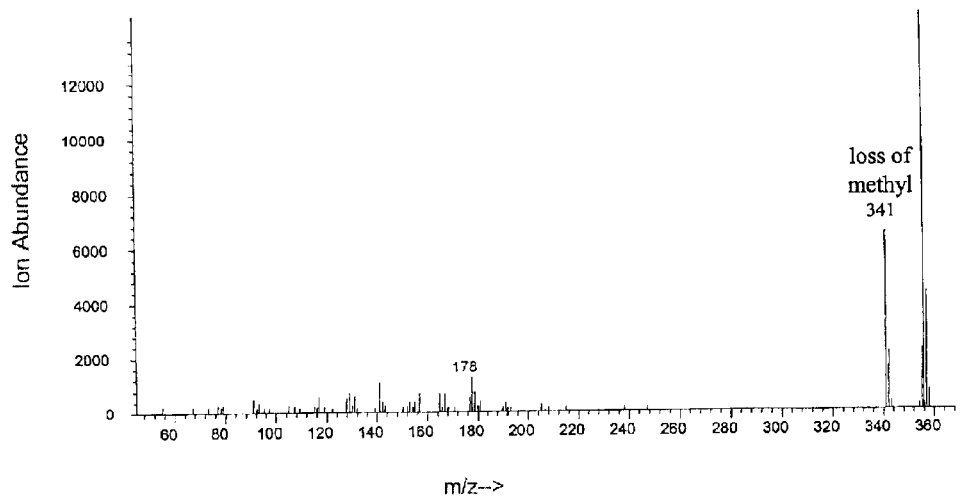
Figure 29:
Figure 29:

Substituted hexamantane including alkylhexamantanes also are present in Feedstock A and B. These natural substituted hexamantane have uses similar to the unsubstituted hexamantanes, can act as useful intermediates in various hexamantane applications (e.g., polymer production) and can be de-alkylated to yield the corresponding underivatized hexamantane. Accordingly, methods for the isolation of individual substituted hexamantane were devised and exemplified by the isolation of alkyl substituted substituents. Substituted hexamantane including alkylhexamantanes can be isolated in high purity using a single HPLC separation of appropriate distillation cuts as exemplified by FIGS. 25A/B, and demonstrated for the hexamantanes in Example 3. FIGS. 25(A/B) shows that fraction #55 from an ODS HPLC separation (FIG. 15) of the saturated hydrocarbon fraction from Feedstock B, distillation fraction 6 pyrolysis contains a methylated hexamantane in high purity. Monomethylated hexamantanes have a molecular weight of 410 (yielding a mass spectrometric molecular ion of m/z 410, and show a mass spectrometric loss of the methyl group giving the m/z 395 fragment ion (FIG. 25B)). Isolation of substituted hexamantane components by HPLC may require multiple columns with different selectivities. For example, the ODS and Hypercarb HPLC columns were run in succession to isolate the methylcyclohexamantane components (methyl substituted derived from mol. weight 342 hexamantane) from distillation cut 6-pyrolysis product saturated hydrocarbon fraction. This first HPLC system consisted of two Whatman M20 10/50 ODS columns operated in series using acetone as mobile phase at 5.00 mL/min. The detector used was a differential refractometer. From this HPLC run, fractions #23–26 (FIG. 26) were combined and taken for further purification on a second HPLC system. This combined fraction contained a mixture of hexamantane (mol. weight 342 referred to as cyclohexamantane), eluting on our GC/MS system at 12.31 minutes as well as three methylcyclohexamantanes (#1–3) eluting at 12.56, 12.72 and 13.03 minutes, respectively. Further purification of this mixture (i.e. combined ODS HPLC fractions #23–26) was achieved using a Hypercarb stationary phase HPLC column which exhibited a different selectivity than the ODS column discussed above. A 50 microliter sample of approximately 1 mg of this combined fraction in acetone was injected into the Hypercarb column, 10 mm I.D.×250 mm, operated using acetone at 3.00 mL/min as mobile phase (@480 psi), and using a differential refractometer detector. In this Hypercarb system methylcyclohexamantane #1 elutes primarily in fractions 18–22 and methylcyclohexamantane #2 elutes primarily in fractions 23–25. Methylcyclohexamantane #1 and #2 where isolated in sufficient purity to form crystals. A GC/MS total ion chromatogram and mass spectrum of these compounds is illustrated in FIGS. 27(A,B) and 28(A,B) and illustrated as photomicrographs in FIGS. 29(A,B). FIG. 29A illustrates a crystal precipitated from Hypercarb HPLC fractions #19–21 and FIG. 29B illustrates a crystal precipitated from Hypercarb HPLC fractions #23.

Enantiomeric pairs must undergo further separations to resolve the two components. After obtaining crystals of suitable size, non-enantiomeric alkylhexamantanes can be sent for structural determination by x-ray crystallography.

What is claimed is:

1. A composition comprising diamondoids wherein at least about 25 weight percent of the diamondoids are one or more hexamantane components, subject to the proviso that when there is only one hexamantane component it is not unsubstituted cyclohexamantane represented by the formula $C_{26}H_{30}$.

2. A composition of claim 1 wherein from 50 to 100 weight percent of the diamondoids are one or more hexamantane components.

3. A composition of claim 1 wherein from 70 to 100 weight percent of the diamondoids are one or more hexamantane components.

4. A composition of claim 1 wherein from 95 to 100 weight percent of the diamondoids are one or more hexamantane components.

5. A composition of claim 1 wherein from 99 to 100 weight percent of the diamondoids are one or more hexamantane components.

6. The composition of any of claims 1–5, wherein the one or more hexamantane components are a single hexamantane component.

7. The composition of any of claims 1–5 wherein the one or more hexamantane components are isolated optical isomers.

8. The composition of any of claims 1–5, wherein the one or more hexamantane components are isomeric hexamantane components.

9. The composition of any of claims 1–5, wherein the one or more hexamantane components are one or more of the hexamantane components represented by the formula $C_{30}H_{36}$.

10. The composition of any of claims 1–5, wherein the one or more hexamantane components are one or more of the hexamantane components represented by the formula $C_{29}H_{34}$.

11. The composition of any of claims 1–5 wherein the hexamantane components comprise unsubstituted hexamantane components.

12. The composition of any of claims 1–5 wherein the hexamantane components comprise substituted hexamantane components having from 1 to 10 alkyl substituents.

13. A composition comprising at least about 10% by weight of one or more hexamantane components, subject to the proviso that when there is only one hexamantane component it is not unsubstituted cyclohexamantane represented by the formula $C_{26}H_{30}$.

14. The composition of claim 13 containing from 50 to 100% by weight of one or more hexamantane components.

15. The composition of claim 13 containing from 70 to 100% by weight of one or more hexamantane components.

16. The composition of claim 13 containing from 95 to 100% by weight of one or more hexamantane components.

17. The composition of claim 13 containing from 99 to 100% by weight of one or more hexamantane components.

18. The composition of claims 13–17 wherein the one or more hexamantane components are a single hexamantane component.

19. The composition of claim 1, wherein the one or more hexamantane components are selected from the group consisting of

[1(2)314] enantiomer A hexamantane
[1(2)314] enantiomer B hexamantane
[12(1)32] enantiomer A hexamantane
[12(1)32] enantiomer B hexamantane
[12(1)34] enantiomer A hexamantane
[12(1)34] enantiomer B hexamantane
[12(1,3)4] hexamantane
[12(3)14] enantiomer A hexamantane
[12(3)14] enantiomer B hexamantane
[121(2)3] enantiomer A hexamantane
[121(2)3] enantiomer B hexamantane
[12123] enantiomer A hexamantane
[12123] enantiomer B hexamantane
[12131] enantiomer A hexamantane
[12131] enantiomer B hexamantane
[12134] enantiomer A hexamantane
[12134] enantiomer B hexamantane
[12324] enantiomer A hexamantane
[12324] enantiomer B hexamantane
[12341] enantiomer A hexamantane
[12341] enantiomer B hexamantane
[1(2)3(1)2] hexamantane
[12(3)12] hexamantane
[121(3)4] hexamantane
[12121] hexamantane
[12321] hexamantane
[1(2)3(1)4] enantioner A hexamantane
[1(2)3(1)4] enantiomer B hexamantane.

20. The composition of claim 1, wherein the one or more hexamantane components are in crystalline form.

21. A process for recovering a composition enriched in one or more hexamantane components which process comprises:
   a. selecting a feedstock comprising recoverable amounts of hexamantane components and nonhexamantane components;
   b. removing from the feedstock a sufficient amount of nonhexamantane components having boiling points less than the lowest boiling point hexamantane component under conditions to form a treated feedstock enriched in hexamantane components which can be recovered;
   c. recovering a composition enriched in one or more hexamantane components from said treated feedstock formed in b) above with one or more additional separation techniques selected from the group consisting of chromatographic techniques, thermal diffusion techniques, zone refining, progressive recrystallization and size separation techniques.

22. A process for recovering a composition enriched in hexamantane components which process comprises:
   a. selecting a feedstock comprising recoverable amounts of hexamantane components and nonhexamantane components including nondiamondoid components;
   b. removing from the feedstock a sufficient amount of nonhexamantane components having a boiling point less than the lowest boiling point hexamantane component under conditions to form a treated feedstock enriched in hexamantane components which can be recovered;
   c. thermally degrading said treated feedstock to pyrolyze at least a sufficient amount of nondiamondoid components therefrom under conditions to form a thermally treated feedstock retaining recoverable amounts of hexamantane;
   d. recovering a composition enriched in one or more hexamantane components from said thermally treated feedstock formed in c) above with one or more additional separation techniques selected from the group consisting of chromatographic techniques, thermal diffusion techniques, zone refining, progressive recrystallization and size separation techniques.

23. A process for recovering a composition enriched in one or more hexamantane components which process comprises:
   a. selecting a feedstock comprising recoverable amounts of hexamantane components and nonhexamantane components including nondiamondoid components;
   b. thermally degrading said feedstock to pyrolyze at least a sufficient amount of nondiamondoid components therefrom under conditions to provide a thermally treated feedstock retaining recoverable amounts of hexamantane;
   c. removing from the thermally treated feedstock a sufficient amount of nonhexamantane components having a boiling point less than the lowest boiling point of hexamantane component under conditions to form a treated feedstock enriched in hexamantanes components which can be recovered;
   d. recovering a composition enriched in one or more hexamantane components from said treated feedstock recovered in c) above with one or more additional separation techniques selected from the group consisting of chromatographic techniques, thermal diffusion techniques, zone refining, progressive recrystallization and size separation techniques.

24. A process for recovering a composition enriched in one or more hexamantane components which process comprises:
   a. selecting a feedstock comprising recoverable amounts of hexamantane components and nonhexamantane components;
   b. fractionating the feedstock to form one or more cuts enriched in materials having boiling points in the range of from just below the boiling point of the lowest boiling hexamantane component to just above the boiling point of the highest boiling hexamantane component;
   c. recovering a composition enriched in one or more hexamantane components from said one or more cuts formed in b) above with one or more additional separation techniques selected from the group consisting of chromatographic techniques, thermal diffusion techniques, zone refining, progressive recrystallization and size separation techniques.

25. A process for recovering a composition enriched in one or more hexamantane components which process comprises:
   a. selecting a feedstock comprising recoverable amounts of hexamantane components and nonhexamantane components including nondiamondoid components;
   b. fractionating the feedstock to form one or more cuts enriched in materials having boiling points in the range of from just below the boiling point of the lowest boiling hexamantane component to just above the boiling point of the highest boiling hexamantane component;
   c. thermally degrading one or more cuts said to pyrolyze at least a sufficient amount of nondiamondoid components therefrom under conditions to form one or more thermally treated cuts retaining recoverable amounts of hexamantane;
   d. recovering a composition comprising one or more hexamantane components from one or more said thermally treated cuts formed in c) above with one or more additional separation techniques selected from the group consisting of chromatographic techniques, thermal diffusion techniques, zone refining, progressive recrystallization and size separation techniques.

26. A process for recovering a composition enriched in one or more hexamantane components which process comprises:
   a. selecting a feedstock comprising recoverable amounts of hexamantane components and nonhexamantane compounds including nondiamondoid components;
   b. thermally degrading said feedstock to pyrolyze at least a sufficient amount of nondiamondoid components therefrom under conditions to provide a thermally treated feedstock retaining recoverable amounts of hexamantane;
   c. fractionating the thermally treated feedstock to form one or more cuts enriched in materials having boiling points in the range of from just below the boiling point of the lowest boiling hexamantane component to just above the boiling point of the highest boiling hexamantane component;
   d. recovering a composition enriched in one or more hexamantane components from one or more cuts formed c) above with one or more additional separation techniques selected from the group consisting of chromatographic techniques, thermal diffusion techniques, zone refining, progressive recrystallization and size separation techniques.

27. The process according to any of claims 24–26 wherein said boiling point range is a range having atmospheric equivalents of between about 330 to about 550° C.

28. The process according to any of claims 21–26 wherein said separation technique is a chromatographic technique.

29. The process according to claim 28 wherein said chromatographic technique is selected from the group consisting of liquid chromatography, preparative gas chromatography and high performance liquid chromatography.

30. The process according to claim 28 wherein said additional separation technique is high performance liquid chromatography comprising one or more high performance liquid chromatography columns.

31. The process according to claim 30 wherein the high performance liquid chromatography columns are selected to have a different specificity to the hexamantane components.

32. A product prepared by the process of claim 21.
33. A product prepared by the process of claim 22.
34. A product prepared by the process of claim 23.
35. A product prepared by the process of claim 24.
36. A product prepared by the process of claim 25.
37. A product prepared by the process of claim 26.

* * * * *